US011654294B2

(12) United States Patent
van de Ven et al.

(10) Patent No.: US 11,654,294 B2
(45) Date of Patent: May 23, 2023

(54) INTRANASAL ILLUMINATION DEVICES

(71) Applicant: KNOW Bio, LLC, Durham, NC (US)

(72) Inventors: Antony Paul van de Ven, Nong Kae (TH); Michael John Bergmann, Atlanta, GA (US)

(73) Assignee: KNOW Bio, LLC, Morrisville, NC (US)

( * ) Notice: Subject to any disclaimer, the term of this patent is extended or adjusted under 35 U.S.C. 154(b) by 0 days.

(21) Appl. No.: 17/201,120

(22) Filed: Mar. 15, 2021

(65) Prior Publication Data
US 2022/0288414 A1 Sep. 15, 2022

(51) Int. Cl.
*A61N 5/06* (2006.01)

(52) U.S. Cl.
CPC ...... *A61N 5/0603* (2013.01); *A61N 2005/063* (2013.01); *A61N 2005/0607* (2013.01); *A61N 2005/0643* (2013.01); *A61N 2005/0659* (2013.01); *A61N 2005/0661* (2013.01); *A61N 2005/0663* (2013.01)

(58) Field of Classification Search
CPC .......... A61N 5/0603; A61N 2005/0607; A61N 2005/063; A61N 2005/0643; A61N 2005/0659; A61N 2005/0661; A61N 2005/0663
See application file for complete search history.

(56) References Cited

U.S. PATENT DOCUMENTS

| 1,244,819 A | 10/1917 | Young |
| 2,884,926 A | 5/1959 | Grasso |
| 4,466,434 A | 8/1984 | Brownstein |
| (Continued) |

FOREIGN PATENT DOCUMENTS

| AU | 2016100390 A4 | 7/2016 |
| CN | 101687101 A | 3/2010 |
| (Continued) |

OTHER PUBLICATIONS

Definition of within. Collins Dictionary, retrieved on Sep. 15, 2022; Retrieved from the Internet: <https://www.collinsdictionary.com/us/dictionary/english/within> (Year: 2022).*

(Continued)

*Primary Examiner* — Gary Jackson
*Assistant Examiner* — Sebastian X Lukjan
(74) *Attorney, Agent, or Firm* — Withrow & Terranova, P.L.L.C.

(57) ABSTRACT

Devices and methods for impinging light on tissue to induce one or more biological effects, and more particularly illumination devices and related methods that may be used for intranasal delivery of irradiation are disclosed. Exemplary illumination devices may include a light guide that is optically coupled with a light source, where the light guide may be configured for insertion along one or more intranasal passageways. In this manner, the light guide may provide irradiation of light to tissues along or near the upper respiratory tract to prevent and/or treat various infections and other tissue conditions thereof. Light guides may include flexible materials with suitable dimensions and/or shapes that allow the light guides to follow variable paths of intranasal passageways during use.

43 Claims, 17 Drawing Sheets

(56) References Cited

U.S. PATENT DOCUMENTS

| | | |
|---|---|---|
| 4,736,745 A | 4/1988 | Gluckman |
| 5,074,295 A | 12/1991 | Willis |
| 5,228,431 A | 7/1993 | Giarretto |
| 5,282,462 A | 2/1994 | Kudo |
| 5,292,346 A | 3/1994 | Ceravolo |
| 5,541,822 A | 7/1996 | Bamber |
| 5,549,639 A | 8/1996 | Ross |
| 5,611,793 A | 3/1997 | Wilson et al. |
| 5,616,140 A | 4/1997 | Prescott |
| 5,634,711 A | 6/1997 | Kennedy et al. |
| 5,658,148 A | 8/1997 | Neuberger et al. |
| 5,683,436 A | 11/1997 | Mendes et al. |
| 6,026,828 A | 2/2000 | Altshuler |
| 6,045,499 A | 4/2000 | Pitesky |
| 6,096,066 A | 8/2000 | Chen et al. |
| 6,171,332 B1 | 1/2001 | Whitehurst |
| 6,201,764 B1 | 3/2001 | Rice et al. |
| 6,211,626 B1 | 4/2001 | Lys et al. |
| 6,244,865 B1 | 6/2001 | Nelson et al. |
| 6,251,127 B1 | 6/2001 | Biel |
| 6,283,956 B1 | 9/2001 | McDaniel |
| 6,290,496 B1 | 9/2001 | Azar et al. |
| 6,290,713 B1 | 9/2001 | Russell |
| 6,379,376 B1 | 4/2002 | Lubart |
| 6,443,978 B1 | 9/2002 | Zharov |
| 6,462,070 B1 | 10/2002 | Hasan et al. |
| 6,471,716 B1 | 10/2002 | Pecukonis |
| 6,491,618 B1 | 12/2002 | Ganz |
| 6,497,719 B2 | 12/2002 | Pearl et al. |
| 6,551,346 B2 | 4/2003 | Crossley |
| 6,561,808 B2 | 5/2003 | Neuberger |
| 6,623,513 B2 | 9/2003 | Biel |
| 6,645,230 B2 | 11/2003 | Whitehurst |
| 6,663,659 B2 | 12/2003 | McDaniel |
| 6,676,655 B2 | 1/2004 | McDaniel |
| 6,887,260 B1 | 5/2005 | McDaniel |
| 6,890,346 B2 | 5/2005 | Ganz et al. |
| 6,902,397 B2 | 6/2005 | Farrell et al. |
| 6,918,922 B2 | 7/2005 | Oron |
| 6,936,044 B2 | 8/2005 | McDaniel |
| 6,955,684 B2 | 10/2005 | Savage, Jr. et al. |
| 6,977,075 B2 | 12/2005 | Hasan et al. |
| 6,989,023 B2 | 1/2006 | Black |
| 7,090,497 B1 | 8/2006 | Harris |
| 7,107,996 B2 | 9/2006 | Ganz et al. |
| 7,144,248 B2 | 12/2006 | Irwin |
| 7,159,590 B2 | 1/2007 | Rife |
| 7,201,764 B2 | 4/2007 | Pearl et al. |
| 7,201,765 B2 | 4/2007 | McDaniel |
| 7,223,270 B2 | 5/2007 | Altshuler et al. |
| 7,223,281 B2 | 5/2007 | Altshuler et al. |
| 7,226,470 B2 | 6/2007 | Kemeny et al. |
| 7,267,673 B2 | 9/2007 | Pilcher et al. |
| 7,303,578 B2 | 12/2007 | De Taboada et al. |
| 7,304,201 B2 | 12/2007 | Holloway et al. |
| 7,309,348 B2 | 12/2007 | Streeter et al. |
| 7,329,273 B2 | 2/2008 | Altshuler et al. |
| 7,329,274 B2 | 2/2008 | Altshuler et al. |
| 7,422,598 B2 | 9/2008 | Altshuler et al. |
| 7,435,252 B2 | 10/2008 | Krespi et al. |
| 7,467,946 B2 | 12/2008 | Rizoiu et al. |
| 7,494,503 B2 | 2/2009 | McDaniel |
| 7,544,204 B2 | 6/2009 | Krespi et al. |
| D599,954 S | 9/2009 | Michaels et al. |
| 7,763,058 B2 | 7/2010 | Sterenborg et al. |
| D631,604 S | 1/2011 | Michaels et al. |
| D635,686 S | 4/2011 | Tucker et al. |
| 7,918,229 B2 | 4/2011 | Cumbie et al. |
| 7,950,396 B2 | 5/2011 | Rose et al. |
| D639,751 S | 6/2011 | Tucker et al. |
| D640,793 S | 6/2011 | Britt |
| 8,021,148 B2 | 9/2011 | Goodson et al. |
| 8,021,405 B2 | 9/2011 | White |
| 8,025,686 B2 | 9/2011 | Morgan |
| 8,029,278 B1 | 10/2011 | Levine |
| 8,053,977 B2 | 11/2011 | Lifka et al. |
| 8,088,122 B2 | 1/2012 | Li et al. |
| 8,109,981 B2 | 2/2012 | Gertner et al. |
| 8,146,607 B2 | 4/2012 | Rabin et al. |
| 8,186,997 B2 | 5/2012 | Binner et al. |
| 8,192,473 B2 | 6/2012 | Tucker et al. |
| 8,214,958 B2 | 7/2012 | Pinyayev et al. |
| 8,240,312 B2 | 8/2012 | Feuerstein et al. |
| 8,252,033 B2 | 8/2012 | Tucker et al. |
| 8,398,264 B2 | 3/2013 | Anderson et al. |
| 8,435,273 B2 | 5/2013 | Lum et al. |
| 8,486,123 B2 | 7/2013 | Vizethum et al. |
| 8,518,029 B2 | 8/2013 | Birmingham et al. |
| 8,535,361 B2 | 9/2013 | Lim et al. |
| 8,556,951 B2 | 10/2013 | Witt et al. |
| 8,641,702 B2 | 2/2014 | Pilcher et al. |
| 8,651,111 B2 | 2/2014 | McDaniel |
| 8,668,727 B2 | 3/2014 | Natale et al. |
| 8,684,577 B2 | 4/2014 | Vayser |
| 8,685,466 B2 | 4/2014 | Piergallini et al. |
| 8,690,933 B2 | 4/2014 | Mitchell |
| 8,710,460 B2 | 4/2014 | Dayton |
| 8,721,696 B2 | 5/2014 | Krespi et al. |
| 8,747,446 B2 | 6/2014 | Chen et al. |
| 8,758,215 B2 | 6/2014 | Legendre et al. |
| 8,771,327 B2 | 7/2014 | Pearl et al. |
| 8,790,381 B2 | 7/2014 | Pierce |
| 8,815,931 B2 | 8/2014 | Grafe et al. |
| D712,561 S | 9/2014 | Hagenauer |
| 8,838,228 B2 | 9/2014 | Beisang, III et al. |
| 8,845,704 B2 | 9/2014 | Dunning et al. |
| D716,493 S | 10/2014 | Michaels et al. |
| 8,858,607 B1 | 10/2014 | Jones |
| 8,900,282 B2 | 12/2014 | Brawn |
| 8,900,283 B2 | 12/2014 | Johnson et al. |
| 8,940,775 B2 | 1/2015 | Fedele et al. |
| 9,017,391 B2 | 4/2015 | McDaniel |
| 9,039,966 B2 | 5/2015 | Anderson et al. |
| 9,040,103 B2 | 5/2015 | Marrot et al. |
| 9,095,704 B2 | 8/2015 | McGuire |
| 9,132,279 B2 | 9/2015 | Roersma et al. |
| 9,144,690 B2 | 9/2015 | McDaniel |
| 9,149,348 B2 | 10/2015 | Wu et al. |
| 9,162,001 B2 | 10/2015 | Sunkara et al. |
| 9,180,308 B1 | 11/2015 | Frost |
| 9,192,780 B2 | 11/2015 | McDaniel |
| 9,198,502 B2 | 12/2015 | Barnes et al. |
| 9,211,420 B2 | 12/2015 | Patel et al. |
| 9,215,921 B2 | 12/2015 | Thiebaut et al. |
| 9,227,082 B2 | 1/2016 | McDaniel |
| D754,897 S | 4/2016 | Michaels et al. |
| 9,308,389 B2 | 4/2016 | Brawn |
| 9,333,274 B2 | 5/2016 | Peterson et al. |
| 9,415,237 B2 | 8/2016 | Wagenaar Cacciola et al. |
| 9,439,989 B2 | 9/2016 | Lalicki et al. |
| 9,474,811 B2 | 10/2016 | Sharma |
| 9,504,752 B2 | 11/2016 | Kanno et al. |
| 9,504,847 B2 | 11/2016 | Pryor et al. |
| D777,339 S | 1/2017 | Chen |
| 9,545,524 B2 | 1/2017 | Maass et al. |
| 9,554,963 B2 | 1/2017 | Pilcher et al. |
| 9,561,077 B2 | 2/2017 | Alfano |
| 9,561,386 B2 | 2/2017 | Pearl et al. |
| 9,616,013 B2 | 4/2017 | Casasanta, III et al. |
| 9,636,522 B2 | 5/2017 | Oversluizen et al. |
| 9,700,641 B2 | 7/2017 | Hawkins et al. |
| 9,724,536 B1 | 8/2017 | Rabin et al. |
| 9,730,780 B2 | 8/2017 | Brawn et al. |
| 9,744,375 B2 | 8/2017 | Oberreiter et al. |
| D804,047 S | 11/2017 | Michaels et al. |
| 9,808,646 B2 | 11/2017 | Piergallini et al. |
| 9,808,647 B2 | 11/2017 | Rhodes et al. |
| 9,901,747 B2 | 2/2018 | Gamelin et al. |
| 9,907,976 B2 | 3/2018 | Bourke, Jr. et al. |
| 9,913,994 B2 | 3/2018 | Marchese et al. |
| 10,010,718 B2 | 7/2018 | Basiony |
| 10,220,221 B2 | 3/2019 | Wu |
| 10,258,442 B2 | 4/2019 | Snyder et al. |
| 10,272,262 B2 | 4/2019 | Bourke, Jr. et al. |

(56) References Cited

U.S. PATENT DOCUMENTS

| | | |
|---|---|---|
| 10,328,276 B2 | 6/2019 | Williams et al. |
| 10,357,661 B2 | 7/2019 | Hellstrom et al. |
| 10,406,379 B2 | 9/2019 | Sentis et al. |
| 10,416,366 B2 | 9/2019 | Rose et al. |
| 10,463,873 B1 | 11/2019 | Yang et al. |
| 10,525,275 B2 | 1/2020 | Stasko et al. |
| 10,561,854 B2 | 2/2020 | Kim et al. |
| 10,569,097 B2 | 2/2020 | Medendorp, Jr. et al. |
| 10,639,498 B2 | 5/2020 | Enwemeka et al. |
| 10,682,203 B2 | 6/2020 | Vazales |
| 10,729,524 B2 | 8/2020 | Brawn et al. |
| 10,780,189 B2 | 9/2020 | Randers-Pehrson et al. |
| 10,981,017 B2 | 4/2021 | Enwemeka et al. |
| 11,147,984 B2 | 10/2021 | Emerson et al. |
| 11,266,855 B2 | 3/2022 | Enwemeka et al. |
| 11,318,325 B2 | 5/2022 | Rezaie et al. |
| 2002/0029071 A1 | 3/2002 | Whitehurst |
| 2002/0128648 A1 | 9/2002 | Weber et al. |
| 2002/0135763 A1 | 9/2002 | MacKinnon et al. |
| 2002/0151941 A1 | 10/2002 | Okawa et al. |
| 2002/0173833 A1 | 11/2002 | Korman et al. |
| 2003/0009205 A1 | 1/2003 | Biel |
| 2003/0076281 A1 | 4/2003 | Morgan et al. |
| 2003/0130709 A1 | 7/2003 | D.C. et al. |
| 2003/0153825 A1 | 8/2003 | Mooradian et al. |
| 2003/0167080 A1 | 9/2003 | Hart et al. |
| 2003/0233138 A1 | 12/2003 | Spooner |
| 2003/0236487 A1 | 12/2003 | Knowlton |
| 2004/0032750 A1 | 2/2004 | Watts et al. |
| 2004/0044384 A1 | 3/2004 | Leber et al. |
| 2004/0052798 A1 | 3/2004 | Neuberger |
| 2004/0073079 A1 | 4/2004 | Altshuler et al. |
| 2004/0073278 A1 | 4/2004 | Pachys |
| 2004/0162596 A1 | 8/2004 | Altshuler et al. |
| 2004/0193235 A1 | 9/2004 | Altshuler et al. |
| 2004/0199227 A1 | 10/2004 | Altshuler et al. |
| 2005/0045189 A1 | 3/2005 | Jay |
| 2005/0055070 A1 | 3/2005 | Jones et al. |
| 2005/0059731 A1 | 3/2005 | Albrecht et al. |
| 2005/0064371 A1 | 3/2005 | Soukos et al. |
| 2005/0231983 A1 | 10/2005 | Dahm |
| 2005/0256553 A1 | 11/2005 | Strisower |
| 2006/0019220 A1 | 1/2006 | Loebel et al. |
| 2006/0085052 A1 | 4/2006 | Feuerstein et al. |
| 2006/0093561 A1 | 5/2006 | Kennedy |
| 2006/0167531 A1* | 7/2006 | Gertner ............... A61N 5/0603 607/86 |
| 2006/0183071 A1 | 8/2006 | Hsueh |
| 2006/0194164 A1 | 8/2006 | Altshuler et al. |
| 2006/0258896 A1 | 11/2006 | Haber et al. |
| 2006/0287696 A1 | 12/2006 | Wright et al. |
| 2007/0038272 A1 | 2/2007 | Liu |
| 2007/0060819 A1 | 3/2007 | Altshuler et al. |
| 2007/0099154 A1 | 5/2007 | Johnson |
| 2007/0105063 A1 | 5/2007 | Pinyayev et al. |
| 2007/0106856 A1 | 5/2007 | Nomura et al. |
| 2007/0135874 A1 | 6/2007 | Bala |
| 2007/0185553 A1 | 8/2007 | Kennedy |
| 2007/0208396 A1 | 9/2007 | Whatcott et al. |
| 2007/0213792 A1 | 9/2007 | Yaroslavsky et al. |
| 2007/0219600 A1 | 9/2007 | Gertner et al. |
| 2007/0233208 A1 | 10/2007 | Kurtz et al. |
| 2007/0259310 A1 | 11/2007 | Goodson et al. |
| 2007/0260231 A1 | 11/2007 | Rose et al. |
| 2008/0021370 A1 | 1/2008 | Bornstein |
| 2008/0032252 A1 | 2/2008 | Hayman et al. |
| 2008/0033516 A1 | 2/2008 | Altshuler et al. |
| 2008/0038685 A1 | 2/2008 | Sakaguchi et al. |
| 2008/0065175 A1 | 3/2008 | Redmond et al. |
| 2008/0096156 A1 | 4/2008 | Rose et al. |
| 2008/0097414 A1 | 4/2008 | Li et al. |
| 2008/0145813 A1 | 6/2008 | Crohn |
| 2008/0161748 A1 | 7/2008 | Tolkoff et al. |
| 2008/0210233 A1 | 9/2008 | McCarthy |
| 2008/0214530 A1 | 9/2008 | Colles |
| 2008/0245371 A1 | 10/2008 | Gruber |
| 2008/0254405 A1 | 10/2008 | Montgomery et al. |
| 2008/0269849 A1 | 10/2008 | Lewis |
| 2008/0280260 A1 | 11/2008 | Belikov et al. |
| 2008/0319430 A1 | 12/2008 | Zenzie et al. |
| 2009/0035725 A1 | 2/2009 | Loebel et al. |
| 2009/0093865 A1 | 4/2009 | Krespi et al. |
| 2009/0132011 A1 | 5/2009 | Altshuler et al. |
| 2009/0143842 A1 | 6/2009 | Cumbie et al. |
| 2009/0148808 A1 | 6/2009 | Alexander et al. |
| 2009/0254156 A1 | 10/2009 | Powell et al. |
| 2009/0318802 A1 | 12/2009 | Boyden et al. |
| 2009/0323370 A1 | 12/2009 | Koo |
| 2010/0004645 A1 | 1/2010 | Jeong et al. |
| 2010/0042040 A1 | 2/2010 | Arentz |
| 2010/0049180 A1 | 2/2010 | Wells et al. |
| 2010/0063565 A1 | 3/2010 | Beerwerth et al. |
| 2010/0076526 A1 | 3/2010 | Krespi et al. |
| 2010/0076529 A1 | 3/2010 | Tucker et al. |
| 2010/0106077 A1 | 4/2010 | Rabin et al. |
| 2010/0121131 A1 | 5/2010 | Mathes |
| 2010/0136646 A1 | 6/2010 | Tsen et al. |
| 2010/0160838 A1 | 6/2010 | Krespi |
| 2010/0204762 A1 | 8/2010 | De Taboada et al. |
| 2010/0222852 A1 | 9/2010 | Vasily et al. |
| 2010/0242155 A1 | 9/2010 | Carullo, Jr. |
| 2010/0286673 A1 | 11/2010 | Altshuler et al. |
| 2010/0331928 A1 | 12/2010 | Dunning et al. |
| 2011/0015707 A1 | 1/2011 | Tucker et al. |
| 2011/0020173 A1 | 1/2011 | Pryor et al. |
| 2011/0054573 A1 | 3/2011 | Mitchell |
| 2011/0054574 A1 | 3/2011 | Felix |
| 2011/0125229 A1 | 5/2011 | Lytle et al. |
| 2011/0144410 A1 | 6/2011 | Kennedy |
| 2011/0144727 A1 | 6/2011 | Benedict |
| 2011/0160814 A2 | 6/2011 | Tucker et al. |
| 2011/0162155 A1 | 7/2011 | Wai |
| 2011/0215261 A1 | 9/2011 | Lyslo et al. |
| 2011/0264174 A1 | 10/2011 | McNeill et al. |
| 2011/0301673 A1 | 12/2011 | Hoffer et al. |
| 2012/0045738 A1 | 2/2012 | Ho et al. |
| 2012/0059440 A1 | 3/2012 | Hamid |
| 2012/0065709 A1 | 3/2012 | Dunning et al. |
| 2012/0088204 A1 | 4/2012 | Ho et al. |
| 2012/0096657 A1 | 4/2012 | So et al. |
| 2012/0126134 A1 | 5/2012 | Deal et al. |
| 2012/0191162 A1 | 7/2012 | Villa |
| 2012/0209359 A1* | 8/2012 | Chen ..................... A61B 5/411 607/92 |
| 2012/0215292 A1 | 8/2012 | Gustavsson |
| 2012/0223216 A1 | 9/2012 | Flaherty et al. |
| 2012/0263625 A1 | 10/2012 | Aicher et al. |
| 2012/0270183 A1 | 10/2012 | Patel et al. |
| 2012/0310307 A1 | 12/2012 | Zhou |
| 2012/0322018 A1 | 12/2012 | Lowe et al. |
| 2013/0041432 A1 | 2/2013 | Tucker et al. |
| 2013/0131762 A1 | 5/2013 | Oversluizen et al. |
| 2013/0144364 A1 | 6/2013 | Wagenaar Cacciola et al. |
| 2013/0158358 A1 | 6/2013 | Holland |
| 2013/0172959 A1 | 7/2013 | Azoulay |
| 2013/0196284 A1 | 8/2013 | Brawn |
| 2013/0197495 A1 | 8/2013 | Koifman et al. |
| 2013/0245417 A1 | 9/2013 | Spector |
| 2013/0280671 A1 | 10/2013 | Brawn et al. |
| 2014/0023983 A1 | 1/2014 | Lowe et al. |
| 2014/0067024 A1 | 3/2014 | Jones et al. |
| 2014/0128941 A1 | 5/2014 | Williams |
| 2014/0128942 A1 | 5/2014 | Bembridge et al. |
| 2014/0148879 A1 | 5/2014 | Mersch |
| 2014/0163218 A1 | 6/2014 | Dei et al. |
| 2014/0171926 A1 | 6/2014 | Depfenhart |
| 2014/0243933 A1 | 8/2014 | Ginggen |
| 2014/0267662 A1 | 9/2014 | Lampo |
| 2014/0276247 A1 | 9/2014 | Hall et al. |
| 2014/0276248 A1 | 9/2014 | Hall et al. |
| 2014/0296524 A1 | 10/2014 | Jones et al. |
| 2014/0303693 A1 | 10/2014 | Haarlander et al. |
| 2014/0323946 A1 | 10/2014 | Bourke, Jr. et al. |
| 2014/0350643 A1 | 11/2014 | Pepitone et al. |

(56) References Cited

U.S. PATENT DOCUMENTS

| | | |
|---|---|---|
| 2015/0005854 A1 | 1/2015 | Said |
| 2015/0030989 A1 | 1/2015 | Soukos et al. |
| 2015/0045720 A1 | 2/2015 | Kanno et al. |
| 2015/0112411 A1 | 4/2015 | Beckman et al. |
| 2015/0164618 A1 | 6/2015 | Heacock et al. |
| 2015/0217130 A1 | 8/2015 | Gross et al. |
| 2015/0297914 A1 | 10/2015 | Hamid et al. |
| 2016/0000214 A1 | 1/2016 | Kim |
| 2016/0015840 A1 | 1/2016 | Gordon |
| 2016/0039854 A1 | 2/2016 | McFarland |
| 2016/0051835 A1 | 2/2016 | Tapper et al. |
| 2016/0059031 A1 | 3/2016 | Wescott et al. |
| 2016/0106999 A1 | 4/2016 | Michaels et al. |
| 2016/0114185 A1 | 4/2016 | Mankin |
| 2016/0129278 A1 | 5/2016 | Mayer |
| 2016/0151639 A1 | 6/2016 | Scharf et al. |
| 2016/0271415 A1 | 9/2016 | Min |
| 2016/0271420 A1 | 9/2016 | Pina |
| 2016/0317832 A1 | 11/2016 | Barneck et al. |
| 2017/0027432 A1 | 2/2017 | Wachs |
| 2017/0028215 A1 | 2/2017 | Medendorp, Jr. et al. |
| 2017/0028216 A1 | 2/2017 | Medendorp, Jr. et al. |
| 2017/0165499 A1 | 6/2017 | Blanche et al. |
| 2017/0173358 A1 | 6/2017 | Demarest et al. |
| 2017/0203132 A1 | 7/2017 | Luttrull et al. |
| 2017/0224206 A1 | 8/2017 | Vayser |
| 2017/0225011 A1 | 8/2017 | Frost |
| 2017/0290648 A1 | 10/2017 | Kuo |
| 2017/0333728 A1 | 11/2017 | Sentis et al. |
| 2017/0340898 A1* | 11/2017 | Moor ............... A61N 5/0624 |
| 2018/0008847 A1 | 1/2018 | Key |
| 2018/0014777 A1 | 1/2018 | Amir et al. |
| 2018/0036554 A1 | 2/2018 | Krespi |
| 2018/0111003 A1 | 4/2018 | Hewitson |
| 2018/0117355 A1 | 5/2018 | Loupis et al. |
| 2018/0146520 A1 | 5/2018 | Williams |
| 2018/0178027 A1* | 6/2018 | Shang ................. A61N 5/062 |
| 2018/0256916 A1 | 9/2018 | Kothari et al. |
| 2018/0264282 A1 | 9/2018 | Bornstein |
| 2018/0289940 A1 | 10/2018 | Spotnitz et al. |
| 2019/0014901 A1 | 1/2019 | Xi et al. |
| 2019/0124888 A1 | 5/2019 | Coyle |
| 2019/0134419 A1 | 5/2019 | Bourke, Jr. et al. |
| 2019/0142516 A1 | 5/2019 | Boutoussov et al. |
| 2019/0175938 A1 | 6/2019 | Rezaie et al. |
| 2019/0201711 A1 | 7/2019 | Brawn et al. |
| 2019/0209857 A1 | 7/2019 | Brawn et al. |
| 2020/0101315 A1 | 4/2020 | Reinhardt |
| 2020/0114171 A1 | 4/2020 | Tortora |
| 2020/0155350 A1 | 5/2020 | Neev |
| 2020/0222714 A1 | 7/2020 | Stasko et al. |
| 2020/0298014 A1 | 9/2020 | Stasko et al. |
| 2020/0298016 A1 | 9/2020 | Yoon et al. |
| 2020/0330186 A1 | 10/2020 | Barros et al. |
| 2020/0353112 A1 | 11/2020 | Randers-Pehrson et al. |
| 2020/0360124 A1 | 11/2020 | Woo et al. |
| 2021/0008384 A1 | 1/2021 | Lee |
| 2021/0128935 A1 | 5/2021 | Stasko et al. |
| 2021/0128936 A1 | 5/2021 | Stasko et al. |
| 2021/0128937 A1 | 5/2021 | Stasko et al. |
| 2021/0128938 A1 | 5/2021 | Stasko et al. |
| 2021/0138259 A1 | 5/2021 | Stasko et al. |
| 2021/0138260 A1 | 5/2021 | Park et al. |
| 2021/0196977 A1 | 7/2021 | Zhang |
| 2021/0228900 A1 | 7/2021 | Kothari et al. |
| 2021/0260398 A1 | 8/2021 | Bilston et al. |
| 2021/0267738 A1 | 9/2021 | Mackie |
| 2021/0283490 A1 | 9/2021 | Lin |
| 2021/0290970 A1 | 9/2021 | Hunter et al. |
| 2021/0290971 A1 | 9/2021 | Cockrell et al. |
| 2021/0290975 A1 | 9/2021 | Hunter et al. |
| 2021/0346500 A1 | 11/2021 | Schikora |
| 2021/0379400 A1 | 12/2021 | Emerson et al. |
| 2021/0402212 A1 | 12/2021 | Schupp et al. |
| 2022/0023660 A1 | 1/2022 | Emerson et al. |
| 2022/0040495 A1 | 2/2022 | Hwang et al. |
| 2022/0088409 A1 | 3/2022 | Dombrowski et al. |
| 2022/0189342 A1 | 6/2022 | Emerson et al. |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 102731405 A | 10/2012 |
| CN | 102802694 A | 11/2012 |
| CN | 103143015 A | 6/2013 |
| CN | 203169848 U | 9/2013 |
| CN | 103601727 A | 2/2014 |
| CN | 103610464 A | 3/2014 |
| CN | 103724356 A | 4/2014 |
| CN | 103930162 A | 7/2014 |
| CN | 104667432 A | 6/2015 |
| DE | 102010010763 A1 | 9/2011 |
| DE | 102013202122 A1 | 6/2014 |
| DE | 102012224183 A1 | 7/2014 |
| EP | 2368598 A1 | 9/2011 |
| EP | 2508229 A1 | 10/2012 |
| EP | 3069762 A1 | 9/2016 |
| EP | 3108931 A1 | 12/2016 |
| GB | 2499921 A | 9/2013 |
| KR | 20100124083 A | 11/2010 |
| KR | 20120090317 A | 8/2012 |
| KR | 101349157 B1 | 1/2014 |
| KR | 20140014689 A | 2/2014 |
| WO | 1995010243 A1 | 4/1995 |
| WO | 2004033040 A1 | 4/2004 |
| WO | 2004084752 A2 | 10/2004 |
| WO | 2006047868 A1 | 5/2006 |
| WO | 2006063318 A1 | 6/2006 |
| WO | 2006130340 A2 | 12/2006 |
| WO | 2008024414 A1 | 2/2008 |
| WO | 2008041296 A1 | 4/2008 |
| WO | 2008051918 A2 | 5/2008 |
| WO | 2008066943 A2 | 6/2008 |
| WO | 2008131343 A1 | 10/2008 |
| WO | 2008144157 A1 | 11/2008 |
| WO | 2009047669 A2 | 4/2009 |
| WO | 2010098761 A1 | 9/2010 |
| WO | 2011083378 A1 | 7/2011 |
| WO | 2011083381 A1 | 7/2011 |
| WO | 2012001194 A1 | 1/2012 |
| WO | 2013036558 A1 | 3/2013 |
| WO | 2014021557 A1 | 2/2014 |
| WO | 2014089552 A1 | 6/2014 |
| WO | 2014116659 A1 | 7/2014 |
| WO | 2014136255 A1 | 9/2014 |
| WO | 2014146029 A1 | 9/2014 |
| WO | 2015006309 A1 | 1/2015 |
| WO | 2015134204 A1 | 9/2015 |
| WO | 2016039812 A1 | 3/2016 |
| WO | 2016078603 A1 | 5/2016 |
| WO | 2016081594 A1 | 5/2016 |
| WO | 2016116859 A1 | 7/2016 |
| WO | 2016178472 A1 | 11/2016 |
| WO | 2017019836 A1 | 2/2017 |
| WO | 2017044931 A1 | 3/2017 |
| WO | 2017070155 A1 | 4/2017 |
| WO | 2018026892 A1 | 2/2018 |
| WO | 2019022275 A1 | 1/2019 |
| WO | 2019127427 A1 | 7/2019 |
| WO | 2019145519 A1 | 8/2019 |
| WO | 2019156921 A1 | 8/2019 |
| WO | 2019191820 A1 | 10/2019 |
| WO | 2019234308 A1 | 12/2019 |
| WO | 2020047659 A1 | 3/2020 |
| WO | 2020081910 A1 | 4/2020 |

OTHER PUBLICATIONS

Examination Report for Australian Patent Application No. 2021239894, dated Nov. 9, 2021, 3 pages.

(56) References Cited

OTHER PUBLICATIONS

First Office Action for Chinese Patent Application No. 202010561507.X, dated Oct. 19, 2021, 54 pages.
Non-Final Office Action for U.S. Appl. No. 17/410,154, dated Nov. 8, 2021, 16 pages.
Final Office Action for U.S. Appl. No. 17/410,154, dated Dec. 22, 2021, 15 pages.
Zein, Randa, et al., "Review of light parameters and photobiomodulation efficacy: dive into complexity," Journal of Biomedical Optics, vol. 23, Issue 12, Dec. 2018, 17 pages.
Zupin, Luisa, et al., "Antiviral properties of blue laser in an in vitro model of HSV-1 infection," Microbial Immunal, Letter to the Editor, vol. 62, 2018, pp. 477-479.
Zupin, Luisa, et al., "Photobiomodulation therapy reduces viral load and cell death in ZIKV-infected glioblastoma cell line," Lasers in Medical Science, vol. 33, Jul. 2018, Springer Nature, pp. 2011-2013.
International Search Report and Written Opinion for PCT/US2016/044400, dated Oct. 4, 2016, 8 pages.
International Preliminary Report on Patentability for PCT/US2016/044400, dated Feb. 8, 2018, 7 pages.
Non-Final Office Action for U.S. Appl. No. 15/222,199, dated Jan. 11, 2019, 9 pages.
Non-Final Office Action for U.S. Appl. No. 15/222,243, dated Jan. 11, 2019, 10 pages.
International Preliminary Report on Patentability for PCT/US2016/044403, dated Feb. 8, 2018, 7 pages.
Final Office Action for U.S. Appl. No. 15/222,199, dated Jul. 29, 2019, 9 pages.
Notice of Allowance and Applicant-Initiated Interview Summary for U.S. Appl. No. 15/222,199, dated Sep. 18, 2019, 11 pages.
Final Office Action for U.S. Appl. No. 15/222,243, dated Jul. 29, 2019, 12 pages.
Notice of Allowance and Applicant-Initiated Interview Summary for U.S. Appl. No. 15/222,243, dated Dec. 19, 2019, 11 pages.
Non-Final Office Action for U.S. Appl. No. 16/709,550, dated Apr. 30, 2020, 13 pages.
Hamblin, Michael, "Mechanisms of Low Level Light Therapy," Aug. 14, 2008, 22 pages, photobiology.info/Hamblin.html.
Hamblin, Michael R., "The Role of Nitric Oxide in Low Level Light Therapy," Proceedings of SPIE, vol. 6846,2008, pp. 684602-1 to 684602-14.
Hessling, Martin, et al., "Selection of parameters for thermal coronavirus inactivation—a data-based recommendation," GMS Hygiene and Infection Control, vol. 15, 2020, 7 pages.
Horby, Peter, et al., "Dexamethasone in Hospitalized Patients with Covid-19—Preliminary Report," New England Journal of Medicine, Jul. 17, 2020, 11 pages.
Jackson, George, et al., "Prevalidation of an Acute Inhalation Toxicity Test Using the EpiAirway In Vitro Human Airway Model," Applied In Vitro Toxicology, vol. 4, Issue 2, 2018, Mary Ann Liebert, Inc., pp. 149-158.
Jensen, Caleb, et al., "Is it Time to Start Transitioning From 2D to 3D Cell Culture," Frontiers in Molecular Biosciences, Review, vol. 7, Mar. 2020, 15 pages.
Jin, Jin, et al., "Noncanonical NF-KB Pathway Controls the Production of Type I Interferons in Antiviral Innate Immunity," Immunity, vol. 40, Mar. 2014, Elsevier Inc., pp. 342-354.
Karu, Tiina I., "Low-Power Laser Therapy," Biomedical Photonics Handbook, Chapter 48, CRC Press, 2003, pp. 48-1 to 48-25.
Kelm, Malte, "Nitric oxide metabolism and breakdown," Review, Biochimica et Biophysica Acta, vol. 1411, 1999, Elsevier Science B.V., pp. 273-289.
Kingsley, David, et al., "Oxygen-dependent laser inactivation of murine norovirus using visible light lasers," Virology Journal, Jul. 31, 2018, 8 pages.
Kirima, Kazuyoshi et al., "Evaluation of systemic blood NO dynamics by EPR spectroscopy: HbNO as an endogenous index of NO," American Journal of Physiology Heart and Circulatory Physiology, vol. 285, No. 2, Aug. 2003, pp. H589-H596.
Kitchel, Elaine, "The Effects of Blue Light on Ocular Health," Journal of Visual Impairment and Blindness, Jun. 2000, AFB, pp. 399-403.
Klein, Eili, et al., "The frequency of influenza and bacterial coinfection: a systematic review and meta-analysis," influenza and Other Respiratory Viruses, vol. 10, Issue 5, May 2016, John Wiley & Sons Ltd., pp. 394-403.
Kovacs, Izabella et al., "Nitric oxide-based protein modification: formation and site-specificity of protein S-nitrosylation," Frontiers in Plant Science, vol. 4, Article 137, May 14, 2013, 10 pages.
Leong, Mimi, "Effects of Light-Emitting Diode Photostimulation On Burn Wound Healing," Thesis, The University of Texas Graduate School of Biomedical Sciences at Galveston, May 2006, 92 pages.
Li, Jie, et al., "Involvement of the Toll-Like Receptor/Nitric Oxide Signaling Pathway in the Pathogenesis of Cervical Cancer Caused by High-Risk Human Papillomavirus Infection," Biomed Research International, 2017, Hindawi, 9 pages.
Lubart, et al., "A Possible Mechanism for the Bactericidal Effect of Visible Light," Review Article, Laser Therapy, vol. 20, 2011, pp. 17-22.
Mandel, Arkady, et al., "A renaissance in low-level laser (light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Marullo, Rosella, et al., "HPV16 E6 and E7 proteins induce a chronic oxidative stress response via NOX2 that causes genomic instability and increased susceptibility to DNA damage in head and neck cancer cells," Carcinogenesis, vol. 36, Issue 11, 2015, Oxford University Press, pp. 1397-1406.
Moseley, Harry, et al., "Population reference intervals for minimal erythemal doses in monochromator phototesting," Photodermatology, Photoimmunology & Photomedicine, vol. 25, 2009, pp. 8-11.
Narita, Kouji, et al., "Chronic irradiation with 222-nm UVC light induces neither DNA damage nor epidermal lesions In mouse skin, even at high doses," Research Article, PLOS One, doi.org/10.1371/journal.pone.0201259, Jul. 25, 2018, 9 pages.
Narita, Kouji, et al., "Disinfection and healing effects of 222-nm UVC light on methicillin-resistant *Staphylococcus aureus* infection in mouse wounds," Dissertation, Hirosaki University Graduate School of Medicine, 2017, Elsevier, 36 pages.
Narita, Kouji, et al., "Ultraviolet C light with wavelength of 222 nm inactivates a wide spectrum of microbial pathogens," Journal of Hospital Infection, vol. 105, Mar. 31, 2020, Elsevier Ltd., pp. 459-467.
Perdiz, Daniel, et al., "Distribution and Repair of Bipyrimidine Photoproducts in Solar UV-irradiated Mammalian Cells," Journal of Biological Chemistry, vol. 275, Issue 35, Sep. 2000, pp. 26732-26742.
Pfeifer, Gerd, et al., "UV wavelength-dependent DNA damage and human non-melanoma and melanoma skin cancer," Author Manuscript, Journal of Photochemistry and Photobiology, vol. 11, Issue 1, Jan. 2012, 14 pages.
Phurrough, Steve et al., "Decision Memo for Infrared Therapy Devices (CAG-00291N)," Centers for Medicare & Medicaid Services, Oct. 24, 2006, 37 pages.
Poyton, Robert O. et al., "Therapeutic Photobiomodulation: Nitric Oxide and a Novel Function of Mitochondrial Cytochrome C Oxidase," Discovery Medicine, Feb. 20, 2011, 11 pages.
Ramakrishnan, Praveen, et al., "Cytotoxic responses to 405 nm light exposure in mammalian and bacterial cells: Involvement of reactive oxygen species," Toxicology in Vitro, vol. 33, Feb. 2016, Elsevier B.V., pp. 54-62.
Ravanant, Jean-Luc, et al., "Direct and indirect effects of UV radiation on DNA and its components," Journal of Photochemistry and Photobiology, vol. 63, 2001, pp. 88-102.
Richardson, Tobias, et al., "Inactivation of murine leukaemia virus by exposure to visible light," Virology, vol. 341, 2005, Elsevier Inc., pp. 321-329.

(56) References Cited

OTHER PUBLICATIONS

Sabino, Caetano, et al., "Light-based technologies for management of COVID-19 pandemic crisis," Journal of Photochemistry and Photobiology, Aug. 2020, Elsevier B.V., 8 pages.

Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.

Saura, Marta, et al., "An Antiviral Mechanism of Nitric Oxide: Inhibition of a Viral Protease," Immunity, vol. 10, Jan. 1999, Cell Press, 8 pages.

Serrage, Hannah, et al., "Under the spotlight: mechanisms of photobiomodulation concentrating on blue and green light," Photochemical and Photobiological Sciences, Jun. 2019, 43 pages.

St. Denis, Tyler, et al., "Killing Bacterial Spores with Blue Light: When Innate Resistance Meets the Power of Light," Photochemistry and Photobiology, vol. 89, Issue 1, Sep. 2012, Wiley Preiodicals, Inc., 7 pages.

Tomb, Rachael, et al., "Inactivation of Streptomyces phage φC31 by 405 nm light," Bacteriophage, vol. 4, Jul. 2014, Landes Bioscience, 7 pages.

Tomb, Rachael, et al., "New Proof-of-Concept in Viral Inactivation: Virucidal Efficacy of 405 nm Light Against Feline Calicivirus as a Model for Norovirus Decontamination," Food Environ Virol, Dec. 2016, pp. 159-167.

Tomoroni, et al., "A Novel Laser Fiberscope for Simultaneous Imaging and Phototherapy of Peripheral Lung Cancer," Chest, vol. 156, Issue 3, Sep. 2019, 8 pages.

Tsen, KT, et al., "Inactivation of viruses by coherent excitations with a low power visible femtosecond laser," Virology Journal, Jun. 2007, BioMed Central Ltd., 5 pages.

Tsen, SHAW-WEI, et al., "Chemical-free inactivated whole influenza virus vaccine prepared by ultrashort pulsed laser treatment," Journal of Biomedical Optics, vol. 20, Issue 5, May 2015, 8 pages.

Tsen, Shaw-Wei, et al., "Inactivation of enveloped virus by laser-driven protein aggregation," Journal of Biomedical Optics, vol. 17, Issue 12, Dec. 2012, 8 pages.

Tsen, Shaw-Wei, "Pathogen Reduction in Human Plasma Using an Ultrashort Pulsed Laser," PLOS One, vol. 9, Issue 11, Nov. 2014, 8 pages.

Tsen, Shaw-Wei, et al., "Prospects for a novel ultrashort pulsed laser technology for pathogen inactivation," Journal of Biomedical Science, Jul. 2012, 11 pages.

Tsen, Shaw-Wei, et al., "Studies of inactivation mechanism of non-enveloped icosahedral virus by a visible ultrashort pulsed laser," Virology Journal, vol. 11, Issue 20, Feb. 2014, BioMed Central Ltd., 9 pages.

Vatansever, Fatma, et al., "Antimicrobial strategies centered around reactive oxygen species—bactericidal antibiotics, photodynamic therapy, and beyond," FEMS Microbiology Reviews, vol. 37, Issue 6, 2013, pp. 955-989.

Wei, Xue-Min, et al., "Relationship between nitric oxide in cervical microenvironment and different HPV types and effect on cervical cancer cells," Zhonghua Fu Chan Ke Za Zhi, vol. 46, Issue 4, Apr. 2011, pp. 260-265 (Abstract Only).

Williams, Vonetta, et al., "Human Papillomavirus Type 16 E6* Induces Oxidative Stress and DNA Damage," Journal of Virology, vol. 88, Issue 12, Jun. 2014, pp. 6751-6761.

Willoughby, Jamin, "Predicting Respiratory Toxicity Using a Human 3D Airway (EpiAirway) Model Combined with Multiple Parametric Analysis," Applied In Vitro Toxicology, vol. 1, Issue 1, 2015, pp. 55-65.

Wolf, Yuri, et al., "Origins and Evolution of the Global RNA Virome," mBio, vol. 9, Issue 6, Nov. 2018, 31 pages.

Abeyakirthi, Sharnika, "Nitric oxide," DermNet NZ, 2009, 4 pages, www.dermnetnz.org/topics/nitric-oxide/.

Adamskaya, Natalia et al., "Light therapy by blue LED improves wound healing in an excision model in rats," Injury, 2010, 5 pages.

Adusumilli, Nagasai, et al., "Harnessing nitric oxide for preventing, limiting and treating the severe pulmonary consequences of COVID-19," Nitric Oxide, vol. 103, Jul. 2020, Elsevier Inc., 5 pages.

Akerstrom, Sara, et al., "Nitric Oxide Inhibits the Replication Cycle of Severe Acute Respiratory Syndrome Coronavirus," Journal of Virology, vol. 79, Issue 3, Feb. 2005, pp. 1966-1969.

Akerstrom, Sara, et al., "Dual effect of nitric oxide on SARS-CoV replication: Viral RNA production and palmitoylation of the S protein are affected," Virology, vol. 395, Oct. 2009, Elsevier Inc., 9 pages.

Andrew, Penelope J. et al., "Enzymatic function of nitric oxide synthases," Cardiovascular Research, vol. 43, No. 3, Aug. 15, 1999, pp. 521-531.

Author Unknown, "Brilliant Light Therapy," In Light Wellness Systems, eBrochure, Date Unknown, 5 pages.

Author Unkown, "dpl Oral Care—For Healthy Teeth & Gums," Product Brief, Revive Light Therapy, revivelighttherapy.com/product/dpl-oral-care-light-therapy-system-teeth-whitening/, accessed Jan. 31, 2021, 5 pages.

Author Unknown, "Healed by Light," Digi-Key Electronics, Jul. 1, 2014, 4 pages, www.digikey.com/es/articles/techzone/2014/jul/healed-by-light.

Author Unknown, "illuMask," La Lumière, Date Unknown, 2 pages, http://www.illumask.com/dimming/.

Author Unknown, "IPL Hair Removal," Spectrum Science & Beauty, Spectrum Blog, Sep. 16, 2014, 3 pages, www.spectrumsciencebeauty.com.au/ipl-hair-removal/#prettyPhoto.

Author Unknown, "Near-IR Photoluminescent Dyes for Molecular Labeling," NanoQuantum, Technology, 2013, 7 pages, www.nanoquantum.com/Technology.html.

Author Unknown, "Philips Blue Touch," Koninklijke Philips N.V., Version 1.0.1, Sep. 1, 2013, 2 pages.

Author Unknown, "Safety and Efficacy of UVC to Fight Covid-19," Gilbert W. Beebe Webinar Series, Program Agenda, Sep. 16, 2020, 6 pages.

Author Unknown, "Theradome Laser Helmet Review—A 120 Day Continuous Journal," Prevent Hair Loss Products, Jan. 14, 2014, retrieved Jun. 27, 2017, web.archive.org/web/20140610024017/http://preventhairlossproducts.com:80/theradome-laser-helmet-review-120-day-continuous-journal/, pp. 1-4.

Author Unknown, "Ultraviolet Light Therapy," Wound Care Centers, Date Unknown, 3 pages, www.woundcarecenters.org/article/wound-therapies/ultraviolet-light-therapy.

Author Unknown, "Vio Orb—Antimicrobial Light Ball," Product Brief, Revive Light Therapy, revivelighttherapy.com/product/envirohygiene-orb-antimicrobial-light-ball/, accessed Jan. 31, 2021, 6 pages.

Author Unknown, "What is Light Therapy used for?" Rio, The Dezac Group, Ltd, Date Unknown, 4 pages, www.lightmask.com/uses_for_it.htm#top.

Avci, Pinar et al., "Low-Level Laser (Light) Therapy (LLLT) for Treatment of Hair Loss," Lasers in Surgery and Medicine, vol. 46, 2014, pp. 144-151.

Avci, Pinar et al., "Low-Level Laser (Light) Therapy (LLLT) in Skin: Stimulating, Healing, Restoring," Seminars in Cutaneous Medicine and Surgery, vol. 32, No. 1, 2013, pp. 41-52.

Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.

Barolet, Daniel, "Light-Emitting Diodes (LEDs) in Dermatology," Seminars in Cutaneous Medicine and Surgery, vol. 27, No. 4, Dec. 1, 2008, pp. 227-238.

Bashkatov et al., "Optical properties of human skin, subcutaneous and mucous tissues in the wavelength range from 400-2000 nm," Journal of Physics D: Applied Physics, vol. 38, Jul. 2005, IOP Publishing Ltd, pp. 2543-2555.

Beck, Sara, et al., "Comparison of UV-Induced Inactivation and RNA Damage in MS2 Phage across the Germicidal UV Spectrum," Applied and Environmental Microbiology, vol. 82, Issue 5, Mar. 2016, pp. 1468-1474.

(56) References Cited

OTHER PUBLICATIONS

Beigel, JH, et al., "Remdesivir for the Treatment of Covid-19—Final Report," New England Journal of Medicine, vol. 383, Issue 19, Nov. 5, 2020, pp. 1813-1826.
Besaratinia, Ahmad, et al., "DNA lesions induced by UV A1 and B radiation in human cells: Comparative analyses in the overall genome and in the p53 tumor suppressor gene," PNAS, vol. 102, Issue 29, Jul. 2005, pp. 10058-10063.
Buonnano, Manuela, et al., "Far-UVC light (222 nm) efficiently and safely inactivates airborne human coronaviruses," Scientific Reports, Jun. 24, 2020, 8 pages.
Buonnano, Manuela, et al., "Germicidal Efficacy and Mammalian Skin Safety of 222-nm UV Light," Radiation Research, vol. 187, 2017, Radiation Research Society, 2017, pp. 493-501.
Cals-Grierson, M.-M. et al., "Nitric oxide function in the skin," Nitric Oxide, vol. 10, No. 4, Jun. 2004, pp. 179-193.
Chaves, Maria Emília De Abreu et al., "Effects of low-power light therapy on wound healing: LASER x LED," Anais Brasileiros de Dermatologia, vol. 89, No. 4, Jul./Aug. 2014, pp. 616-623.
Chen, Luni, et al., "Inhalation of Nitric Oxide in the Treatment of Severe Acute Respiratory Syndrome: A Rescue Trial in Beijing," Brief Report, Clinical Infectious Diseases, vol. 39, Oct. 2004, pp. 1531-1535.
Creagh-Brown, Benedict, et al., "Bench-to-bedside review: Inhaled nitric oxide therapy in adults," Critical Care, vol. 13, Issue 3, May 2009, BioMed Central Ltd, 8 pages.
Dai, Tianhong, et al., "Blue light for infectious diseases: Propionibacterium acnes, Helicobacter pylori, and beyond?," NIH-PA, Author Manuscript, 2012, Elsevier Ltd., 31 pages.
Darnelll, Miriam, et al., "Evaluation of inactivation methods for severe acute respiratory syndrome coronavirus in noncellular blood products," Transfusion, vol. 46, Oct. 2006, 8 pages.
De Marco, Federico, "Oxidative Stress and HPV Carcinogenesis," Viruses, vol. 5, Feb. 2013, pp. 708-731.
Donnarumma, G., et al., "Inhibition of HSV-1 Replication by Laser Diode-Irradiation: Possible Mechanism of Action," Journal of Immunopathology and Pharmacology, vol. 23, Issue 4, 2010, Biolife, pp. 1167-1176.
Dorrington, Michael, et al., "NF-KB Signaling in Macrophages: Dynamics, Crosstalk, and Signal Integration," Frontiers in Immunology, vol. 10, Apr. 9, 2019, 12 pages.
Eadie, Ewan, et al., "Extreme Exposure to Filtered Far-UVC: A Case Study," Ninewells Hospital and Medical School, Sep. 25, 2020, 14 pages.
Enwemeka, Chukuka, et al., "Blue 470-nm Light Kills Methicillin-Resistant *Staphylococcus aureus* (MRSA) in Vitro," Photomedicine and Laser Surgery, vol. 27, Issue 2, 2009, 6 pages.
Enwemeka, Chukuka, et al., "Light as a potential treatment for pandemic coronavirus infections: A perspective," Journal of Photochemistry & Photobiology, B: Biology, vol. 207, May 2020, 7 pages.
Enwemeka, Chukuka, et al., "Visible 405 nm SLD Light Photo-Destroys Methicillin-Resistant *Staphylococcus aureus* (MRSA) In Vitro," Lasers in Surgery and Medicine, vol. 40, 2008, pp. 734-737.
Farivar, Shirin et al., "Biological Effects of Low Level Laser Therapy," Journal of Lasers in Medical Sciences, vol. 5, No. 2, Spring 2014, pp. 58-62.
Feelisch, Martin et al., "Concomitant S-, N-, and heme-nitrosis(yl)ation in biological tissues and fluids: implications for the fate of NO in vivo," FASEB, vol. 16, No. 13, Nov. 2002, pp. 1775-1785.
Ferrari-Light, Dana, et al., "The Utility of Near-Infrared Fluorescence and Indocyanine Green During Robotic Pulmonary Resection," Frontiers in Surgery, Review, vol. 6, Aug. 2019, 7 pages.
Finsen, Niels, "The Red Light Treatment of Small-Pox," The British Medical Journal, Dec. 7, 1895, pp. 1412-1414.
Garza, Felix, et al., "Visible Blue Light Therapy: Molecular Mechanisms and Therapeutic Opportunities," Current Medical Chemistry, 2018, vol. 25, Bentham Science Publishers, pp. 5564-5577.
Glazer-Hockstein, "Could Blue Light-Blocking Lenses Decrease the Risk of Age-Related Macular Degeneration," Retina, vol. 26, 2006, 4 pages.
Gupta, Asheesh et al., "History and Fundamentals of Low-Level Laser (Light) Therapy," Handbook of Photomedicine, Chapter 5, CRC Press, 2014, pp. 43-52.
Hamblin, Michael, et al., "Can light-based approaches overcome antimicrobial resistance?," Drug Development Research, Jul. 2018, Wiley Periodicals, Inc., 20 pages.
Hamblin, Michael, et al., "Mechanisms of Low Level Light Therapy," Proceedings of the SPIE, vol. 6140, Feb. 10, 2006, pp. 614001-1 to 641001-12.
Arora, Prerna, et al., "B.1.617.2 enters and fuses lung cells with increased efficiency and evades antibodies induced by infection and vaccination," Cell Reports, vol. 37, Oct. 12, 2021, 12 pages.
Caly, Leon, et al., "The FDA-approved drug ivermectin inhibits the replication of SARS-CoV-2 in vitro," Antiviral Research, vol. 178, Apr. 3, 2020, Elsevier B.V., 4 pages.
Cele, Sandile, et al., "Escape of SARS-CoV-2 501Y.V2 from neutralization by convalescent plasma," Nature, vol. 593, May 6, 2021, 18 pages.
Cheng, Ya-Wen, et al., "D614G Substitution of SARS-CoV-2 Spike Protein Increases Syncytium Formation and Virus Titer via Enhanced Furin-Mediated Spike Cleavage," mBio, vol. 12, Issue 4, Jul. 27, 2021, 11 pages.
Do, et al., "A robust SARS-CoV-2 replication model in primary human epithelial cells at the air liquid interface to assess antiviral agents," Antiviral Research, vol. 192, Jun. 26, 2021, Elsevier, B.V., 8 pages.
Fulcher, et al., "Human Nasal and Tracheo-Bronchial Respiratory Epithelial Cell Culture," Methods in Molecular Biology, vol. 945, Chapter 8, 2012, pp. 109-121.
Gong, et al., "Contribution of single mutations to selected SARS-CoV-2 emerging variants spike antigenicity," Virology, vol. 563, Sep. 11, 2021, Elsevier Inc., 12 pages.
Good, Steven, et al., "AT-527 a Double Prodrug of a Guanosine Nucleotide Analog, Is a Potent Inhibitor of SARS-CoV-2 In Vitro and a Promising Oral Antiviral for Treatment of Covid-19," Antimicrobial Agents and Chemotherapy, vol. 65, Issue 4, Apr. 2021, 12 pages.
Harvey, William, et al., "SARS-CoV-2 variants, spike mutations and immune escape," Nature Reviews: Microbiology, vol. 19, Jul. 2021, pp. 409-424.
Heinen, Natalie, et al., "In Vitro Lung Models and Their Application to Study SARS-CoV-2 Pathogenesis and Disease," Viruses, vol. 13, Apr. 28, 2021, 17 pages.
Hou, Yixuan, et al., "SARS-CoV-2 Reverse Genetics Reveals a Variable Infection Gradient in the Respiratory Tract," Cell, vol. 182, Jul. 23, 2020, Elsevier Inc., 32 pages.
Huang, Ni, et al., "SARS-CoV-2 infection of the oral cavity and saliva," Nature Medicine, vol. 27, May 2021, 27 pages.
Krause, Philip, et al., "SARS-CoV-2 Variants and Vaccines," New England Journal of Medicine, vol. 385, Issue 2, Jul. 8, 2021, Massachusetts Medical Society, pp. 179-186.
Kumar, Sanjeev, et al., "Current status of therapeutic monoclonal antibodies against SARS-CoV-2," PLOS Pathogens, Sep. 3, 2021, 8 pages.
Levin, "Waning Immune Humoral Response to BNT162b2 Covid-19 Vaccine over 6 Months," New England Journal of Medicine, Oct. 6, 2021, Massachusetts Medical Society, 11 pages.
Liu, Haolin, et al., "The Lambda variant of SARS-CoV-2 has a better chance than the Delta variant to escape vaccines," Aug. 26, 2021, bioRxiv, 26 pages.
Liu, Jia, et al., "Hydroxychloroquine, a less toxic derivative of chloroquine, is effective in inhibiting SARS-CoV-2 infection in vitro," Cell Discovery, vol. 6, Issue 16, Mar. 18, 2020, 4 pages.
Liu, Yang, "Delta spike P681R mutation enhances SARS-CoV-2 fitness over Alpha variant," Sep. 5, 2021, bioRxv, 29 pages.
Marchesan, et al., "The 'oral' history of COVID-19: Primary infection, salivary transmission, and post-acute implications," Journal of Periodontology, vol. 92, American Academy of Periodontology, Jul. 2021, pp. 1357-1367.

(56) References Cited

OTHER PUBLICATIONS

McCullough, Peter, et al., "Pathophysiological Basis and Rationale for Early Outpatient Treatment of SARS-CoV-2 (COVID-19) Infection," The American Journal of Medicine, Review, vol. 134, Issue 1, Jan. 2021, Elsevier Inc., pp. 16-22.
Motozono, Chihiro, et al., "SARS-CoV-2 spike L452R variant evades cellular immunity and increases infectivity," Cell Host and Microbe, vol. 29, Jul. 14, 2021, Elsevier Inc., 24 pages.
Naaber, Paul, et al., "Dynamics of antibody response to BNT162b2 vaccine after six months: a longitudinal prospective study," The Lancet Regional Health—Europe, Sep. 6, 2021, 9 pages.
Planas, Delphine, et al., "Reduced sensitivity of SARS-CoV-2 variant Delta to antibody neutralization," Nature, vol. 596, Jul. 8, 2021, 20 pages.
Plante, Jessica, et al., "Spike mutation D614G alters SARS-CoV-2 fitness," Nature, vol. 592, Oct. 26, 2020, 22 pages.
Pouwels, Koen, et al., "Effect of Delta variant on viral burden and vaccine effectiveness against new SARS-CoV-2 infections in the UK," Nature Medicine, Oct. 14, 2021, 25 pages.
Pruijssers, Andrea, et al., "Remdesivir Inhibits SARS-CoV-2 in Human Lung Cells and Chimeric SARS-CoV Expressing the SARS-CoV-2 RNA Polymerase in Mice," Cell Reports, vol. 32, Jul. 21, 2020, 15 pages.
Sellgren, et al., "A biomimetic multicellular model of the airways using primary human cells," Lab on a Chip, Jun. 2014, The Royal Society of Chemistry, 10 pages.
Sheahan, Timothy, et al., "An orally bioavailable broad-spectrum antiviral inhibits SARS-CoV-2 in human airway epithelial cell cultures and multiple coronaviruses in mice," Science Translational Medicine, Research Article, vol. 12, Apr. 29, 2020, 16 pages.
Stasko, Nathan, et al., "A randomized, controlled, feasibility study of RD-X19 in patients with mild-to-moderate COVID-19 in the outpatient setting," Oct. 25, 2021, medRxiv, 30 pages.
Stasko, Nathan, et al., "Visible blue light inhibits infection and replication of SARS-CoV-2 at doses that are well-tolerated by human respiratory tissue," Scientific Reports, vol. 11, Oct. 18, 2021, 14 pages.
Touret, Franck, et al., "Preclinical evaluation of Imatinib does not support its use as an antiviral drug against SARS-CoV-2," Antiviral Research, vol. 193, Jul. 12, 2021, 8 pages.
Touret, Franck, et al., "Replicative Fitness of a SARS-CoV-2 201/501Y.V1 Variant from Lineage B.1.1.7 in Human Reconstituted Bronchial Epithelium," mBio, vol. 12, Issue 4, Jul. 2021, 4 pages.
Wang, Pengfei, et al., "Antibody resistance of SARS-CoV-2 variants B.1.351 and B.1.1.7," Nature, vol. 593, May 6, 2021, 18 pages.
Wildera, Marek, et al., "Limited Neutralization of Authentic Severe Acute Respiratory Syndrome Coronavirus 2 Variants Carrying E484K In Vitro," The Journal of Infectious Diseases, Jul. 5, 2021, pp. 1109-1114.
Final Office Action for U.S. Appl. No. 16/709,550, dated Dec. 27, 2021, 9 pages.
Advisory Action for U.S. Appl. No. 17/410,154, dated Jan. 25, 2022, 3 pages.
Non-Final Office Action for U.S. Appl. No. 17/410,166, dated Jan. 12, 2022, 12 pages.
Non-Final Office Action for U.S. Appl. No. 16/709,550, dated Jul. 12, 2021, 12 pages.
Non-Final Office Action for U.S. Appl. No. 16/898,385, dated Aug. 16, 2021, 12 pages.
Notice of Allowance for U.S. Appl. No. 17/117,889, dated Aug. 30, 2021, 9 pages.
Ahmed, Imran, et al., "Recent Patents on Light-Based Anti-Infective Approaches," Author Manuscript, Recent Patents on Anti-Infective Drug Discovery, vol. 13, Issue 1, 2018, 28 pages.
Akaberi, Dario, et al., "Mitigation of the replication of SARS-CoV-2 by nitric oxide in vitro," Redox Biology, vol. 37, Sep. 21, 2020, Elsevier B.V., 5 pages.
Author Unknown, "Assessing COVID-19-Related Symptoms in Outpatient Adult and Adolescent Subjects in Clinical Trials of Drugs and Biological Products for Covid-19 Prevention or Treatment," Guidance for Industry, US Department of Health and Human Services, Sep. 2020, 14 pages.
Baric, Ralph, "Emergence of a Highly Fit SARS-CoV-2 Variant," New England Journal of Medicine, vol. 383, Issue 27, Dec. 31, 2020, pp. 2684-2686.
Fajnzylber, Jesse, et al., "SARS-CoV-2 viral load is associated with increased disease severity and mortality," Nature Communications, vol. 11, Issue 1, Oct. 30, 2020, 9 pages.
Hamblin, Michael, "Mechanisms and Mitochondrial Redox Signaling in Photobiomodulation," Author Manuscript, Photochemistry and Photobiology, vol. 94, Issue 2, Mar. 2018, 31 pages.
Huang, Ni, et al., "Integrated Single-Cell Atlases Reveal an Oral SARS-CoV-2 Infection and Transmission Axis," medrXiv, Oct. 29, 2020, 22 pages.
Kim, Peter, et al., "Therapy for Early COVID-19: A Critical Need," JAMA, vol. 324, Issue 21, Nov. 11, 2020, American Medical Association, pp. 2149-2150.
Quirk, Brendan, et al., "What Lies at the Heart of Photobiomodulation: Light, Cytochrome C Oxidase, and Nitric Oxide—Review of the Evidence," Photobiomodulation, Photomedicine, and Laser Surgery, vol. 38, Issue 9, Jul. 2020, pp. 527-530.
To, KK, et al., "Temporal profiles of viral load in posterior oropharyngeal saliva samples and serum antibody responses during infection by SARS-CoV-2: an observational cohort study," Lancet Infectious Diseases, vol. 20, Issue 5, Mar. 23, 2020, 11 pages.
Wyllie, Anne, et al., "Saliva or nasopharyngeal swab specimens for detection of SARS-Cov-2," New England Journal of Medicine, vol. 383, Issue 13, Sep. 24, 2020, 4 pages.
Xu, Hao, et al., "High expression of ACE2 receptor of 2019-nCoV on the epithelial cells of oral mucosa," International Journal of Oral Science, vol. 12, Issue 8, Feb. 24, 2020, 5 pages.
Soukos, Nikolaos, et al., "Phototargeting Oral Black-Pigmented Bacteria," Antimicrobial Agents and Chemotherapy, Apr. 2005, vol. 49, Issue 4, pp. 1391-1396.
Non-Final Office Action for U.S. Appl. No. 17/117,889, dated Mar. 19, 2021, 17 pages.
Applicant-Initiated Interview Summary for U.S. Appl. No. 17/117,889, dated Apr. 19, 2021, 2 pages.
Final Office Action for U.S. Appl. No. 17/117,889, dated Apr. 30, 2021, 19 pages.
Author Unknown, "Scientific Breakthrough: Phototherapy Device," Facebook Timeline Photo, medicsBLU, Oct. 1, 2020, facebook com/medicsblu/, 4 pages.
Ankhzaya, "Airway management," slideshow, www.slideshare.net/gasilu/airway-management-111268937, Aug. 24, 2018, 87 pages.
Liu, et al., "Creation of a standardized geometry of the human nasal cavity," Journal of Applied Physiology, vol. 106, Jan. 2009, pp. 784-795.
International Search Report and Written Opinion for International Patent Application No. PCT/US2021/019785, dated Jun. 15, 2021, 18 pages.
Final Office Action for U.S. Appl. No. 16/709,550, dated Feb. 17, 2021, 12 pages.
Advisory Action and Examiner-Initiated Interview Summary for U.S. Appl. No. 17/117,889, dated May 19, 2021, 5 pages.
Advisory Action for U.S. Appl. No. 17/117,889, dated Jun. 4, 2021, 3 pages.
Gizurarson, Sveinbjorn, "Anatomical and Histological Factors Affecting Intranasal Drug and Vaccine Delivery," Current Drug Delivery, vol. 9, 2012, pp. 566-582.
Salehpour, Farzad, et al., "Therapeutic potential of intranasal photobiomodulation therapy for neurological and neuropsychiatric disorders: a narrative review," Reviews in the Neurosciences, vol. 31, Issue 3, Apr. 2020, 27 pages.
Spence, Callum, et al., "Stereoscopic PIV measurements of flow in the nasal cavity therapy," Experiments in Fluids, Apr. 2010, Springer, 13 pages.
Tong, Xuwen, et al., "Effects of nasal drug delivery device and its orientation on sprayed particle deposition in a realistic human nasal cavity," Computers in Biology and Medicine, vol. 77, 2016, pp. 40-48.

(56) References Cited

OTHER PUBLICATIONS

Wang, S.M., et al., "Comparison of micron- and nanoparticle deposition patterns in a realistic human nasal cavity," Respiratory Physiology & Neurobiology, vol. 166, 2009, pp. 142-151.
Xi, Jinxiang, et al., "Characterization of Submicrometer Aerosol Deposition in Extrathoracic Airways during Nasal Exhalation," Aerosol Science and Technology, vol. 43, 2009, pp. 808-827.
Yu, Shen, et al., "Numerical Analysis of the Relationship between Nasal Structure and Its Function," The Scientific World Journal, Feb. 2014, Hindawi Publishing Corporation, 6 pages.
Zwicker, David, et al., "Physical and geometric constraints explain the labyrinth-like shape of the nasal cavity," Proceedings of the National Academy of Sciences, Aug. 2017, 12 pages.
Non-Final Office Action for U.S. Appl. No. 16/898,385, dated Jun. 7, 2022, 13 pages.
Non-Final Office Action for U.S. Appl. No. 17/410,166, dated May 27, 2022, 11 pages.
Notice of Acceptance for Australian Patent Application No. 2021239894, dated Jun. 15, 2022, 3 pages.
Notice of Allowance for U.S. Appl. No. 16/709,550, dated Feb. 24, 2022, 8 pages.
Corrected Notice of Allowability for U.S. Appl. No. 16/709,550, dated Mar. 25, 2022, 5 pages.
Corrected Notice of Allowability for U.S. Appl. No. 16/709,550, dated Apr. 15, 2022, 5 pages.
Advisory Action for U.S. Appl. No. 16/898,385, dated Apr. 20, 2022, 4 pages.
Non-Final Office Action for U.S. Appl. No. 17/410,154, dated Feb. 24, 2022, 21 pages.
Final Office Action for U.S. Appl. No. 17/410,154, dated May 13, 2022, 18 pages.
Final Office Action for U.S. Appl. No. 17/410,166, dated Mar. 14, 2022, 13 pages.
Advisory Action for U.S. Appl. No. 17/410,166, dated May 11, 2022, 3 pages.
Notification of Reasons for Rejection for Japanese Patent Application No. 2021-518715, dated Apr. 26, 2022, 9 pages.
International Search Report and Written Opinion for International Patent Application No. PCT/US2022/019428, dated Jun. 14, 2022, 16 pages.
Examination Report for European Patent Application No. 16831333.6, dated May 20, 2022, 6 pages.
Advisory Action and Examiner-Initiated Interview Summary for U.S. Appl. No. 17/410,154, dated Jul. 5, 2022, 4 pages.
Final Office Action for U.S. Appl. No. 17/410,166, dated Jul. 1, 2022, 16 pages.
Non-Final Office Action for U.S. Appl. No. 17/162,259, dated Jul. 6, 2022, 17 pages.
Non-Final Office Action for U.S. Appl. No. 17/410,154, dated Jul. 28, 2022, 21 pages.
Notice of Allowance for Brazilian Patent Application No. BR112018001874-0, dated Aug. 28, 2022, 6 pages.
Corrected Notice of Allowability for U.S. Appl. No. 16/709,550, dated Sep. 21, 2022, 5 pages.
Non-Final Office Action for U.S. Appl. No. 17/148,124, dated Oct. 13, 2022, 21 pages.
Final Office Action for U.S. Appl. No. 17/410,154, dated Oct. 11, 2022, 20 pages.
Non-Final Office Action for U.S. Appl. No. 17/410,166, dated Oct. 18, 2022, 11 pages.
Final Office Action for U.S. Appl. No. 17/162,259, dated Oct. 19, 2022, 19 pages.
Non-Final Office Action for U.S. Appl. No. 17/162,283, dated Nov. 8, 2022, 12 pages.
Non-Final Office Action for U.S. Appl. No. 17/173,457, dated Oct. 17, 2022, 15 pages.
Second Office Action for Chinese Patent Application No. 202010561507.X, dated Jul. 15, 2022, 33 pages.
Advisory Action for U.S. Appl. No. 17/410,166, dated Sep. 7, 2022, 3 pages.
Final Office Action for U.S. Appl. No. 17/173,457, dated Feb. 23, 2023, 9 pages.
Advisory Action and Examiner-Initiated Interview Summary for U.S. Appl. No. 17/410,154, dated Jan. 10, 2023, 4 pages.
Notice of Allowance for U.S. Appl. No. 17/410,166, dated Feb. 15, 2023, 8 pages.
Advisory Action for U.S. Appl. No. 17/162,259, dated Jan. 9, 2023, 3 pages.
Final Office Action for U.S. Appl. No. 17/148,124, dated Mar. 13, 2023, 29 pages.
Notice of Allowance and Examiner-Initiated Interview Summary for U.S. Appl. No. 17/410,154, dated Mar. 9, 2023, 14 pages.
Non-Final Office Action for U.S. Appl. No. 17/162,259, dated Apr. 7, 2023, 18 pages.
Final Office Action for U.S. Appl. No. 17/162,283, dated Apr. 10, 2023, 10 pages.

\* cited by examiner

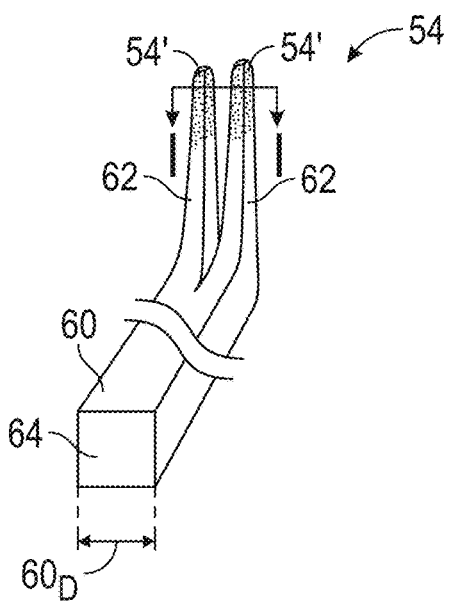
FIG. 5A
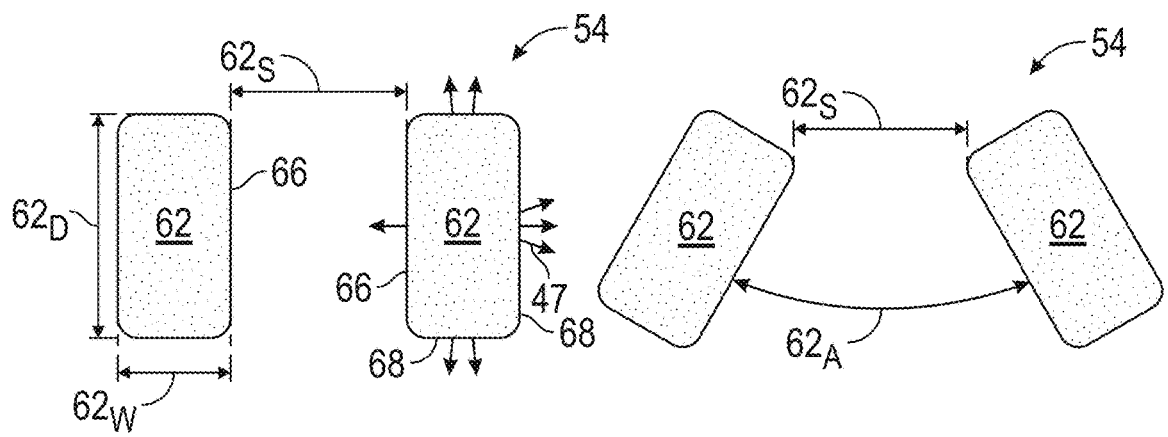
FIG. 5B
FIG. 5C
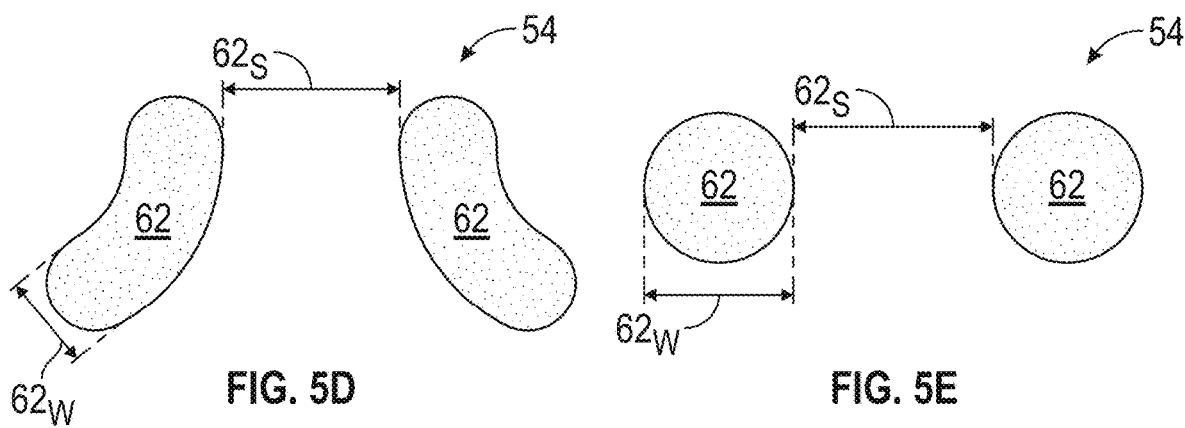
FIG. 5D
FIG. 5E

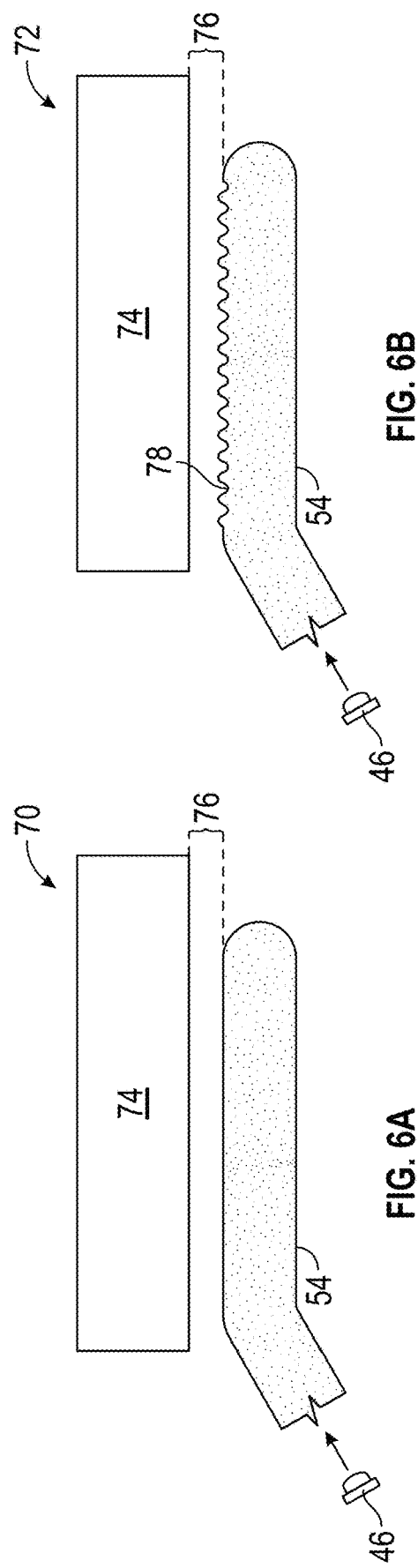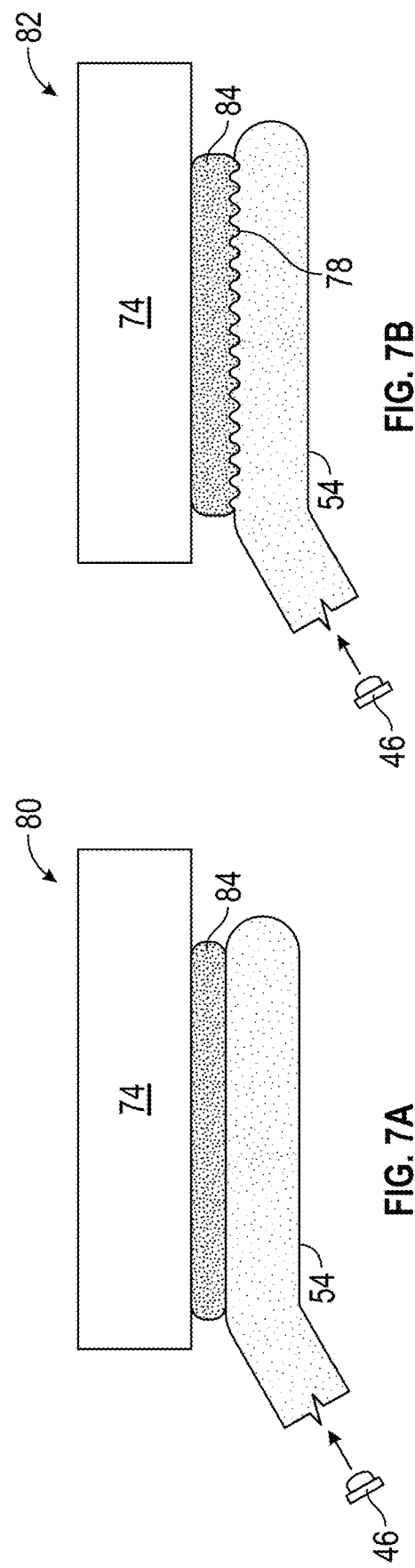

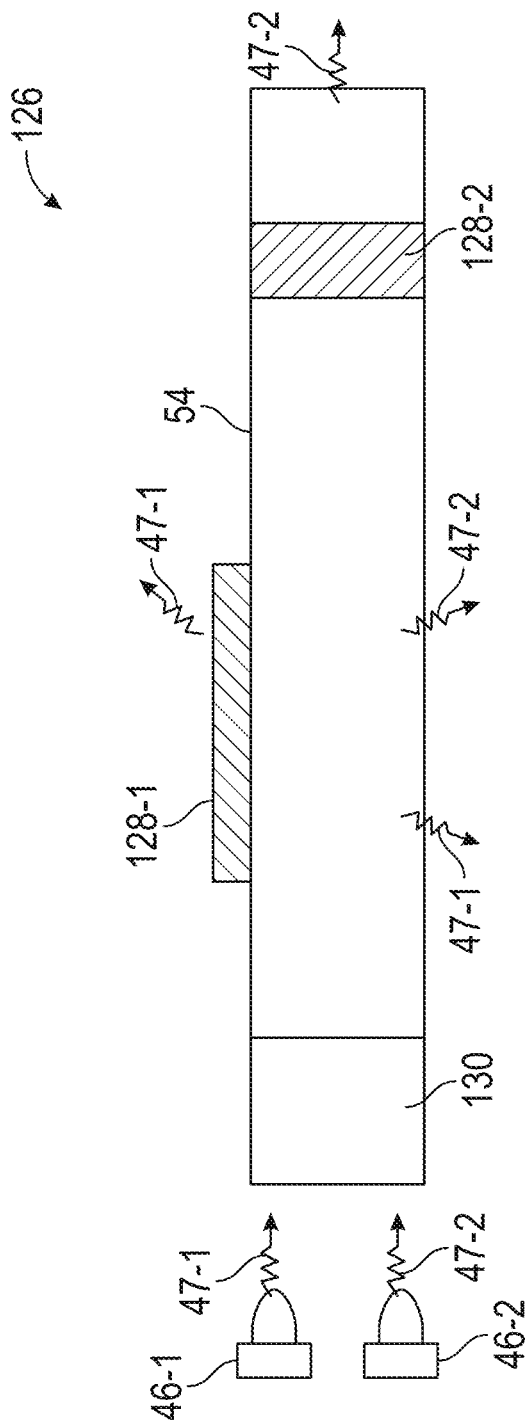

INTRANASAL ILLUMINATION DEVICES

FIELD OF THE DISCLOSURE

The present disclosure relates generally to devices and methods for impinging light on tissue to induce one or more biological effects, and more particularly to illumination devices and related methods that may be used for intranasal delivery of irradiation.

BACKGROUND

Microorganisms, including disease-causing pathogens, can typically invade tissues of the human body via mucosal surfaces within body cavities, such as mucous membranes or mucosae of the respiratory tract. A number of respiratory diseases and infections, including viral and bacterial, can be attributed to such disease-causing pathogens. Examples include Orthomyxoviridae (e.g., influenza), common colds, coronaviridae (e.g., coronavirus), picornavirus infections, tuberculosis, pneumonia, bronchitis, and sinusitis. Most respiratory tract infections begin when a subject is exposed to pathogen particles, which enter the body through the mouth and nose. For viral infections, cells at the site of infection must be accessible, susceptible, and permissive for the virus, and local host anti-viral defense systems must be absent or initially ineffective. Conventional treatments for infections may involve systemic administration of antimicrobials, such as antibiotics for bacterial infections, that can sometimes lead to drug resistance and gastro-intestinal distress. Other conventional treatment protocols may involve managing and enduring symptoms while waiting for infections to clear, particularly for viral infections.

Upper respiratory tract infections, including the common cold, influenza, and those resulting from exposure to coronaviridae are widely prevalent infections that continually impact the worldwide population. In some instances, upper respiratory tract infections can progress to cause serious and sometimes fatal diseases that develop in the lower respiratory tract or elsewhere in the body. In addition to upper respiratory tract conditions resulting from viral and/or bacterial infections, sinusitis may also be caused by allergies and exposure to pollutants, among other causes. The art continues to seek improved treatment options for upper respiratory tract conditions that are capable of overcoming challenges associated with conventional treatment options.

SUMMARY

The present disclosure relates generally to devices and methods for impinging light on tissue to induce one or more biological effects, and more particularly to illumination devices and related methods that may be used for intranasal delivery of irradiation. Exemplary illumination devices may include a light guide that is optically coupled with a light source, where the light guide may be configured for insertion along one or more intranasal passageways. In this manner, the light guide may provide irradiation of light to tissues along or near the upper respiratory tract to prevent and/or treat various infections and other tissue conditions thereof. Light guides may include flexible materials with suitable dimensions and/or shapes that allow the light guides to follow variable paths of intranasal passageways during use.

In one aspect, an illumination device comprises: at least one light source; driver circuitry configured to drive the at least one light source; and a light guide that is optically coupled to the at least one light source, the light guide being configured to extend through a nostril and an internal nasal valve of a user to position a portion of the light guide within a nasal cavity of the user. In certain embodiments, the at least one light source is positioned outside the nostril of the user. The illumination device may further comprise a housing that includes the at least one light source and the driver circuitry, wherein the light guide is removably attached to the housing. In certain embodiments, the light guide is removably attached to the housing by at least one of a securing tab, a threaded connection, a spring-clip, and a push-pin connection. In certain embodiments, the light guide is configured to bend between the nostril and portions of the nasal cavity during use. In certain embodiments, the light guide comprises a molded material with a pre-formed shape that includes a bend that resides between the nostril and portions of the nasal cavity during use. In certain embodiments, a length of the light guide between the bend and a distal end of the light guide is provided in a range from 1 centimeter (cm) to 10 cm, or in a range from 3 cm to 5 cm. In certain embodiments, the light guide comprises a flexible material for traversing the nostril and internal nasal valve during insertion. In certain embodiments, the light guide comprises silicone. In certain embodiments, an index of refraction of the light guide at 589.3 nm is in a range from greater than 1.33 to 1.8. In certain embodiments, the light guide comprises a light extraction section that is arranged to reside at least partially within the nasal cavity during use, wherein the light extraction section comprises at least one of a textured surface, a patterned surface, and an increased loading of disperser materials within the light guide.

In certain embodiments, the light guide comprises two extensions that extend from a base of the light guide and the two extensions are configured for simultaneous insertion into both nostrils and corresponding nasal cavities of the user. A width of the two extensions may decrease in a direction away from the at least one light source. In certain embodiments, a width of each of the two extensions is in a range from 0.25 cm to less than 2 cm. In certain embodiments, the two extensions are spaced from one another by a distance in a range from 0.7 cm to 1 cm. In certain embodiments, the two extensions are angled with respect to one another by an angle that is in a range from 45 degrees to 75 degrees. In certain embodiments, the base of the light guide comprises a rectangular or square-shaped cross-section and the two extensions comprise rectangular or square-shaped cross-sections that are smaller than the cross-section of the base. The two extensions may form arc-shapes that at least partially conform to the nostrils of the user. In certain embodiments, medial sides of each of the two extensions are formed where the two extensions face one another, and the medial sides are configured to extract less light from the light guide than other sides of the two extensions. In certain embodiments, the light guide comprises a hydrophobic material that is configured to repel mucus within the nasal cavity. In other embodiments, the light guide comprises a hydrophilic material that is configured to allow portions of the light guide to be wetted by mucus within the nasal cavity. In certain embodiments, the light guide comprises a positioner that is configured engage with one or more portions of the nostril during use. In certain embodiments, at least a portion of the light guide forms a spiral shape.

In certain embodiments, the at least one light source is configured to provide light with a first peak wavelength that induces at least one biological effect, the at least one biological effect comprising one or more of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain embodiments, the first peak wavelength is in a range from 400 nm to 450 nm. In certain embodiments, the at least one light source is configured to provide light with a second peak wavelength that is different than the first peak wavelength. In certain embodiments, the first peak wavelength may be provided in a range from 385 nm to 450 nm and the second peak wavelength may be provided in a range from 620 nm to 1,000 nm. In certain embodiments, the illumination device further comprises a light-selective feature that is arranged on or within a portion of the light guide, the light-selective feature being configured to preferentially allow certain wavelengths of light to pass through the light guide while restricting other wavelengths of light.

In another aspect, an illumination device comprises a light guide that is configured to extend through a nostril of a user to provide directed emissions toward at least one of a nasopharynx and an oropharynx of the user. In certain embodiments, a distal end of the light guide is configured to reside within a nasal cavity of the user and a primary emission surface of the light guide is oriented in a direction toward at least one of the nasopharynx and the oropharynx. In certain embodiments, the light guide is configured to provide at least a portion of light for irradiating tissue within the nasal cavity. In certain embodiments, the light guide comprises a first positioner that is configured engage with one or more portions of the nostril during use. In certain embodiments, the light guide further comprises a second positioner that is configured to engage with one or more surfaces between the nostril and a mouth of the user. In certain embodiments, the illumination device further comprises at least one light source optically coupled to the light guide and driver circuitry configured to drive the at least one light source. In certain embodiments, the at least one light source is arranged such that highest intensities of light emissions that exit the at least one light source are aligned in a direction that points directly toward at least one of the nasopharynx and the oropharynx.

In another aspect, an illumination device comprises a light guide that is configured to extend through an intranasal passageway of a user such that at least one emission surface of the light guide is arranged past a nasal cavity of the user and adjacent to at least one of a nasopharynx and an oropharynx of the user. In certain embodiments, the light guide is configured to irradiate tissue within the nasal cavity and tissue of at least one of the nasopharynx and the oropharynx during use. In certain embodiments, the light guide comprises a flexible material for traversing the intranasal passageway during insertion. In certain embodiments, the light guide is configured for magnetic steering through the intranasal passageway. In certain embodiments, a distal end of the light guide comprises an expanded shape compared with other portions of the light guide during use. In certain embodiments, the distal end is configured to expand after insertion through portions of the intranasal passageway. In certain embodiments, the illumination device further comprises at least one light source that is positioned within the distal end.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 5A is a perspective view of at least a portion of the light guide that includes a base section and extensions according to principles of the present disclosure.

FIG. 5B is a cross-sectional view of the light guide taken along the sectional line I-I of FIG. 5A.

FIG. 5C is a cross-sectional view of the light guide taken along the sectional line I-I of FIG. 5A for embodiments where the extensions may be angled with respect to one another.

FIG. 5D is a cross-sectional view of an alternative configuration of the light guide taken along the sectional line I-I of FIG. 5A for embodiments where the extensions may form curved shapes that correspond to portions of intranasal passageways.

FIG. 5E is a cross-sectional view of an alternative configuration of the light guide taken along the sectional line I-I of FIG. 5A for embodiments where the extensions may form circular shapes for insertion through intranasal passageways.

FIG. 6A is a diagram illustrating interaction between a light guide formed of a hydrophobic material and corresponding tissue of the upper respiratory tract according to principles of the present disclosure.

FIG. 6B is a diagram illustrating the light guide of FIG. 6A for embodiments where one or more surfaces of the light guide may be textured and/or patterned.

FIG. 7A is a diagram illustrating interaction between a light guide formed of a hydrophilic material and corresponding tissue of the upper respiratory tract according to principles of the present disclosure.

FIG. 7B is a diagram illustrating the light guide of FIG. 7A for embodiments where one or more surfaces of the light guide may be textured and/or patterned.

FIG. 19 is a side view of a portion of an exemplary illumination device where the light guide is configured to provide different light wavelengths out of one or more selected portions of the light guide according to principles of the present disclosure.

DETAILED DESCRIPTION

Figure 1:
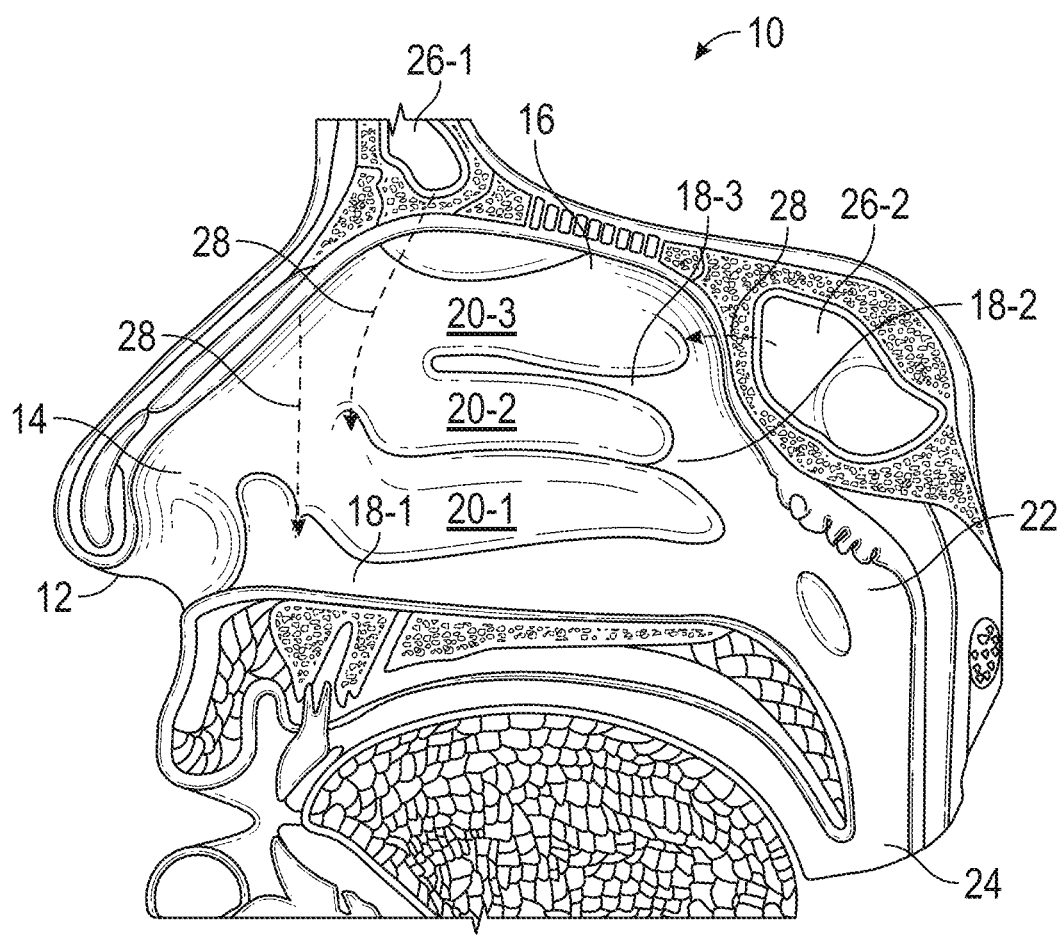
FIG. 1 is an illustration representing a cross-sectional view of an exemplary intranasal passageway.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

The present disclosure relates generally to devices and methods for impinging light on tissue to induce one or more biological effects, and more particularly to illumination devices and related methods that may be used for intranasal delivery of irradiation. Exemplary illumination devices may include a light guide that is optically coupled with a light source, where the light guide may be configured for insertion along one or more intranasal passageways. In this manner, the light guide may provide irradiation of light to tissues along or near the upper respiratory tract to prevent and/or treat various infections and other tissue conditions thereof. Light guides may include flexible materials with suitable dimensions that allow the light guides to follow variable paths of intranasal passageways during use.

Aspects of the present disclosure relate to devices and methods for impinging light on a mammalian tissue, for example within a body and/or a body cavity of a patient, where the light may include at least one characteristic that exerts or induces at least one biological effect within or on the tissue. Exemplary tissues include those of the upper respiratory tract, including tissues and cavities that are accessible via intranasal passageways. Biological effects may include at least one of inactivating and inhibiting growth of one or more combinations of microorganisms and pathogens, including but not limited to viruses, bacteria, fungi, and other microbes, among others. Biological effects may also include one or more of upregulating and/or downregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light may be selected based on at least one intended biological effect for one or more of the targeted tissues and the targeted microorganisms and/or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Aspects of the present disclosure relate to devices and methods for treating, preventing, and/or reducing the biological activity of pathogens while they are in one or more areas of the upper respiratory tract and hopefully before they travel to the lungs or elsewhere in the body. In certain aspects, devices and methods as disclosed herein may prevent or reduce infections by reducing microbial load along intranasal passageways, decreasing the ability for penetration into cells at the site of infection, and amplifying host defense systems, all of which may minimize or avoid the need for traditional antimicrobial medicines. In further aspects, devices and methods for light irradiation of tissues as disclosed herein may be provided to supplement and/or enhance the effects of traditional antimicrobial medicines.

The present disclosure is generally directed to illumination devices, apparatus, and methods for impinging light onto living tissue in order to induce one or more therapeutic biological effects. In various aspects, induced biological effects may include least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain aspects, the light may be referred to as nitric-oxide modulating light to increase concentrations of unbound nitric oxide within living tissue. Embodiments of the present disclosure may administer light at one or more wavelengths as a pre-exposure prophylaxis or a post-exposure prophylaxis in order to eliminate pathogens in or on tissue of the upper respiratory tract and/or amplify host defense systems. Embodiments of the present disclosure may be used to prevent and/or treat respiratory infections and other infectious diseases. For example, in certain embodiments, a hand-held illumination device may administer light at one or more wavelengths as a prophylactic measure to counteract invading viral pathogens and corresponding diseases that may originate in the respiratory tract. In a specific example, light may be administered that reduces viral infectivity and incidence of COVID-19 in individuals who have been infected or believe they may have been exposed to SARS-CoV-2 virus. In certain aspects, illumination devices of the present disclosure may be provided or referred to as phototherapeutic and/or phototherapy devices.

The term "phototherapy" relates to the therapeutic use of light. As used herein, phototherapy may be used to treat and/or prevent microbial infections, including viral infections of the upper respiratory tract. The mechanisms by which certain wavelengths of light are effective can vary, depending on the wavelength that is administered and the targeted microorganisms and/or pathogens. Biological effects, including antimicrobial effects, can be provided over a wide range of wavelengths, including ultraviolet (UV) ranges, visible light ranges, and infrared ranges, and combinations thereof.

Various wavelengths of visible light may be irradiated on human tissue with little or no impact on tissue viability. In certain embodiments, various wavelengths of visible light may elicit antimicrobial and/or anti-pathogenic behavior in tissue of the respiratory tract, including any of the aforementioned biological effects. For example, light with a peak wavelength in a range from 400 nanometers (nm) to 450 nm may inactivate microorganisms that are in a cell-free environment and/or inhibit replication of microorganisms that are in a cell-associated environment and/or stimulate enzymatic generation of nitric oxide, while also upregulating a local immune response in target tissue. In this regard, light with a peak wavelength in a range from 400 nm to 450 nm may be well suited for fighting invading viral pathogens and corresponding diseases that may originate in the respiratory tract, including Orthomyxoviridae (e.g., influenza), common colds, coronaviridae (e.g., coronavirus), picornavirus infections, tuberculosis, pneumonia, bronchitis, and sinusitis. In certain embodiments, red or near-infrared (NIR) light (e.g., peak wavelength range from 630 nm to 1,000 nm) may be useful to provide anti-inflammatory effects and/or to promote vasodilation. Anti-inflammatory effects may be useful in treating disorders, particularly microbial disorders that result in inflammation along the respiratory tract. In this regard, red light may be used as part of treatment protocols that reduce any tissue inflammation that may result from exposure to blue light, which may positively impact cell viability, thereby lowering cytotoxicity even further. A decrease in inflammation can be beneficial when treating viral infections, particularly when a virus can elicit a cytokine storm and/or inflammation can result in secondary bacterial infections. Accordingly, the combination of blue light, such as light at around 425 nm, and red light at one or more anti-inflammatory wavelengths, can provide a desirable combination of biological effects.

Depending on the application, other wavelength ranges of light may also be administered to human tissue. For example, UV light (e.g., UV-A light having a peak wavelength in a range of from 315 nm to 400 nm, UV-B light having a peak wavelength in a range of from 280 nm to 315 nm, and UV-C light having a peak wavelength in a range from 200 nm to 280 nm) may be effective for inactivating microorganisms that are in a cell-free environment and/or inhibit replication of microorganisms that are in a cell-associated environment and/or stimulate enzymatic generation of nitric oxide. However, overexposure to UV light may lead to cytotoxicity concerns in associated tissue. It may therefore be desirable to use shorter cycles and/or lower doses of UV light than corresponding treatments with only visible light. In certain embodiments, light with a peak wavelength in a range from 385 nm to 450 nm may be provided to elicit an antimicrobial and/or anti-pathogenic effect. In further embodiments, such wavelengths of light may be used in treatment protocols that also administer anti-inflammatory light.

An illumination device for the treatment of pathogens and/or for inducing one or more biological effects may take any form suitable for delivering light to the target tissue. The device may contain a light source capable of emitting a suitable light profile that can provide one or more direct or indirect biological effects. A light profile can be represented with a graph of emission intensity versus wavelength of light for any particular light source. In certain aspects, light sources may be provided with light characteristics in the visible spectrum, for example with light emissions with peak wavelengths primarily in a range from 400 nm to 700 nm. Depending on the target application, light characteristics may also include infrared or near-infrared peak wavelengths at or above 700 nm, or UV peak wavelengths at or below 400 nm. As used herein, light may include visual and non-visual electromagnetic radiation with single or multiple peak wavelengths in a range from 180 nm to 4000 nm. In certain embodiments, light emissions may have a single peak wavelength in a range from 200 nm to 1,000 nm, or in a range from 400 nm to 490 nm, or in a range from 400 nm to 435 nm, or in a range from 400 nm to 420 nm, or in a range from 400 nm to 440 nm, or in a range from 400 nm to 450 nm, or in a range from 420 nm to 440 nm, or in a range from 450 nm to 490 nm, or in a range from 500 nm to 900 nm, or in a range from 490 nm to 570 nm, or in a range from 510 nm to 550 nm, or in a range from 520 nm to 540 nm, or in a range from 525 nm to 535 nm, or in a range from 528 nm to 532 nm, or in from 630 nm to 670 nm, or in a range from 320 nm to 400 nm, or in a range from 385 nm to 450 nm, or in a range from 350 nm to 395 nm, or in a range from 280 nm to 320 nm, or in a range from 320 nm to 350 nm, or in a range from 200 nm to 280 nm, or in a range from 260 nm to 270 nm, or in a range from 240 nm to 250 nm, or in a range from 200 nm to 225 nm. In further embodiments, light emissions may include multiple peak wavelengths selected from any of the above listed ranges, depending on the target application and desired biological effects. Depending on the target application, full width half maximum (FWHM) values for any of the above-described peak wavelength ranges may be less than or equal to 100 nm, or less than or equal to 90 nm, or less than or equal to 40 nm, or less than or equal to 20 nm. In certain aspects, lower FWHM values are typically associated with single emission color light-emitting diodes (LEDs) in any of the above-described wavelength bands. Larger FWHM values (e.g., from 40 nm to 100 nm) may be associated with phosphor-converted LEDs where spectral bandwidths are a combination of LED emissions and phosphor-converted emissions. Exemplary phosphor-converted LEDs that may be applicable to the present disclosure are phosphor-converted amber LEDs having peak wavelengths in a range from 585 nm to 600 nm and FWHM values in a range from 70 nm to 100 nm, and phosphor-converted mint and/or lime LEDs having peak wavelengths in a range from 520 nm to 560 nm. Additional embodiments of the present disclosure may also be applicable to broad spectrum white LEDs that may include an LED with a peak wavelength in a range from 400 nm to 470 nm, and one or more phosphors to provide the broad emission spectrum. In such embodiments, a broad spectrum LED may provide certain wavelengths that induce one or more biological effects while also providing broad spectrum emissions to the target area for illumination. In this regard, light impingement on tissue for single and/or multiple microorganisms and/or multiple pathogenic biological effects may be provided with light of a single peak wavelength or a combination of light with more than one peak wavelength.

Doses of light to induce one or more biological effects may be administered with one or more light characteristics, including peak wavelengths, radiant flux, and irradiance to target tissues. Irradiances to target tissues may be provided in a range from 0.1 milliwatts per square centimeter (mW/cm$^2$) to 200 mW/cm$^2$, or in a range from 5 mW/cm$^2$ to 200 mW/cm$^2$, or in a range from 5 mW/cm$^2$ to 100 mW/cm$^2$, or in a range from 5 mW/cm$^2$ to 60 mW/cm$^2$, or in a range from 60 mW/cm$^2$ to 100 mW/cm$^2$, or in a range from 100 mW/cm$^2$ to 200 mW/cm$^2$. Such irradiance ranges may be administered in one or more of continuous wave and pulsed configurations, including LED-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in another range specified herein. Depending on the configuration of one or more of the light source, the corresponding illumination device, and the distance away from a target tissue, the radiant flux value for the light source may be higher than the irradiance value at the tissue.

While certain peak wavelengths for certain target tissue types may be administered with irradiances up to 1 $W/cm^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 $W/cm^2$ to 10 $W/cm^2$ may be safely pulsed to target tissue.

Administered doses of light, or light doses, may be referred to as therapeutic doses of light in certain aspects. Doses of light may include various suitable combinations of the peak wavelength, the irradiance to the target tissue, and the exposure time period. Particular doses of light are disclosed that are tailored to provide safe and effective light for inducing one or more biological effects for various types of pathogens and corresponding tissue types. In certain aspects, the dose of light may be administered within a single time period in a continuous or a pulsed manner. In further aspects, a dose of light may be repeatably administered over a number of times to provide a cumulative or total dose over a cumulative time period. By way of example, a single dose of light as disclosed herein may be provided over a single time period, such as in a range from 10 microseconds to no more than an hour, or in a range from 10 seconds to no more than an hour, while the single dose may be repeated at least twice to provide a cumulative dose over a cumulative time period, such as a 24-hour time period. In certain embodiments, doses of light are described that may be provided in a range from 0.5 joules per square centimeter ($J/cm^2$) to 100 $J/cm^2$, or in a range from 0.5 $J/cm^2$ to 50 $J/cm^2$, or in a range from 2 $J/cm^2$ to 80 $J/cm^2$, or in a range from 5 $J/cm^2$ to 50 $J/cm^2$, while corresponding cumulative doses may be provided in a range from 1 $J/cm^2$ to 1000 $J/cm^2$, or in a range from 1 $J/cm^2$ to 500 $J/cm^2$, or in a range from 1 $J/cm^2$ to 200 $J/cm^2$, or in a range from 1 $J/cm^2$ to 100 $J/cm^2$, or in a range from 4 $J/cm^2$ to 160 $J/cm^2$, or in a range from 10 $J/cm^2$ to 100 $J/cm^2$, among other disclosed ranges. In a specific example, a single dose may be administered in a range from 10 $J/cm^2$ to 20 $J/cm^2$, and the single dose may be repeated twice a day for four consecutive days to provide a cumulative dose in a range from 80 $J/cm^2$ to 160 $J/cm^2$. In another specific example, a single dose may be administered at about 30 $J/cm^2$, and the single dose may be repeated twice a day for seven consecutive days to provide a cumulative dose of 420 $J/cm^2$.

In still further aspects, light for inducing one or more biological effects may include administering different doses of light to a target tissue to induce one or more biological effects for different target pathogens. As disclosed herein, a biological effect may include altering a concentration of one or more pathogens within the body and altering growth of the one or more pathogens within the body. The biological effect may include at least one of inactivating a first pathogen in a cell-free environment, inhibiting replication of the first pathogen in a cell-associated environment, upregulating a local immune response in mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. As further disclosed herein, a pathogen may include a virus, a bacteria, and a fungus, or other any other types of microorganisms that can cause infections. Notably, light doses as disclosed herein may provide non-systemic and durable effects to targeted tissues. Light can be applied locally and without off-target tissue effects or overall systemic effects associated with conventional drug therapies which can spread throughout the body. In this regard, phototherapy may induce a biological effect and/or response in a target tissue without triggering the same or other biological responses in other parts of the body. Phototherapy as described herein may be administered with safe and effective doses that are durable. For example, a dose may be applied for minutes at a time, one to a few times a day, and the beneficial effect of the phototherapy may continue in between treatments.

Light sources may include one or more of LEDs, organic LEDs (OLEDs), lasers and other lamps according to aspects of the present disclosure. Lasers may be used for irradiation in combination with optical fibers or other delivery mechanisms. LEDs are solid state electronic devices capable of emitting light when electrically activated. LEDs may be configured across many different targeted emission spectrum bands with high efficiency and relatively low costs. Accordingly, LEDs may be used as light sources in photonic devices for phototherapy applications. Light from an LED is administered using a device capable of delivering the requisite power to a targeted treatment area or tissue. High power LED-based devices can be employed to fulfill various spectral and power needs for a variety of different medical applications. LED-based photonic devices described herein may be configured with suitable power to provide irradiances as high as 100 $mW/cm^2$, or 200 $mW/cm^2$ in the desired wavelength range. An LED array in this device can be incorporated into an irradiation head, hand piece and/or as an external unit.

In addition to various sources of light, the principles of the present disclosure are also applicable to one or more other types of directed energy sources. As used herein, a directed energy source may include any of the various light sources previously described, and/or an energy source capable of providing one or more of heat, IR heating, resistance heating, radio waves, microwaves, soundwaves, ultrasound waves, electromagnetic interference, and electromagnetic radiation that may be directed to a target body tissue. Combinations of visual and non-visual electromagnetic radiation may include peak wavelengths in a range from 180 nm to 4000 nm. Illumination devices as disclosed herein may include a light source and another directed energy source capable of providing directed energy beyond visible and UV light. In other embodiments, the other directed energy source capable of providing directed energy beyond visible and UV light may be provided separately from illumination devices of the present disclosure.

According to aspects of the present disclosure, exemplary target tissues and cells for intranasal light treatments may include one or more tissues of the upper respiratory tract, including the nasal cavity, ostium from paranasal sinus cavities, and the pharynx, including the nasopharynx and the oropharynx. FIG. 1 is an illustration representing a cross-sectional view of an exemplary intranasal passageway 10. As illustrated, the intranasal passageway 10 includes a nostril 12 and nasal vestibule 14 that lead to a nasal cavity 16. Within the nasal cavity 16, three nasal meatuses 18-1 to 18-3 are formed from three corresponding nasal conchae 20-1 to 20-3. The nasal meatus 18-1, which may be referred to as the inferior meatus, extends along most of the length of the nasal cavity 16 in a direction toward a nasopharynx 22 and oropharynx 24. The nasal meatus 18-2 may be referred to as the middle meatus and the nasal meatus 18-3 may be referred to as the superior meatus. Paranasal sinus cavities 26-1, 26-2 are positioned outside the nasal cavity 16. The sinus cavity 26-1 may be referred to as a frontal sinus cavity and sinus cavity 26-2 may be referred to as a sphenoid sinus cavity. Each of the paranasal sinus cavities 26-1, 26-2 are joined to the nasal cavity 16 by at least one corresponding ostium that provides a drainage path 28 to the nasal cavity 16, as indicated by the superimposed dashed line arrows in FIG. 1. Each ostium may be obscured by the nasal conchae 20-1 to 20-3 and the end of each ostium may be provided along one of the sinus cavities 26-1, 26-2. The ostium can become blocked in response to various conditions, including various viral and/or bacterial infections, leading to sinusitis. As will be further described below in greater detail, aspects of the present disclosure are related to devices and methods for providing therapeutic doses of light within the nasal cavity 16 and/or other parts of the body, including the nasopharynx 22 and oropharynx 24, by way of one or more portions of the intranasal passageway 10.

Figure 2A:
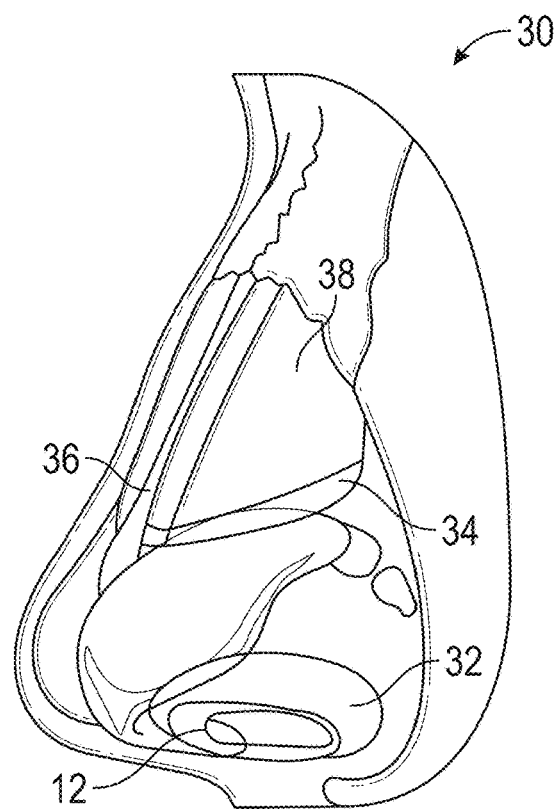
FIG. 2A is a side view of an exemplary nose illustrating locations of an external nasal valve and an internal nasal valve.
Figure 2B:
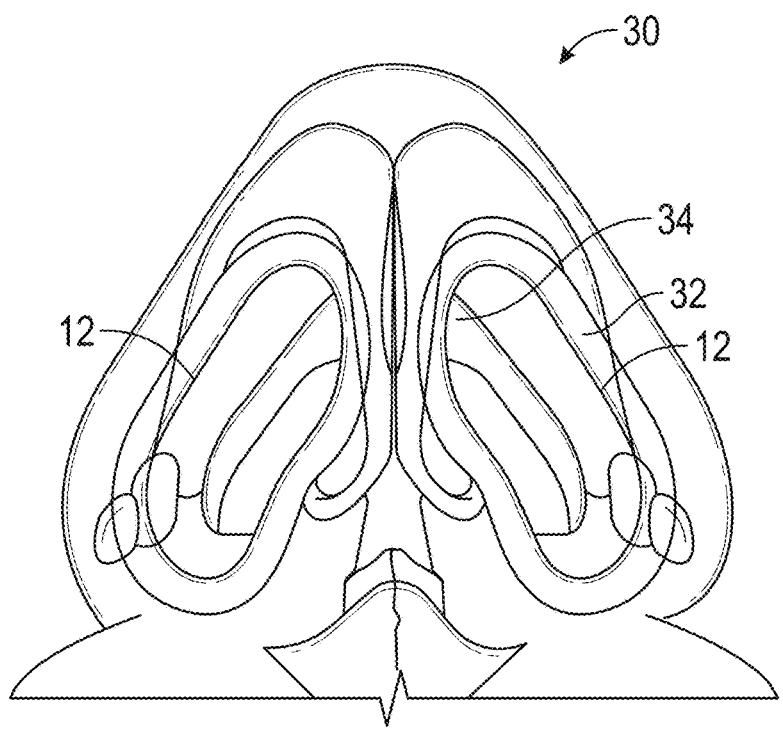
FIG. 2B is a bottom view of the nose of FIG. 2A.

Overall geometries of intranasal passageways can be highly variable and circuitous from person to person. The relative shapes of nasal valves between individuals can provide further anatomical differences that should also be accounted for when administering light therapy via the intranasal passageway. FIG. 2A is a side view of an exemplary nose 30 illustrating locations of an external nasal valve 32 and an internal nasal value 34. FIG. 2B is a bottom view of the nose 30 of FIG. 2A. The external nasal valves 32 corresponds with the nostrils 12 and the internal nasal valves 34 are positioned between a nasal septum 36 and upper lateral cartilages 38 of the nose 30, leading to the corresponding nasal cavities. The internal nasal valve 34 may correspond with a narrowest part of the intranasal passageway. During normal breathing, the internal nasal valve 34 controls or limits an amount of airflow that may be inhaled. Additionally, the internal nasal valve 34 may toggle control for which side of the nose 30 and corresponding nasal cavity is used for breathing at a given time.

Figure 2C:
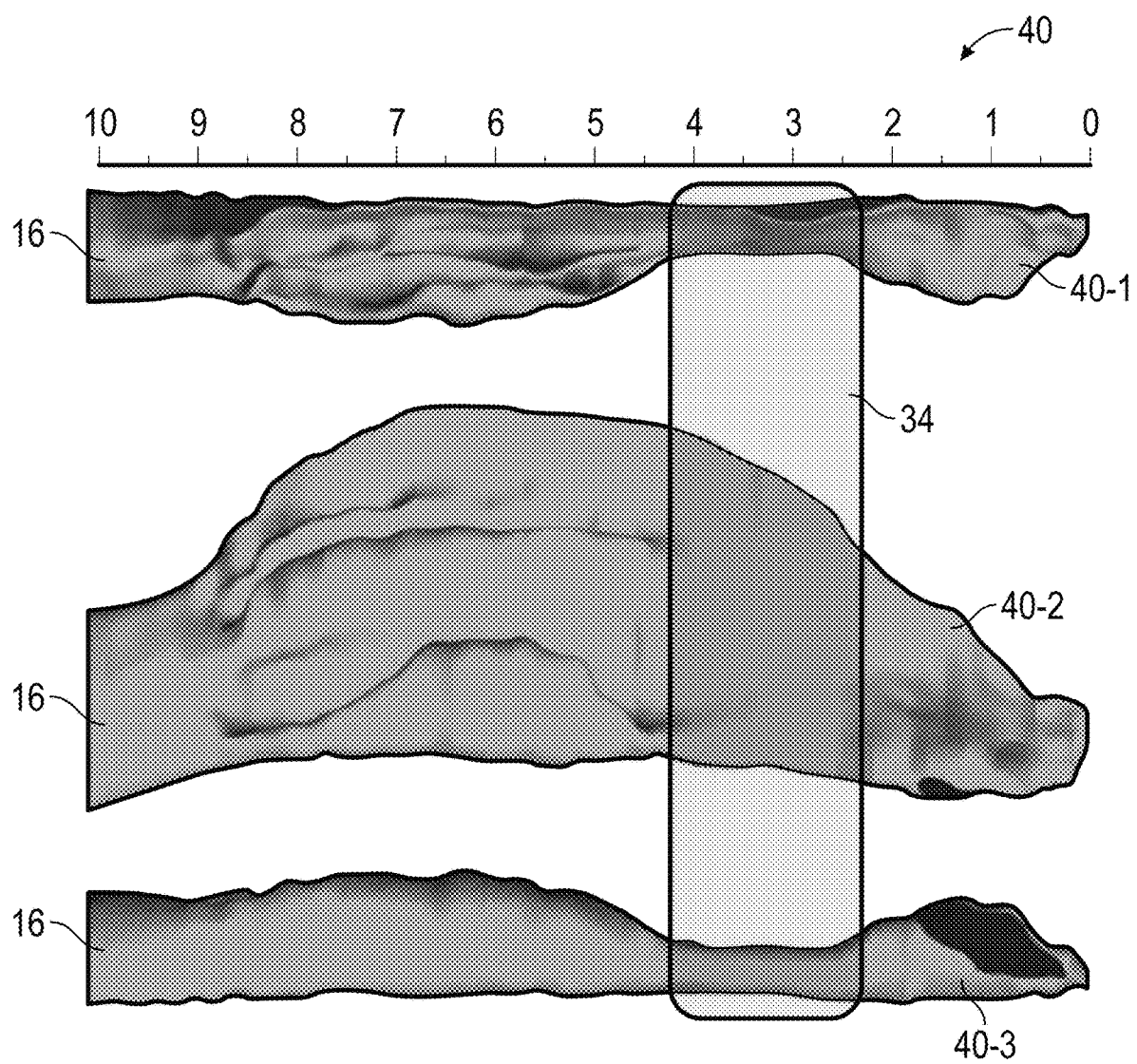
FIG. 2C is an illustration that shows a three-dimensional (3D) model of a standardized geometry of a human nasal cavity superimposed with a location of the internal nasal valve.

FIG. 2C is an illustration that shows a three-dimensional (3D) model 40 of a standardized geometry of the human nasal cavity 16 superimposed with a location of the internal nasal valve 34 of FIGS. 2A and 2B. The scale provided in FIG. 2C is shown in centimeters (cm) as measured from a front of the nasal cavity 16 near the nostrils toward a back of the nasal cavity 16. The 3D model 40 is the standardized model provided by Liu et al. as referenced in the Journal of Applied Physiology paper titled "Creation of a Standardized Geometry of the Human Nasal Cavity," volume 106, pages 784-795, and published Jan. 8, 2009. In FIG. 2C, a top portion 40-1 represents a top view of the 3D model 40, a middle portion 40-2 represents a side view of the 3D model 40, and a bottom portion 40-3 represents a bottom view of the 3D model 40. As illustrated, the internal nasal valve 34 may be provided in a range from above 2 cm to almost 4.5 cm into the nasal cavity 16. As illustrated in the top view 40-1 and the bottom view 40-3, the nasal cavity 16 can narrow to a width that is less than 1 cm, for example in a range from about 0.4 to 0.5 cm, at the internal nasal valve 34. As will be further described below in greater detail, aspects of the present disclosure provide illumination devices and related methods that deliver intranasal doses of light to portions of the nasal cavity 16 and/or other parts of the body that are past the internal nasal valve 34.

Figure 3:
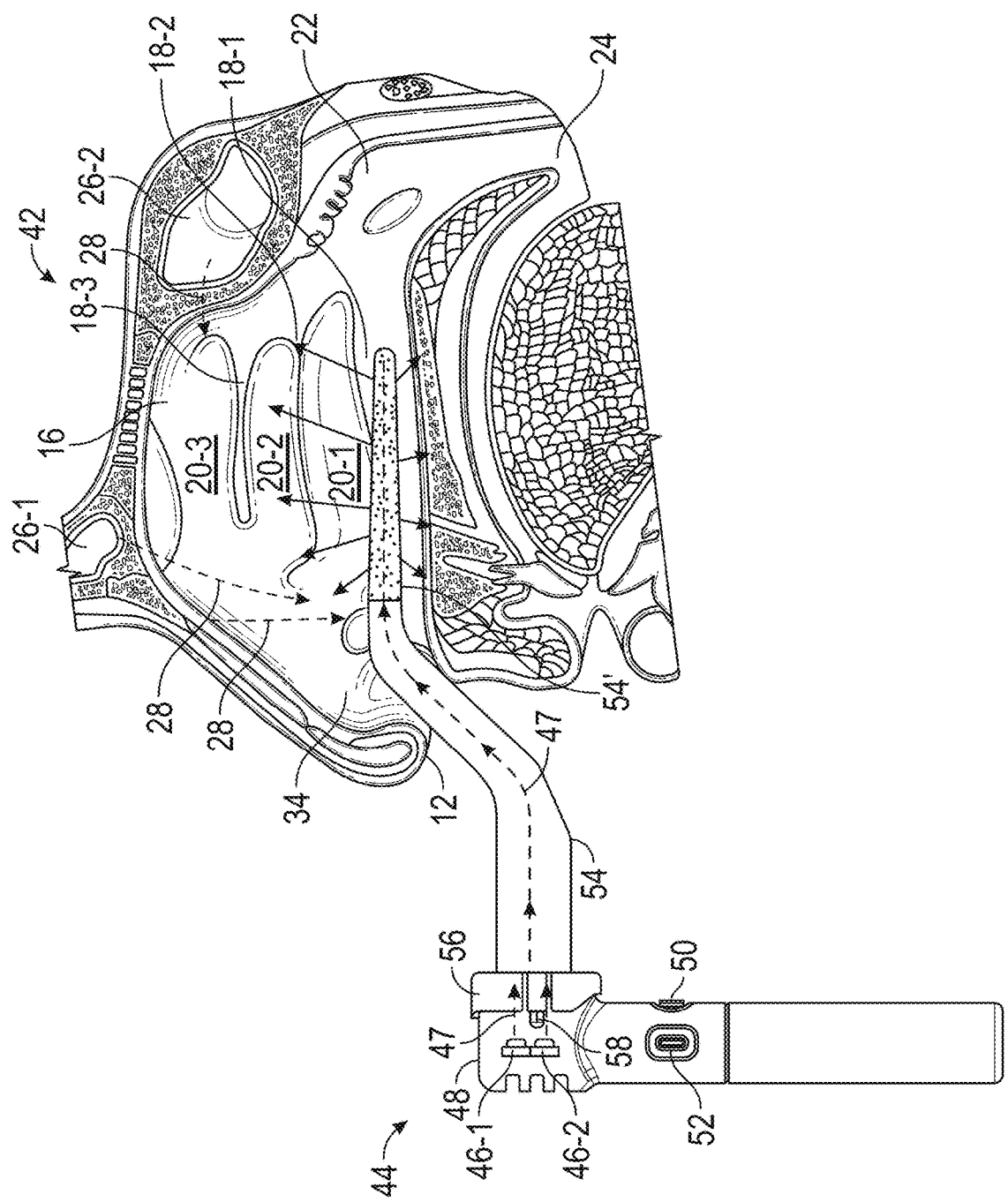
FIG. 3 is a cross-sectional view of an intranasal passageway during light treatment with an illumination device that is configured to provide light to one or more portions of the nasal cavity that are past the internal nasal valve.

FIG. 3 is a cross-sectional view of an intranasal passageway 42 during light treatment with an illumination device 44 that is configured to provide light 47 to one or more portions of the nasal cavity 16 that are past the internal nasal valve 34. The illumination device 44 may include a number of light emitters 46-1, 46-2 that are arranged within a housing 48. The light emitters 46-1, 46-2 may include any light source capable of emitting light 47 that may induce one or more of the aforementioned biological effects, including but not limited to LEDs, OLEDs, superluminescent diodes (SLDs), lasers, and/or any combinations thereof. Where a light emitter is described as emitting light of a wavelength or a range of wavelengths, it should be understood that the term wavelength could refer to a dominant wavelength or a peak wavelength. Unless otherwise specified, various embodiments are provided herein with reference to peak wavelengths. For illustrative purposes, two light emitters 46-1, 46-2 are shown; however, any number of light emitters 46-1, 46-2 may be provided without deviating from the principles disclosed. For example, the illumination device 44 may include a single light emitter or an array of light emitters, such as two or more, three or more, four or more, or greater. The light emitters 46-1, 46-2 may be configured to emit a same peak wavelength of light or different peak wavelengths of light depending on the application. For embodiments where the light emitters 46-1, 46-2 emit different peak wavelengths, each of the light emitters 46-1, 46-2 may be configured to provide a light characteristic that induces different biological effects from one another. In certain embodiments, the light emitter 46-1 may provide a first peak wavelength and a first radiant flux to induce one or more of the aforementioned biological effects, and the light emitter 46-2 may provide a second peak wavelength and a second radiant flux to induce at least one different one of the aforementioned biological effects. In certain embodiments, the second peak wavelength may be greater than the first peak wavelength by at least 25 nm, at least 40 nm, at least 50 nm, at least 60 nm, at least 75 nm, at least 85 nm, at least 100 nm, or another threshold specified herein.

The illumination device 44 may embody a hand-held device that may be user operated. In this regard, the illumination device 44 may include a button 50 or switch for energizing the illumination device 44 and/or the light emitters 46-1, 46-2. The housing 48 may further include a port 52 for one or more of charging the illumination device 44, accessing data stored within the illumination device 44, and providing data to the illumination device 44 for providing irradiation to targeted tissue within or through the intranasal passageway 42. The illumination device 44 may further include driver circuitry operable to control output and drive the light emitters 46-1, 46-2. For multiple wavelength embodiments, the driver circuitry may be configured to independently activate each of the light emitters 46-1, 46-2 so that the illumination device 44 is operable to provide different peak wavelengths to target tissue during overlapping and/or non-overlapping treatment windows.

As illustrated, the illumination device 44 may be configured to provide the light emitters 46-1, 46-2 in a position that is outside the nostrils 12 and the nasal cavity 16 of the user's body. In order to deliver the light 47 to positions within or through the intranasal passageway 42, the illumination device 44 may include a light guide 54 that is optically coupled to the light emitters 46-1, 46-2. The light guide 54 may be connected to the housing 48 by way of a connector 56 that engages the housing 48 and positions the lightguide 54 in optical communication with the light emitters 46-1, 46-2. In this manner, the light guide 54 may receive light 47 that is generated when the light emitters 46-1, 46-2 are electrically activated. The connector 56 may include one or more securing tabs 58 that shaped to engage with corresponding notches of features of the housing 48. In various configurations, the connector 56 may be connected to the housing 48 by any number of mechanical configurations, included threaded connections, spring-clip connections, and push-pin connections. In this regard, the light guide 54 may be configured to be removably attached to the illumination device 44, thereby providing the ability to use differently-shaped light guides with the illumination device 44 and/or the ability to clean the light guide 54 separately from the illumination device 44 between uses.

The light guide 54 may include any light delivery element, including but not limited to waveguides, optical fiber bundles, fiber optic cables, dispersers, diffusers, optical lenses, and the like that are operable to deliver the light 47 to tissue within or through the intranasal passageway 42. The light guide 54 may be constructed from a material that is configured to reduce internal absorption of the light 47, thereby providing suitable transmission of the light 47 from the light emitters 46-1, 46-2 to tissue within the nasal cavity 16. As described above, intranasal geometries may be widely variable between different individuals of a population and intranasal passageways further include restricted openings at internal nasal valves. In this regard, the light guide 54 of the present disclosure is configured to be flexible and with suitably small dimensions so that the light guide 54 may accommodate a wide variety of intranasal geometries for repeatable delivery of therapeutic doses of light. For example, the light guide 54 may be configured to bend at least once between the nostril 12 and the nasal cavity 16 during use. In certain embodiments, the light guide 54 may comprise any number of medical-grade device materials that are suitable for use on and/or within mammalian body tissues and/or cavities. The light guide 54 may comprise a flexible and molded material, where the molded material provides a pre-formed shape with one or more bends that allow the light guide 54 to enter the nostrils 12 and then be positioned to extend at least partially through the nasal cavity 16. By way of example, the light guide 54 may include a material with a Shore-A durometer hardness rating to provide flexibility. In certain embodiments, the light guide 54 may comprise a material that exhibits an index of refraction that is higher than water. For example, the light guide 54 may comprise silicone with an index of refraction of about 1.42 at a wavelength of 589.3 nm compared with an index of refraction of water at 1.33 for the same wavelength. In still further embodiments, the light guide 54 may comprise liquid silicone rubber. In other embodiments, the index of refraction of the light guide 54 may be greater than 1.42 and up to about 1.8 at a wavelength of 589.3 nm to improve light confinement. In certain embodiments with index of refraction values up to 1.8, the light guide 54 may comprise one or more polycarbonate materials. By providing the light guide 54 with a flexible material that also includes an index of refraction that is higher than water, the light guide 54 may be suitably configured to deliver light to targeted tissues of the nasal cavity 16 and beyond. In certain embodiments, the index of refraction of the light guide 54 may be higher than water, but still within about 0.15 of water (e.g., in a range from greater than 1.33 to 1.48) to allow some light to escape or leak out of the light guide 54 along multiple portions of the light guide 54 within the nasal cavity 16. In this manner, the light guide 54 may be referred to as a leaky light guide that provides light throughout the nasal cavity 16 during use. In other embodiments, the light guide 54 may comprise a more rigid material, such as one or more polycarbonates or glass, that may provide any of the above-described optical properties. When the light guide 54 is formed of a more rigid material, the pre-formed shape and dimensions may be suitably formed with the one or more bends to allow the light guide 54 to enter the nostrils 12 and extend within the nasal cavity 16.

As illustrated in FIG. 3, the light guide 54 may be configured with a width that gradually tapers in a direction away from the illumination device 44. In this manner, the light guide 54 may be suitable sized to collect light 47 from the light emitters 46-1, 46-2 while also allowing passage of the light guide 54 through the internal nasal valve 34, into the nasal cavity 16, and along one or more of the meatuses 18-1 to 18-3. The tapering may be provided for comfort during insertion. In other embodiments, the distal end of the light guide 54 may be configured to allow a portion of the light 47 to escape in a direction toward the nasopharynx 22 and the oropharynx 24. When positioned within the nasal cavity 16, the flexible nature of the light guide 54 may allow the light guide 54 to be in contact, or direct contact, with tissue along one or more portions of the nasal cavity 16. In this manner, light 47 that escapes the light guide 54 may be more directly absorbed by targeted tissue. In certain embodiments, the flexible and/or deformable nature of the light guide 54 may allow it to conform to one or more tissue surfaces along the upper respiratory tract when in contact with the tissue. Additionally, the long and somewhat narrow dimensions of the flexible light guide 54 may provide increased surface area within the nasal cavity 16. In certain embodiments, the increases surface area may provide a more even distribution of surface energy along the light guide 54, thereby keeping surface energy levels that contact tissue within safe and tolerable levels.

The flexible nature of the light guide 54 may also allow the light guide 54 to readily extend along narrow portions within the nasal cavity 16 in order to target specific areas for light treatment. For example, the light guide 54 may be arranged to extend along one or more of the meatuses 18-1 to 18-3 to target irradiation to at least one ostium of any of the paranasal sinus cavities 26-1, 26-2. As illustrated in FIG. 3, each ostium may provide a drainage path to the nasal cavity 16 along a path 28 represented by the superimposed dashed line arrows. By providing the light guide 54 along or in close proximity to one or more of the meatuses 18-1 to 18-3 defined by the nasal conchae 20-1 to 20-3, the end of each ostium may be targeted for light irradiation. In this manner, one or more of the previously described biological effects may be induced for treating and/or preventing various sinus-related conditions such as sinusitis, that may be caused by viral and/or bacterial infections, allergies, and exposure to pollutants, among others.

The light guide 54 may include a light extraction section 54' that is configured to provide increased light extraction relative to other portions of the light guide 54. In certain embodiments, one or more portions of the light extraction section 54' may be arranged to reside within the nasal cavity 16 during use. For example, the light extraction section 54' may comprise a portion of the light guide 54 that includes surface texturing and/or patterning so that increased amounts of the light 47 may preferentially escape from the light extraction section 54'. In certain embodiments, the light extraction section 54' may comprise a portion of the light guide 54 that is loaded with higher concentrations of disperser and/or diffusing materials that promote increased amounts of the light 47 to escape. By arranging the light extraction section 54' at a distal end of the light guide 54 from the light emitters 46-1, 46-2, light 47 may propagate through the light guide 54 and toward targeted tissue of the respiratory tract that would otherwise not be assessable. For example, light 47 may escape the light guide 54 (and light extraction section 54') along areas of the meatuses 18-1 to 18-3 and toward one or more of the ostia from the paranasal sinus cavities 26-1, 26-2. In certain embodiments, the light extraction section 54' corresponds to a portion of the light guide 54 that is a primary light emitting portion and the remainder of the light guide 54 may correspond to a primary light transmitting portion of the light guide 54. In certain embodiments, the light guide 54 may be configured to split into two portions or extensions for simultaneous insertion into each nostril 12 and corresponding nasal cavity 16 of a user. In other embodiments, the light guide 54 may embody a single extension for insertion into a single nostril 12 and nasal cavity 16 at a time, or to provide therapeutic doses of light within other cavities of the body.

Figure 4:
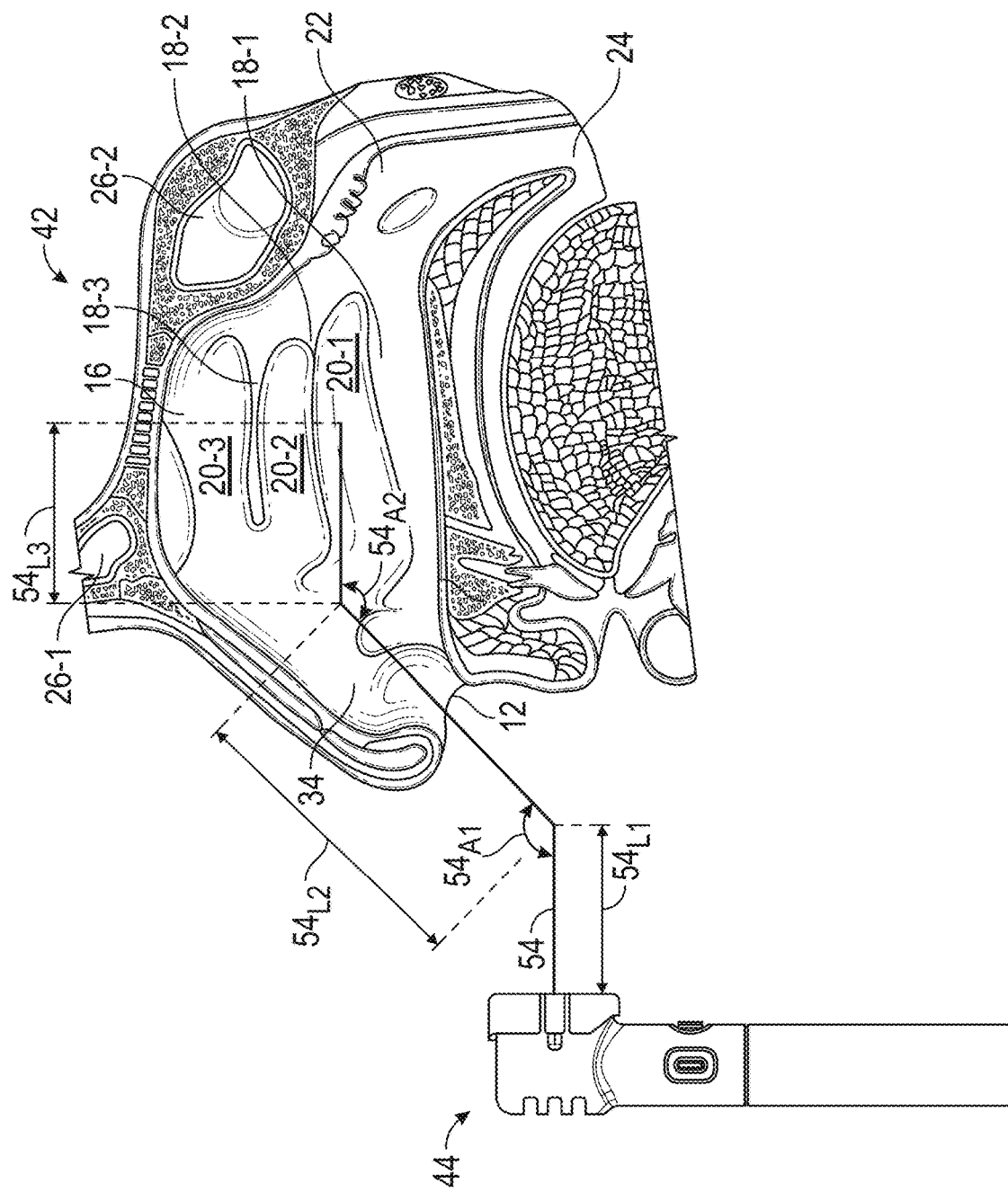
FIG. 4 is a cross-sectional view of the intranasal passageway of FIG. 3 illustrating relative dimensions of a light path provided by a light guide.

FIG. 4 is a cross-sectional view of the intranasal passageway 42 of FIG. 3 illustrating relative dimensions of a light path provided by the light guide 54. For illustrative purposes, the light guide 54 is represented by a series of lines that extend from the illumination device 44 and into the nasal cavity 16. As previously described, the light guide 54 may embody a flexible material that is deformable to allow routing along the various bends and curves of the intranasal passageway 42. As illustrated, the light guide 54 may bend along one or more portions to enter the nasal cavity 16. By way of example, the light guide 54 may be configured to bend along a first angle $54_{A1}$ that is outside the nostril 12 and bend again along a second angle $54_{A2}$ that is past the internal nasal valve 34 and within the nasal cavity 16. The actual angles for the first and second angles $54_{A1}$, $54_{A2}$ may vary based on a relative position of the illumination device 44. By way of example, each of the first and second angles $54_{A1}$, $54_{A2}$ may be provided in a range from 120 degrees to 50 degrees, or in a range from 130 degrees to 140 degrees. In such embodiments, the first and second angles $54_{A1}$, $54_{A2}$ may be determined based on dimensions of the standardized model described above for FIG. 2C. Additionally, lengths of different portions of the light guide 54 may also be arranged based on dimensions of the standardized model. For example, a first length $54_{L1}$ of the light guide 54 may correspond to a portion that is between the illumination device 44 and the first angle $54_{A1}$ and outside the nostril 12, a second length $54_{L2}$ may correspond to a portion that is between the first angle $54_{A1}$ and the second angle $54_{A2}$ that extends through the nostril 12 and the internal nasal valve 34, and a third length $54_{L3}$ may correspond to a portion that is beyond the second angle $54_{A2}$ and within the nasal cavity 16. In certain embodiments, the third length $54_{L3}$ may be provided in a range from 1 cm to 10 cm, or in a range from 3 cm to 5 cm, or in a range from 3.5 cm to 4.5 cm for providing irradiation to tissues within the nasal cavity 16. Such ranges for the third length $54_{L3}$ may be based on the dimensions provided by the standardized 3D model of FIG. 2C and the targeted tissue for irradiation. For example, a third length $54_{L3}$ at or near 10 cm may allow the distal end of the light guide 54 to extend through a length of the nasal cavity 16 and into the pharynx region, while lower values for the third length $54_{L3}$ may allow the distal end of the light guide 54 to remain within the nasal cavity 16. The first and second lengths $54_{L1}$, $54_{L2}$ may be determined based on a relative position of the illumination device 44 outside the body. In a particular example, the first length $54_{L1}$ may be provided with a similar range as the third length $54_{L3}$ and the second length $54_{L2}$ may be provided in a range that is twice the range of the third length $54_{L3}$. In certain embodiments, the light guide 54 may also be molded with a shape that corresponds to the above-described angles and lengths based on a desired position of the illumination device 44. In this manner, the pre-formed shape allows the light guide 54 to traverse along the upper respiratory tract and the flexible nature of the light guide 54 may allow it to conform to one or more tissues along the upper respiratory tract. In other embodiments where the light guide 54 is formed with a more rigid material, the light guide 54 may also be shaped according to the above-described angles and lengths to traverse along the upper respiratory tract.

FIGS. 5A to 5E illustrate various geometries of the light guide 54 that may be utilized according to principles of the present disclosure. FIG. 5A is a perspective view of at least a portion of the light guide 54. In certain embodiments, the light guide 54 may include a base 60 that is arranged to receive light from one or more light emitters, and the light guide 54 may divide into two extensions 62 for insertion into the nasal cavities accessible from each nostril. The base 60 may include a rectangular or square-shaped cross-section that promotes improved mixing from multiple ones of the light emitters before branching off into the extensions 62. While a square-shaped cross-section is illustrated, the base 60 may include other shapes, such as hexagonal and circular cross-sections. In general, configurations that include one or more flat surfaces and/or facets of the light guide (e.g., square, rectangular, hexagonal, etc.) may promote improved mixing of light. Depending on a number and a size of light emitters, the base 60 may include a diameter $60_D$ or width that is larger than other portions of the light guide 54. By way of example, the diameter $60_D$ may be provided in a range from 7 mm to 10 mm for an array of four light emitters. Larger diameters may also be provided to improve light coupling. In certain embodiments, a light-receiving end 64 of the base 60 may form a shaped inlet to further improve light coupling. For example, the light-receiving end 64 may include one or more curved surfaces that encompass portions of one or more associated light emitters. For illustrative purposes, the light guide 54 in FIG. 5A is shown with break lines to provide a view of the light-receiving end 64 of the base 60 and the extensions 62. In practice, the light guide 54 may be formed with a shape as illustrated in FIG. 3 where the light-receiving end 64 is coupled to the illumination device 44 and the extensions 62 may be provided within corresponding nasal cavities 16.

FIG. 5B is a cross-sectional view of the light guide 54 taken along the sectional line I-I of FIG. 5A. In certain embodiments, the extensions 62 may form a square or rectangular cross-section that is smaller than the cross-section of the base 60, thereby forming paddle-like extensions for delivering light within the nasal cavities. The extensions 62 may be sized to pass along either side of the septum, through the internal nasal valve, and into corresponding nasal cavities. In this regard, a width $62_W$ of the extensions 62 may be sized to comfortably pass through the narrowest portion of the intranasal passageway, such as the internal nasal valve. As previously described for FIG. 2C, a smallest dimension of the internal nasal valve in the standardized 3D model corresponds to a width that is less than 1 cm. In this regard, the width $62_W$ of the extensions 62 may be sized less than 1 cm, or in a range from 0.25 cm to less than 1 cm, or in a range from 0.4 cm to 0.6 cm. A largest dimension or diameter $62_D$ of the extensions 62 may be sized less than 2 cm, for example in a range from 0.5 cm to 1.5 cm. As illustrated, a medial side 66 of each of the extensions 62 may be defined by sides that face one another. In this manner, a spacing $62_S$ between the medial sides 66 may be provided to fit around the septum during insertion. In certain embodiments, the spacing $62_S$ may be sized in a range from 0.7 cm to 1 cm, or in a range from 0.75 cm to 1 cm, or in a range from 0.7 cm to 0.9 cm. Lateral sides 68 of each extension may be defined by sides of the extensions 62 that face away from the medial sides 66. In this manner, the lateral sides 68 may face targeted portions of the nasal cavity during operation. In certain embodiments, it may be desirable to configure the extensions 62 to preferentially pass light 47 from the lateral sides 68 in higher quantities than from the medial sides 66. This may be accomplished by only texturing and/or patterning the lateral sides 68, or by providing increased loading of disperser and/or diffusers along the lateral sides 68, or by providing a surface coating or a partial surface coating on the medial sides 66. The surface and/or partial surface coating may include a coating that may be light reflective, light blocking, spectrum modifying (e.g., specific wavelength filters and/or reflectors, etc.) and various combinations thereof. In this regard, the light 47 that escapes the medial sides 66 may be reduced and/or altered while the light 47 that escapes the lateral sides 68 may be increased and/or enhanced. In a particular example, the lateral sides 68 may be configured to provide at least 60%, or at least 70%, or at least 80% of the light 47 that escapes the light guide 54, with the remaining portions of light 47 either provided through the medial sides 66 and/or distal ends of the extensions 62.

FIG. 5C is a cross-sectional view of the light guide 54 taken along the sectional line I-I of FIG. 5A for embodiments where the extensions 62 may be angled with respect to one another. An angle $62_A$ between the extensions 62 may be formed for ease of insertion through corresponding intranasal passageways accessible from each nostril. The angle $62_A$ may be determined based on the 3D standardized model of nasal cavities described above for FIG. 2C. In certain embodiments, the angle $62_A$ may include a range from 45 degrees to 75 degrees, or a range from 50 degrees to 70 degrees, or a range from 55 degrees to 65 degrees. In certain embodiments, the extensions 62 may be molded with a pre-formed shape that includes the angle $62_A$.

FIG. 5D is a cross-sectional view of an alternative configuration of the light guide 54 taken along the sectional line I-I of FIG. 5A for embodiments where the extensions 62 may form curved shapes that correspond to portions of intranasal passageways. As illustrated, the extensions 62 may form a profile that is curved or an arc shape away from the area defined by the spacing $62_S$. In this manner, the extensions 62 may form shapes that follow contours of nostrils and other nasal passageway sections. As with other embodiments, the width $62_W$ along the curved profile may be configured for passage through the internal nasal valves as previously described.

FIG. 5E is a cross-sectional view of an alternative configuration of the light guide 54 taken along the sectional line I-I of FIG. 5A for embodiments where the extensions 62 may form circular shapes for insertion through intranasal passageways. In certain embodiments, the circular shapes may include a taper that reduces the width $62_W$ (e.g., diameter for circular shapes) with increasing length of the extensions 62. In other embodiments, the width $62_W$ may be constant throughout the length of the extensions 62. As with other embodiments, the width $62_W$ may be configured for passage through the internal nasal valves as previously described.

In various embodiments, light guides of the present disclosure may be formed with materials that may be either hydrophobic or hydrophilic. As used herein, hydrophobic may refer to materials that may repel water and hydrophilic may refer to materials that may be wetted by water. Various advantages may be realized when either hydrophobic or hydrophilic materials are used for light guides of the present disclosure that may come into contact or close proximity with tissues of the upper respiratory tract.

FIGS. 6A and 6B are diagrams 70, 72 illustrating interactions between a light guide 54 formed of a hydrophobic material and corresponding tissue 74 of the upper respiratory tract. As illustrated in the diagram 70 of FIG. 6A, the light guide 54 may be positioned to deliver light to the tissue 74 from one or more light emitters 46. When the light guide 54 is formed of a hydrophobic material, a gap 76, or air gap, may be formed between the tissue 74 and the light guide 54 where mucus or fluids of the nasal cavity may be repelled from surfaces of the light guide 54. In certain embodiments, the gap 76 may facilitate even distribution of light from the light guide 54 for irradiating the tissue 74 with reduced interactions from random distributions of mucous that may otherwise be present. As illustrated in the diagram 72 of FIG. 6B, one or more surfaces 78 of the light guide 54 may be textured and/or patterned to provide further improvements to uniformity of light that passes through the gap 76 to irradiate the tissue 74.

FIGS. 7A and 7B are diagrams 80, 82 illustrating interactions between a light guide 54 formed of a hydrophilic material and corresponding tissue 74 of the upper respiratory tract. As illustrated in the diagram 80 of FIG. 7A, the light guide 54 may be positioned to deliver light to the tissue 74 from one or more light emitters 46. For embodiments where the light guide 54 is formed of a hydrophilic material, mucus 84 or fluids of the nasal cavity may form between the tissue 74 and the light guide 54. When the light guide 54 is suitably wetted, the mucus 84 may serve to more directly couple light from the light guide 54 to the corresponding tissue 74 with improved efficiency. As illustrated in the diagram 82 of FIG. 7B, one or more surfaces 78 of the light guide 54 may be textured and/or patterned to provide further improvements to light distribution uniformity and optical coupling with the mucus 84.

Figure 8:
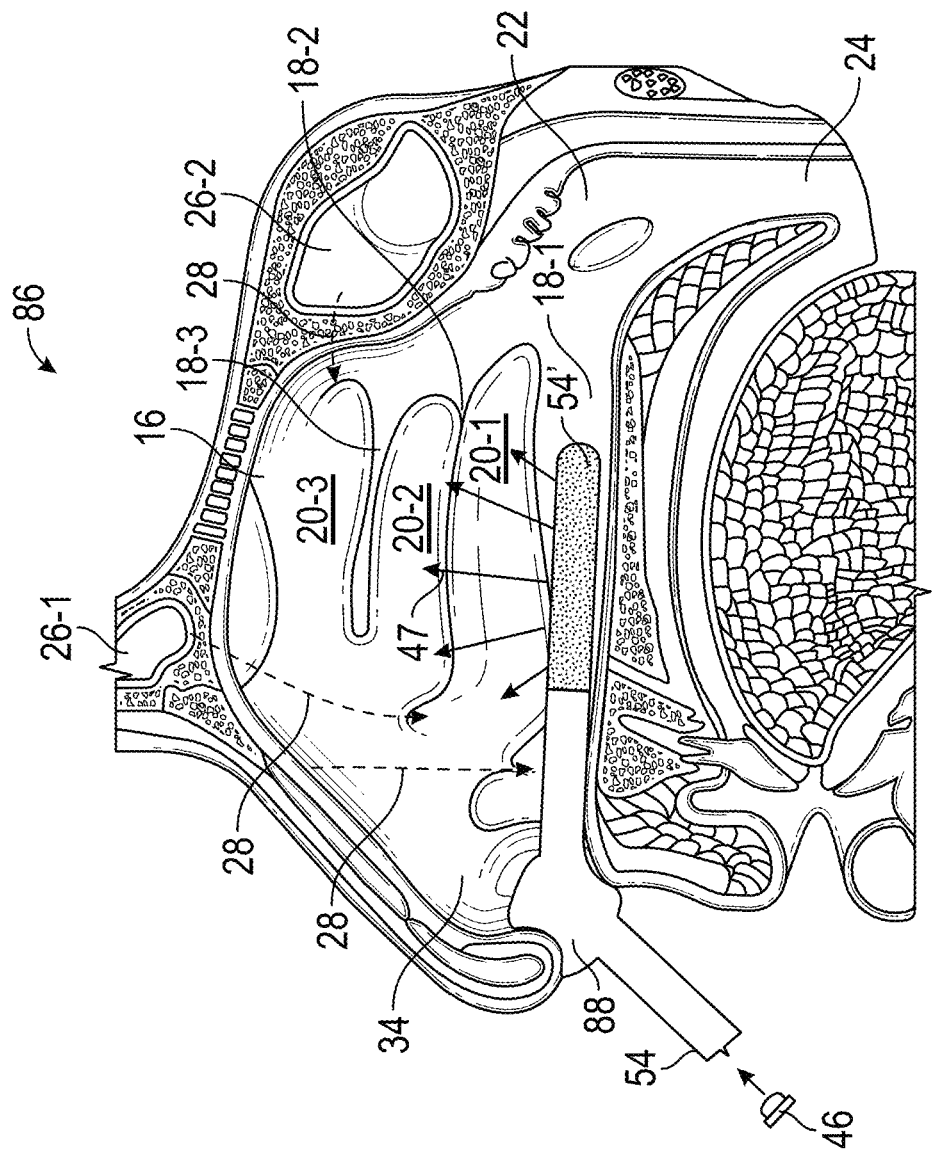
FIG. 8 is a cross-sectional view of an intranasal passageway during light treatment for embodiments where the light guide includes a positioner that is arranged to position the light guide for delivery of light within the nasal cavity.

FIG. 8 is a cross-sectional view of an intranasal passageway 86 during light treatment for embodiments where the light guide 54 includes a positioner 88 that is arranged to position the light guide 54 for delivery of light 47 within the nasal cavity 16. The positioner 88 may be configured to engage with one or more portions of the nostril 12 during use. For example, the positioner 88 may include a deformable material that at least partially deforms to a shape of the nostril 12. In this regard, the positioner 88 may be configured to hold the portions of the light guide 54 in place within the nasal cavity 16. Additionally, the positioner 88 may prevent the light guide 54 from being inserted too far along the intranasal passageway 86 during operation. In certain embodiments, the positioner 88 comprises a same material as the light guide 54. In such embodiments, the positioner 88 may form an integral single piece that is continuous with other portions of the light guide 54. In other embodiments, the positioner 88 may be a separate element that is attached or otherwise affixed to the light guide 54. In these embodiments, the positioner 88 may comprise a same or even a different material than the light guide 54. While the positioner 88 is illustrated with a deformable bulb shape in FIG. 8, the positioner 88 may form other shapes, including a flange that abuts the nostrils 12 or one or more clips that attach to the nostrils 12 without deviating from the principles of the present disclosure. The light guide 54 of FIG. 8 may be arranged to couple with the illumination device as previously described for FIG. 3.

Light guides of the present disclosure may form various configurations that allow therapeutic delivery of light within or through intranasal passageways. In addition to previously described embodiments where light guides may couple with light emitters of hand-held illumination devices, light guides of the present disclosure may be arranged to provide direct emissions from light emitters to target tissues within or through intranasal passageways. In this manner, light emitters may be positioned at or within the nostrils or even along portions of the light guide that pass within or through nasal cavities. Additionally, light guides may be provided with suitable lengths for intranasal delivery of doses of light to the nasopharynx and/or oropharynx.

Figure 9A:
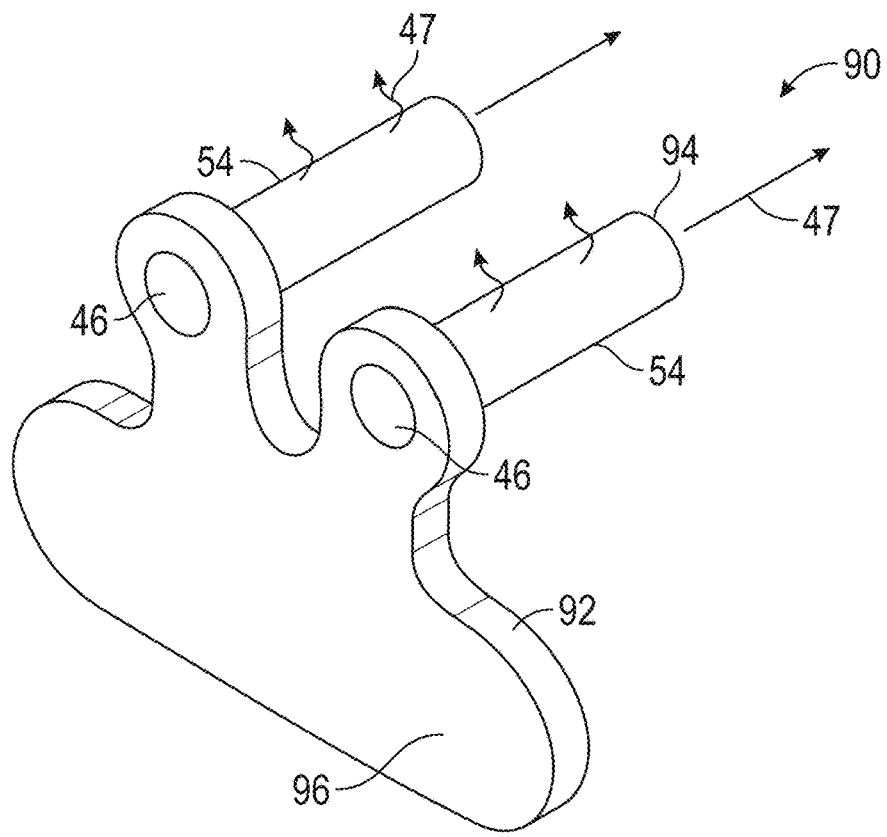
FIG. 9A is a perspective view of an illumination device that is configured to provide direct emission from one or more light emitters to targeted tissues within or through intranasal passageways.
Figure 9B:
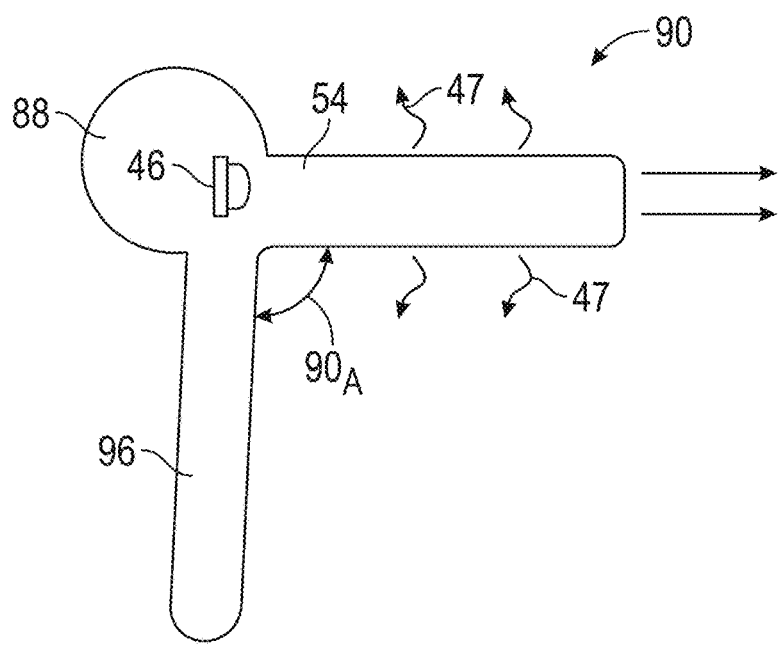
FIG. 9B is side view of the illumination device of FIG. 9A that includes first and second positioners for securing the illumination device in place.

FIG. 9A is a perspective view of an illumination device 90 that is configured to provide direct emission from one or more light emitters 46 to targeted tissues within or through intranasal passageways. The illumination device 90 may include a housing 92 that includes the light emitters 46 and a pair of light guides 54 that are optically coupled to the light emitters 46. In certain embodiments, the light emitters 46 are arranged to directly emit light 47 into the light guides 54 and have at least some light 47 directly exit the light guides 54 at primary emission surfaces 94 formed by ends of the light guides 54 that are distal to the light emitters 46. In this manner, the primary emission surfaces 94 may direct the light 47 toward a target tissue. This may be accomplished without substantial bending of the light guides 54. As previously described, the light guides 54 may include material that is intentionally somewhat leaky, thereby allowing some light 47 to escape laterally along the light guide 54 to irradiate other tissues. The light guides 54 may be arranged with a spacing between the light guides 54 and any of the shapes as previously described for FIGS. 5B-5E to allow improved insertion within a pair of nostrils. The housing 92 may further form a positioner 96 that resides outside of the nostrils during use. The positioner 96 may form a flange or plate that is configured to engage with one or more external surfaces of a user's face during use. For example, the positioner 96 may reside between the nose and mouth along the face of a user to secure the light guides 54 in place. FIG. 9B is side view of the illumination device 90 of FIG. 9A that includes first and second positioners 88, 96 for securing the illumination device 90 in place. As illustrated, the illumination device 90 may include the first positioner 88 as previously described for FIG. 8 and the second positioner 96 as described for FIG. 9A. As illustrated in FIG. 9B, the light emitters 46 may be arranged to provide direct emissions through the primary emission surfaces 94 and toward targeted tissues of the upper respiratory tract. In this regard, the light emitters 46 may be oriented such that highest intensities of emissions are aligned in directions that point directly toward the primary emission surfaces 94. An angle $90_A$ for the illumination device 90 may be defined between the positioner 96 and the light guides 54. In various embodiments, the angle $90_A$ may be determined based on geometries of user faces and the angle $90_A$ may be provided in a range from 70 degrees to 110 degrees, although other angles are possible.

Figure 9C:
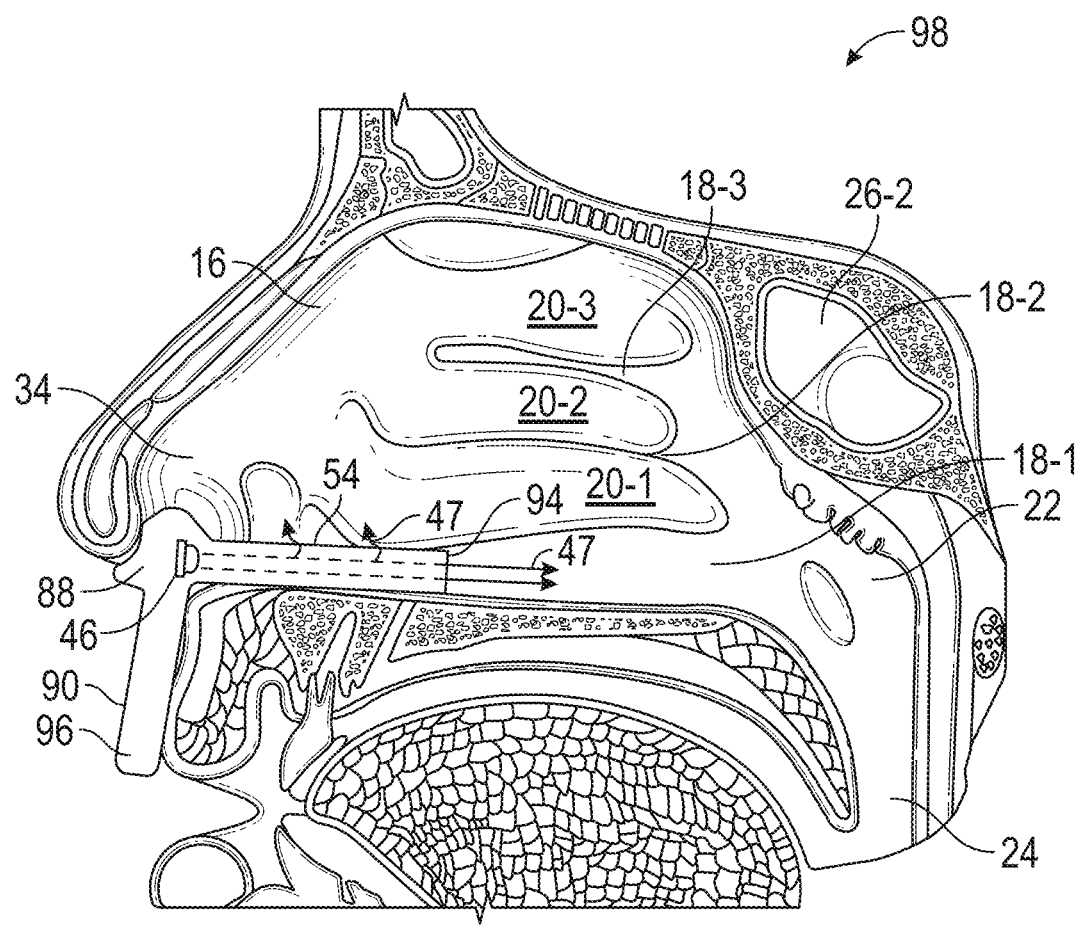
FIG. 9C is a cross-sectional view of an intranasal passageway during light treatment with the illumination device of FIGS. 9A and 9B.

FIG. 9C is a cross-sectional view of an intranasal passageway 98 during light treatment with the illumination device 90 of FIGS. 9A and 9B. As illustrated, one or more of the positioners 88, 96 may serve to secure the illumination device 90 so that the primary emission surface 94 is oriented in a direction that targets the nasopharynx 22 and/or the oropharynx 24. In various embodiments, the illumination device 90 may include a single one of the positioners 88, 96 or both of the positioners 88, 96. As illustrated, while light 47 is primarily directed toward the nasopharynx 22 and/or the oropharynx 24, the leaky nature of the light guides 54 may allow a portion of the light to irradiate tissues of the nasal cavity 16.

Figure 10:
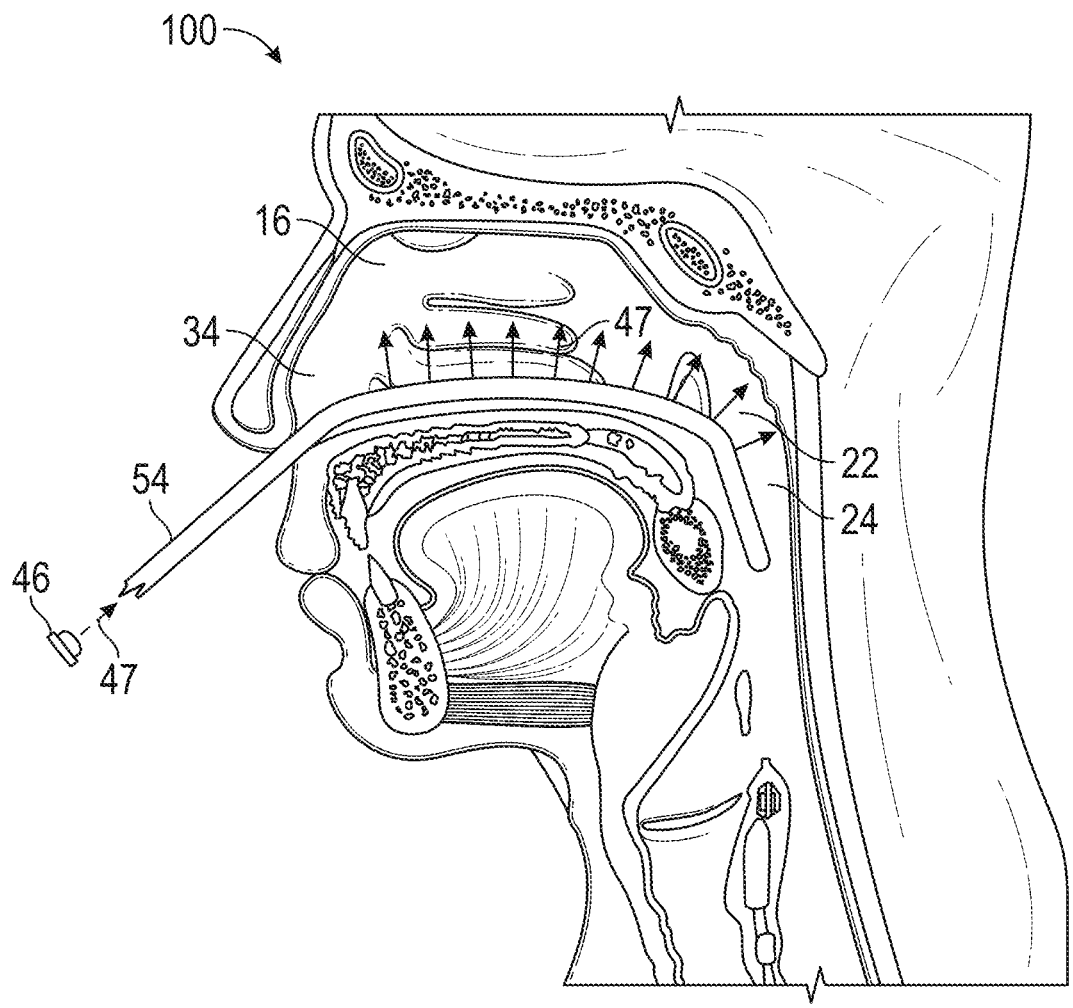
FIG. 10 is a cross-sectional view illustrating a light guide with a suitable length for intranasal delivery of light doses to the nasopharynx and/or oropharynx by way of an intranasal passageway.

FIG. 10 is a cross-sectional view illustrating a light guide 54 with a suitable length for intranasal delivery of light doses to the nasopharynx 22 and/or oropharynx 24 by way of an intranasal passageway 100. As illustrated, the light guide 54 may be arranged to receive light 47 from the light emitter 46 and extend to a position that provides at least one emission surface of the light guide 47 that is past the nasal cavity 16 and adjacent the nasopharynx 22 and/or oropharynx 24. As previously described, the light guide 54 may comprise a flexible and bendable material for traversing the intranasal passageway 100. In certain embodiments, the light guide 54 may form a relatively straight shape before insertion into the nostril 12 and the light guide 54 may responsively bend and deform to various geometries of the intranasal passageway 100. As illustrated, the light guide 54 may be configured to provide light 47 along the nasal cavity 16 and to the nasopharynx 22 and/or oropharynx 24. In other embodiments, one or more light emitters 46 may be positioned within the portions of the light guide 54 that traverse the intranasal passageway 100, in place of or in combination with light emitters 46 that are positioned near or outside the nostril 12 during operation. For example, the portion of the light guide 54 that is past the nasal cavity 16 and adjacent the nasopharynx 22 and/or oropharynx 24 may include one or more light emitters 46 for providing more directed emissions to the nasopharynx 22 and/or oropharynx 24.

Figure 11A:
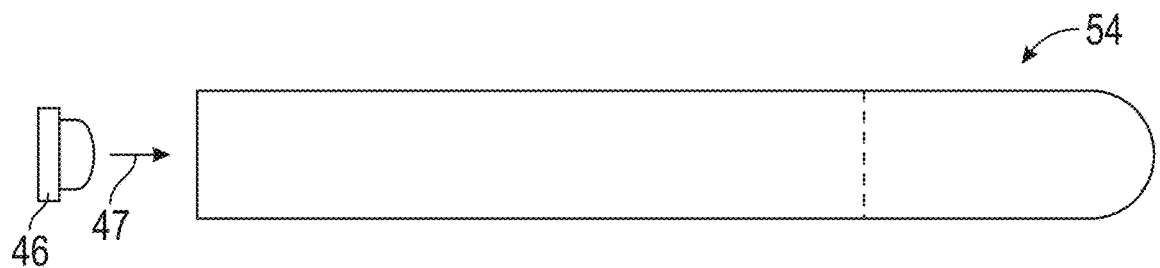
FIG. 11A is a side view of an exemplary light guide that may initially be provided with a straight shape that responsively bends and/or deforms along various geometries of intranasal passageways.
Figure 11B:
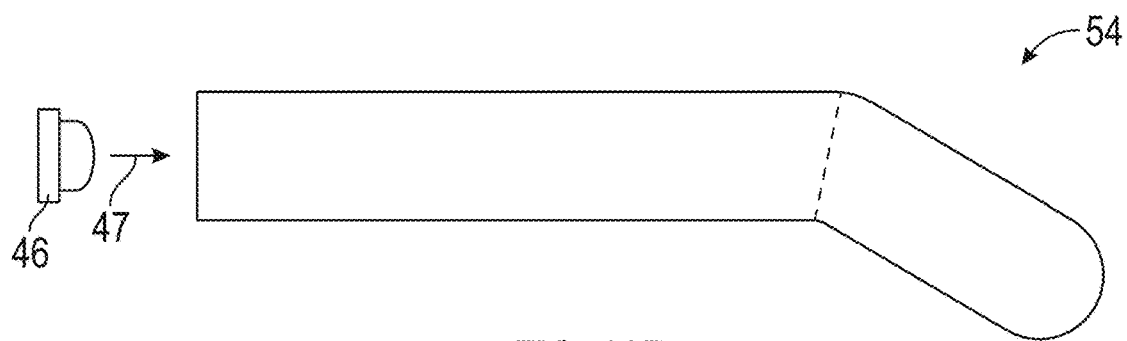
FIG. 11B is a side view of the light guide of FIG. 11A after bending and/or deforming in response to insertion within or through an intranasal passageway.

FIGS. 11A and 11B illustrate side views of light guides 54 that may initially be provided with relatively straight shapes that responsively bend and deform along various geometries of intranasal passageways. In FIG. 11A, one or more portions of the light guide 54 may be formed with an initial shape that is straight. FIG. 11B represents the light guide 54 of FIG. 11A as it deforms and/or bends along a superimposed dashed line during use in response to insertion within or through an intranasal passageway. While only a single bend is shown for illustrative purposes, the light guide 54 may be configured to flexibly bend along many different portions of the light guide 54 in practice. As previously described, the light guide 54 may comprise a flexible material with suitable dimensions for responsive bending along a circuitous pathway.

Figure 12A:
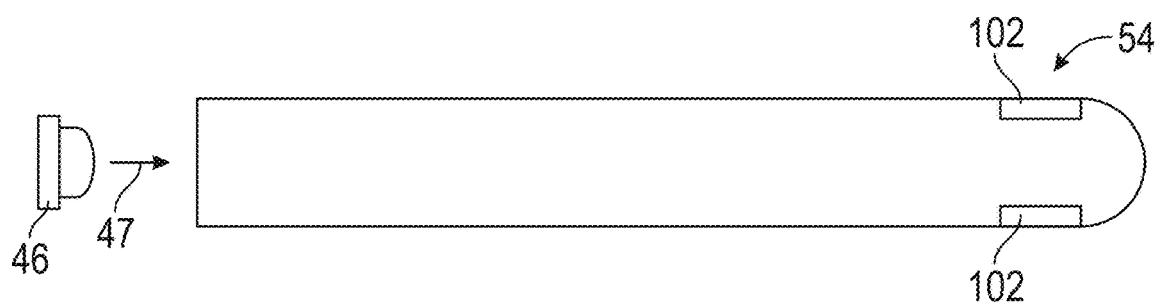
FIG. 12A is a side view of an exemplary light guide that may include guiding features that contribute to bending and/or deforming along various geometries of intranasal passageways in a controlled manner.
Figure 12B:
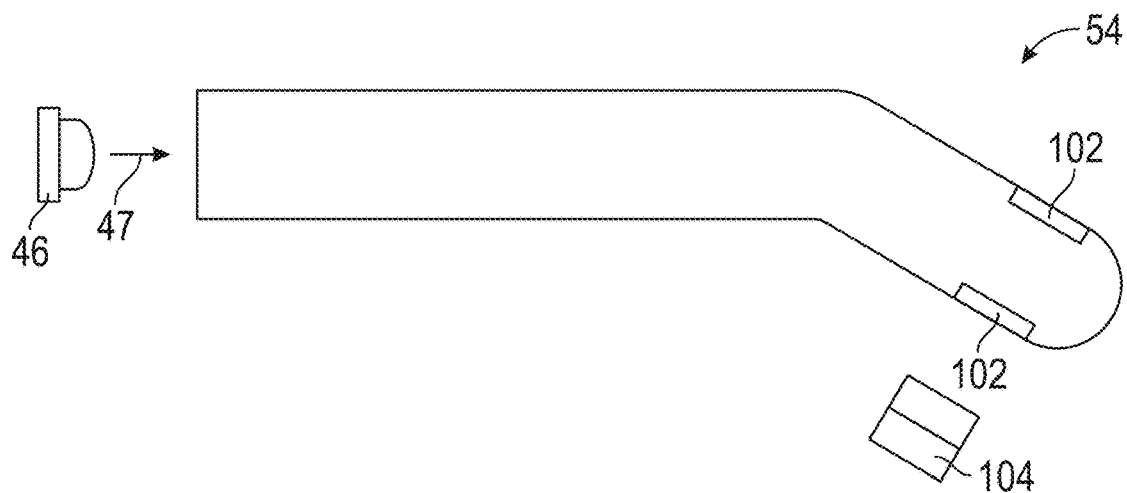
FIG. 12B is a side view of the light guide of FIG. 12A after bending and/or deforming in a controlled manner.

FIGS. 12A and 12B illustrate side views of light guides 54 that may comprise guiding features that contribute to bending and deforming along various geometries of intranasal passageways in a controlled or desired manner. In FIG. 12A, one or more portions of the light guide 54 may include one or more guiding features 102. In certain embodiments, the guiding features 102 may embody one or more materials that may be used to steer portions of the light guide 54 in a desired manner. For example, the guiding features 102 may comprise metal that is embedded within the light guide 54.

In FIG. 12B, the light guide 54 of FIG. 12A may deform and/or bend during insertion in response to positioning of a magnet 104 in close proximity to the guiding features 102. In certain embodiments, the magnet 104 may be positioned outside of a user's body to guide the light guide 54 in a desired direction. In certain embodiments, the guiding features 102 may provide extra weight that helps keep the light guide 54 along lower portions of a nasal cavity and/or to portions of the nasopharynx and/or oropharynx. While only a single bend is shown for illustrative purposes, the light guide 54 may be configured to flexibly bend along many different portions of the light guide 54 in practice.

Figure 13:
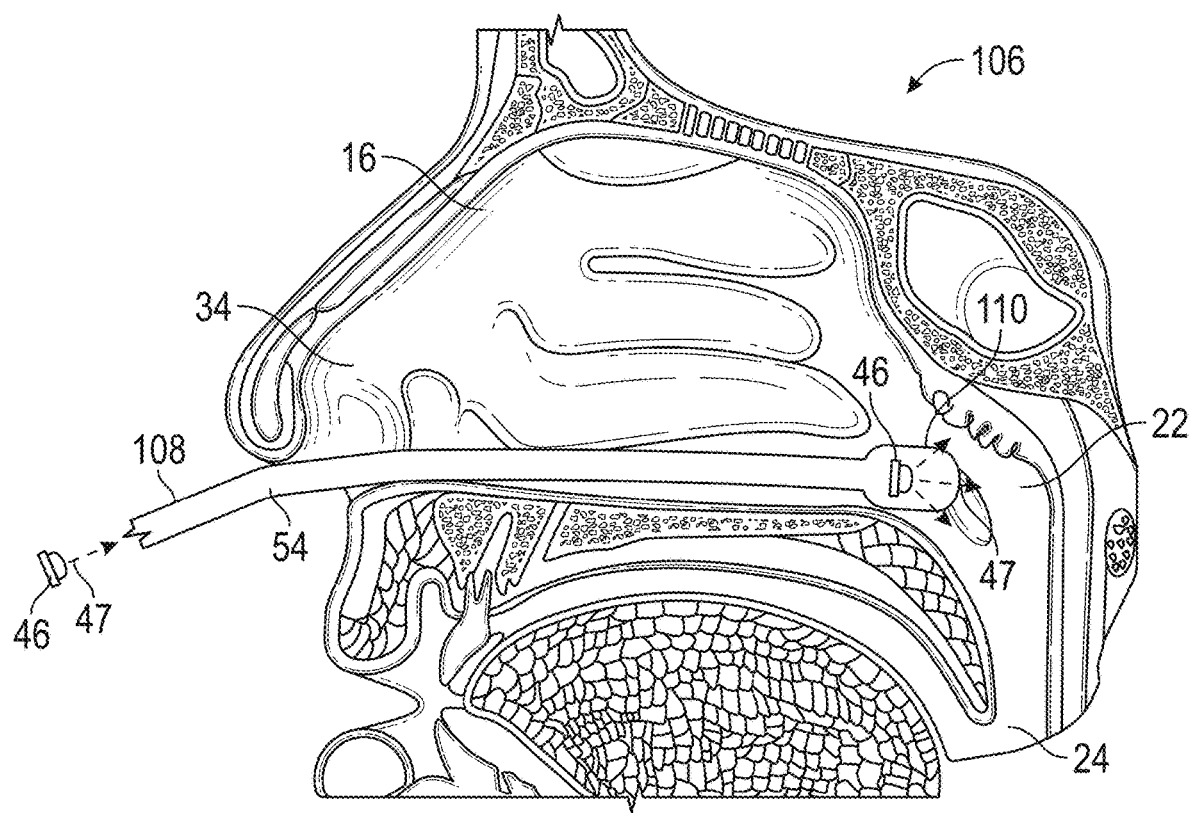
FIG. 13 is a cross-sectional view of an intranasal passageway during light treatment for embodiments where an illumination device is configured to extend past the nasal cavity for delivery of light to the nasopharynx and/or oropharynx.

FIG. 13 is a cross-sectional view of an intranasal passageway 106 during light treatment for embodiments where an illumination device 108 is configured to extend past the nasal cavity 16 for delivery of light 47 to the nasopharynx 22 and/or oropharynx 24. The illumination device 108 and/or light guide 54 may form a shape similar to an elongated swab stick. In this manner, a distal end 110 of the illumination device 108 and/or light guide 54 may form an expanded cross-sectional shape compared with other portions of the illumination device 108 and/or light guide 54 that are within the nasal cavity 16. In this manner, the distal end 110 may include an un-deformed shape that corresponds with an opening of the intranasal passageway 106 at the nasopharynx 22. The material of the distal end 110 may allow the deformation to ease passage through narrower portions of the intranasal passageway 106 before returning to the expanded shape at or near the nasopharynx 22. In certain embodiments, light emitters 46 may be positioned in the distal end 110, outside the nostrils 12, or in both positions.

Figure 14A:
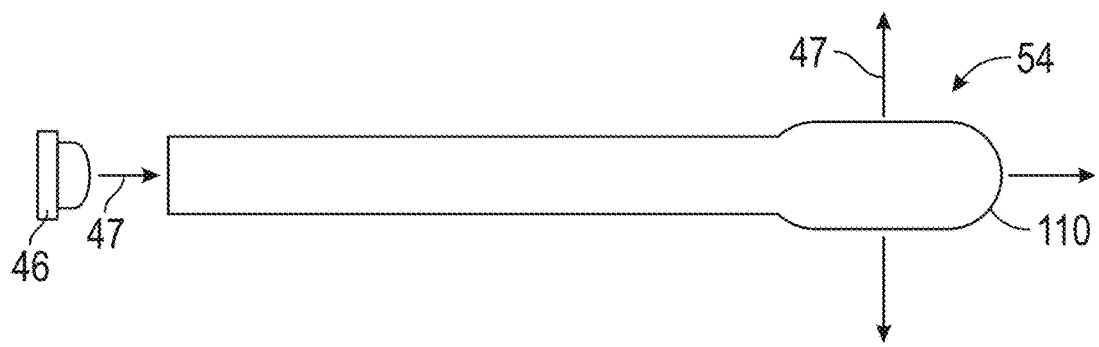
FIG. 14A is a side view of a light guide where a distal end of the light guide is initially formed with a narrow shape that may expand after passing through narrow portions of intranasal passageways.
Figure 14B:
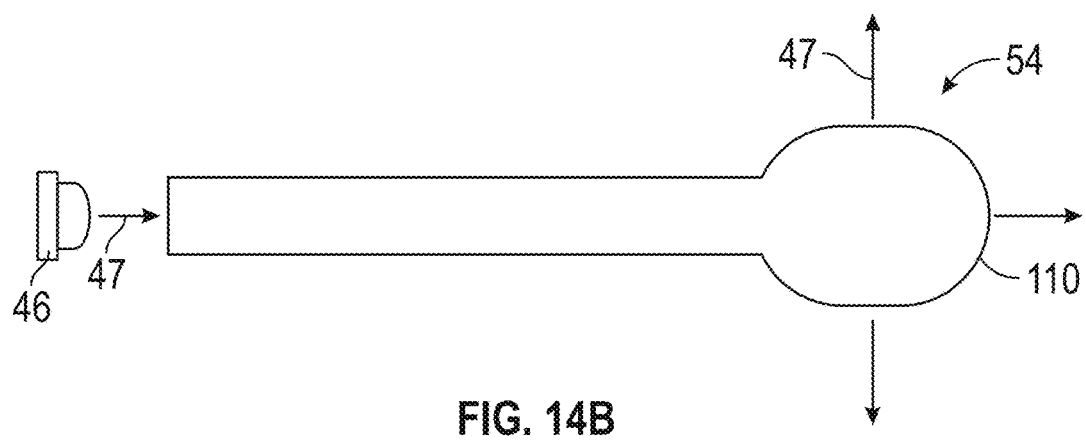
FIG. 14B is a side view of the light guide of FIG. 14A after expansion of the distal end.

FIGS. 14A and 14B illustrate side views of light guides 54 that may include distal ends 110 that may be configured to expand after passing through narrow portions of intranasal passageways. As illustrated in FIG. 14A, the distal end 110 of the light guide 54 may initially form with a narrow shape. When inserted into a narrow portion of the intranasal passageway, light 47 may be provided through the distal end 110 if desired. As illustrated in FIG. 14B, after passing through the narrow portion of the intranasal passageway, the distal end 110 may be configured to expand to a larger shape that provides extra surface area for irradiating light 47 to targeted tissue. In certain embodiments, expansion of the distal end 110 may occur due to selection of a deformable material for the light guide 54. In other embodiments, the light guide 54 may be configured to be inflatable with fluid and/or air that may be bounded within portions of the light guide 54. When fluid is present within the light guide 54, the fluid may further enhance light propagation for light 47 through the light guide 54.

Figure 15:
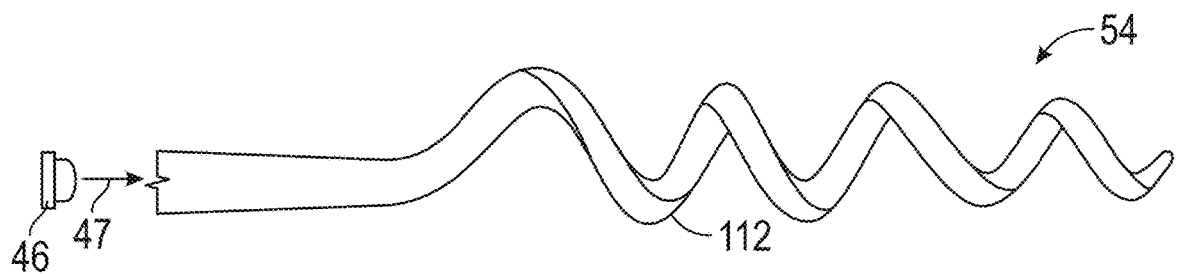
FIG. 15 is a side view of a light guide that includes a spiral section according to principles of the present disclosure.

FIG. 15 is a side view of a light guide 54 that includes a spiral section 112 according to certain embodiments. As illustrated, a portion of the light guide 54 may have a shape that forms the spiral section 112. The spiral section 112, which may also be referred to as having a corkscrew shape, may be provided with a width that tapers in a direction away from the light emitter 46. In particular arrangements, the spiral section 112 may be provided at a distal end of the light guide 54 relative to the light emitter 46. As previously described, the light guide 54 may be formed with a flexible material that provides bending and deformation to allow the light guide 54 to follow circuitous paths of intranasal passageways during insertion. The spiral section 112 of the light guide 54 may further provide enhanced flexibility for the light guide 54 to pass through various narrow portions of intranasal passageways. Additionally, the spiral section 112 may provide increased surface area of the light guide 54 within the nasal cavity, thereby providing enhanced coverage of light that may irradiate corresponding tissue. While only the distal portion of the light guide 54 is illustrated with the spiral section 112 in FIG. 15, the spiral section 112 may encompass at least half of the light guide 54, or even the entire portion of the light guide 54 that is intended for insertion within intranasal passageways.

Figure 16:
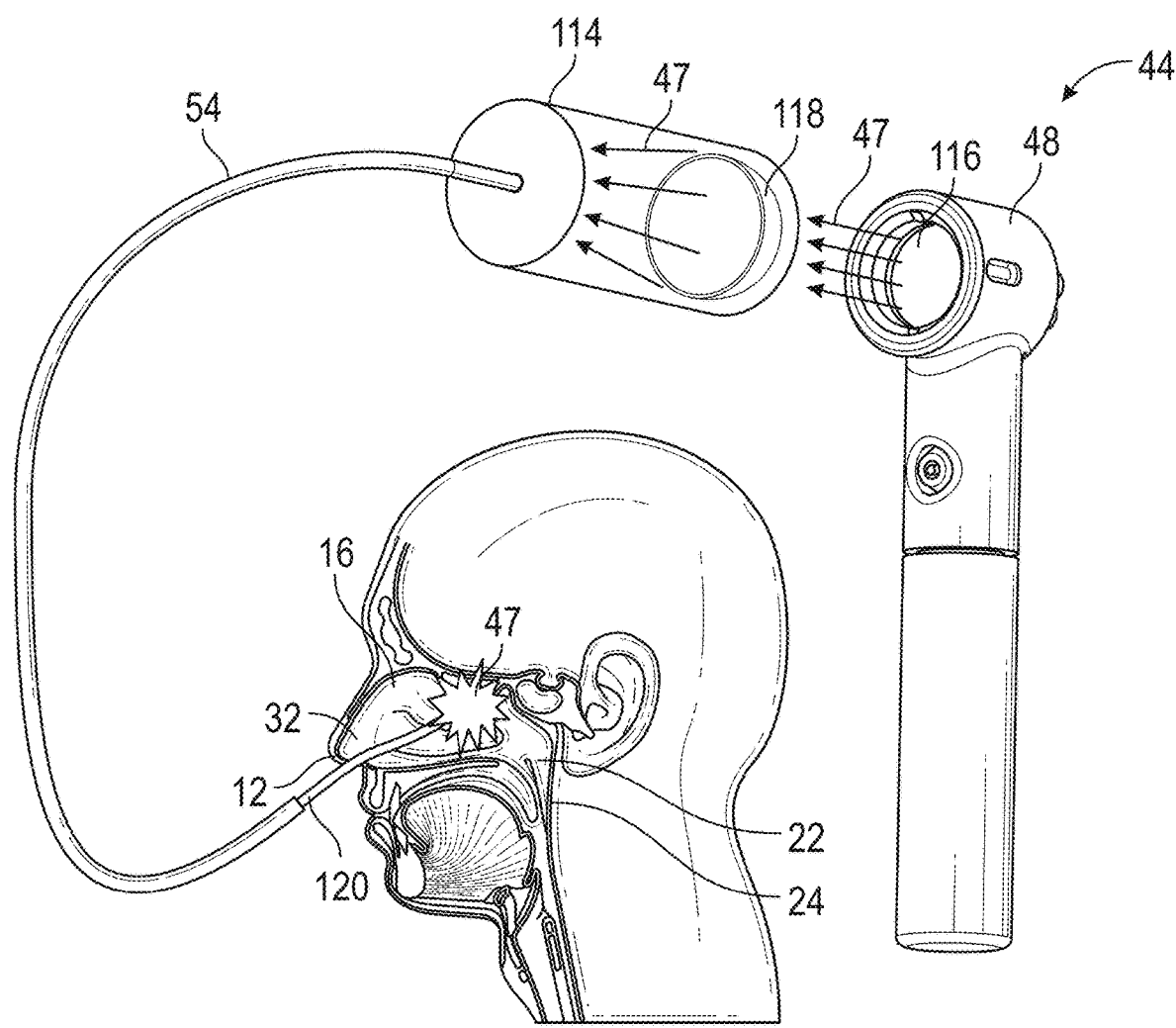
FIG. 16 is a perspective view of an optical tube that may be configured to couple light from the illumination device to the light guide according to principles of the present disclosure.

FIG. 16 is a perspective view of an optical tube 114 that may be configured to couple light 47 from the illumination device 44 to the light guide 54 according to principles of the present disclosure. For illustrative purposes, the optical tube 114 and the illumination device 44 are shown in exploded view over a user. In practice the optical tube 114 may be coupled to the illumination device 44 by way of a releasably-attached mechanical connection, including but not limited to a securing tab, a threaded connection, a spring-clip, and a push-pin connection, among other possibilities. Accordingly, the illumination device 44 may be retro-fitted with the optical tube 114 or any other form of light delivery structure for targeting other body tissues and cavities for a variety of applications. In certain embodiments, a first lens 116 may be provided within the housing 48 of the illumination device 44 to provide collimated light 47 from the light sources within the illumination device 44. The optical tube 114 may include a second lens 118 that focuses the light 47 for launching into the light guide 54. In this regard, the light 47 may be collected from a larger diameter beam that exits the first lens 116 and directed into a smaller diameter beam for delivery to the narrower light guide 54. In certain embodiments, the first lens 116 may comprise a convex outer surface relative to the light source of the illumination device 44 and the second lens 118 may comprise a concave outer surface relative to the light source of the illumination device 44. In other embodiments, the first lens 116 may be omitted while the second lens 118 is provided within the optical tube 114 for narrowing the beam diameter of the light 47. The optical tube 114 may comprise a rigid and hollow plastic tube, or the like.

As illustrated in FIG. 16, such an arrangement for the optical tube 114 may be well suited for embodiments where the light guide 54 comprises an optical fiber, or an optical fiber bundle. A diameter of the light guide 54 may be less than 1 cm, or less than 0.5 cm to provide suitable dimensions for delivery of the light 47 through the nostril 12, the nasal valve 32, and within the nasal cavity 16 of the user. In embodiments where the light guide 54 comprises a structure, such as an optical fiber or the like, that may be too flexible for reliable insertion to the nasal cavity 16, a light delivery structure 120 may be attached to the light guide 54. The light delivery structure 120 may include any type of light guide structure that provides more rigidity than an optical fiber. For example, the light delivery structure 120 may comprise glass, polycarbonate, a metal encased tube, or even the silicone material as described above for FIG. 3. In this manner, the light delivery structure 120 may be provided with a pre-formed structure with one or more bends that allow insertion through the nostril 12, nasal valve 32, and at least into the nasal cavity 16 and optionally to the nasopharynx 22 and/or oropharynx 24. The light delivery structure 120 may comprise a rigid structure or deformable structure that may conform to one or more tissues within the nasal cavity 16.

Figure 17:
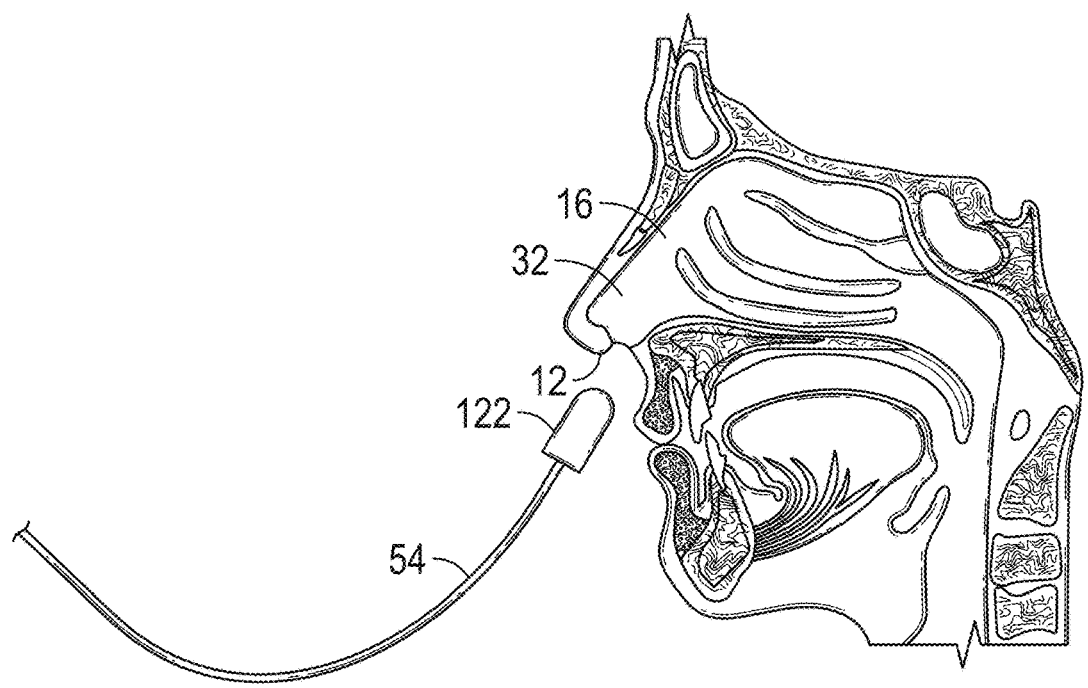
FIG. 17 is a view of the light guide for embodiments that include a removable tip for insertion within or beyond the nasal cavity of a user.

FIG. 17 is a view of the light guide 54 for embodiments that include a removable tip 122 for insertion within or beyond the nasal cavity 16 of a user. The removable tip 122 may be attached to the end of the light guide 54 by way of a tab, a sleeve, or a threaded connection, among others. In certain embodiments, the removable tip 122 comprises a material such as silicone, glass, or plastic that allows light propagating through the light guide 54 to pass through the removable tip 122 and toward targeted tissues during use. After use, the removable tip 122 may be replaced or even cleaned between uses.

Figure 18A:
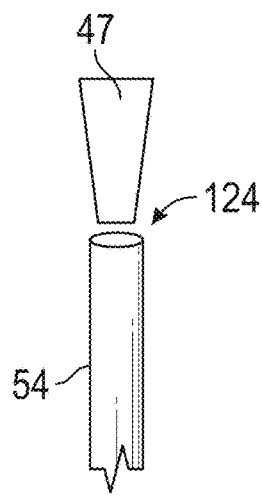
FIG. 18A is a view of a tip geometry for a light guide, a light delivery structure, or a removable tip that may be used to direct some light in a desired direction.
Figure 18B:
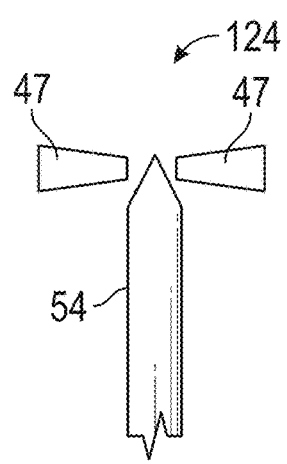
FIG. 18B is a view of a tip geometry for a light guide, a light delivery structure, or a removable tip that may be used to direct some light in multiple lateral or radial directions.
Figure 18C:
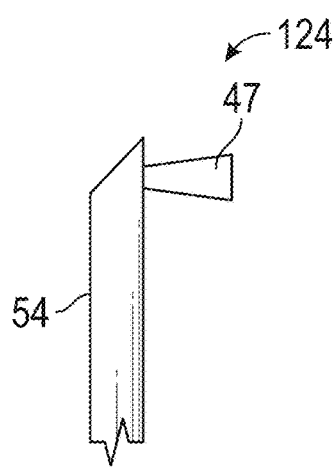
FIG. 18C is a view of a tip geometry for a light guide, a light delivery structure, or a removable tip that may be used to direct some light in at least one lateral or radial direction.

FIGS. 18A-18C illustrate various geometries for tips 124 or ends of light guides that may be used to direct light in desired directions during use. In each of FIGS. 18A-18C, the tips 124 are illustrated as ends of corresponding light guides 54. In other embodiments, the tips 124 may represent ends of any of the previously described light delivery structures 120 of FIG. 16 and/or the removable tips 122 of FIG. 17. As illustrated in FIG. 18A, the tip 124 comprises a flat surface that may direct some light 47 in a direction that generally corresponds to a length of the light guide 54. In FIG. 18B, the tip 124 is illustrated with a triangular cross-section that directs some light 47 in multiple lateral or radial directions from the light guide 54. For example, the tip 124 of FIG. 18B may embody a cone shape or a pyramid shape with multiple angled surfaces. In FIG. 18C, the tip 124 is provided with a triangular cross-section that may preferentially direct some light 47 along one or more certain lateral directions. For example, the tip 124 may be arranged with one or more angled surfaces so that the light 47 is directed disproportionately in certain lateral or radial directions.

FIG. 19 is a side view of a portion of an exemplary illumination device 126 where the light guide 54 is configured to provide different light wavelengths out of one or more selected portions of the light guide 54. The light guide 54 may include one or more light-selective features 128-1, 128-2 that preferentially allow certain wavelengths of light to pass through the light guide 54 while restricting other wavelengths of light. In certain embodiments, the light-selective features 128-1, 128-2 may include one or more combinations of light filters, such as bandpass filters, bandstop filters, absorptive filters, dichroic filters, and wavelength selective reflectors. In certain embodiments, the light-selective features 128-1, 128-2 may include lumiphoric materials that promote wavelength conversion, alone or in combination with any of the above-described light filters. The light-selective features 128-1, 128-2 may be provided along one or more portions of the light guide 54 that correspond with emission surfaces of the light guide 54, including within the light guide 54 and/or as a coating on portions of emission surfaces of the light guide 54. The light-selective features 128-1, 128-2 may be implemented with the medial sides 66 and lateral sides 68 arrangements as previously described for FIG. 5B.

By way of example, the illumination device 126 of FIG. 19 may be configured to receive a first light source 46-1 configured to provide light 47-1 having a first peak wavelength and a second light source 46-2 configured to provide light 47-2 having a second peak wavelength that is different than the first peak wavelength. The light guide 54 may include a mixing section 130 where the first and second peak wavelengths may be mixed before traversing a length of the light guide 54. A first light-selective feature 128-1 may be provided along a length of an emission surface of the light guide 54, and the first light-selective feature 128-1 may be configured to preferentially allow the light 47-1 having the first peak wavelength to pass through while reflecting and/or absorbing the light 47-2 having the second peak wavelength. When present, a second light-selective feature 128-2 may be provided in a different location of the light guide 54 than the first light-selective feature 128-1. For example, the second light-reflective feature 128-2 may be provided within and near a distal end of the light guide 54. The second light-selective feature 128-2 may be configured to preferentially allow the light 47-2 having the second peak wavelength to pass through while reflecting and/or absorbing the light 47-1 having the first peak wavelength. As illustrated, other portions of the light guide 54 that are devoid of the light-selective features 128-1, 128-2 may allow light 47-1, 47-2 of both peak wavelengths to escape the light guide 54. In a particular example, the light 47-1 of the first peak wavelength may include red or NIR light and the light 47-2 of the second peak wavelength may include blue light. When inserted within a nasal cavity, the first light-selective feature 128-1 may accordingly allow red light to be directed to tissue within the nasal cavity while the second light-selective feature 128-2 may allow blue light to be directed toward the pharynx region, including the nasopharynx and/or the oropharynx. In addition to the example illustrated in FIG. 19, various embodiments may include one or more combinations of light-selective features in various configurations along the light guide 54 to preferentially provide any of the previously described wavelength ranges out of the light guide 54. In certain aspects, one or more light-selective features may include filters that narrow the FWHM of light for tissue safety purposes. For example, light-selective features may be arranged to reflect and/or absorb UV potions of light from reaching targeted tissues in certain embodiments.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. An illumination device comprising:
   at least one light source;
   a housing, wherein the at least one light source is positioned within the housing;
   driver circuitry configured to drive the at least one light source;
   a light guide that is optically coupled to the at least one light source, the light guide comprising a material that forms a light transmitting portion and a light emitting portion such that at least a portion of light from the at least one light source propagates in the material in a direction defined by the light transmitting portion and exits the light guide through the light emitting portion, the light guide being configured to extend through a nostril and an internal nasal valve of a user to position the light emitting portion of the light guide within a nasal cavity of the user; and
   a connector configured to engage the housing and removably attach the light guide to the housing;
   wherein the material of the light guide at the light emitting portion forms a light extraction section that comprises: disperser materials, and lateral sides of the light extraction section that are loaded with a higher concentration of the disperser materials relative to the remainder of the light guide.

2. The illumination device of claim 1, wherein the at least one light source is positioned outside the nostril of the user.

3. The illumination device of claim 1, wherein the housing includes the driver circuitry.

4. The illumination device of claim 1, wherein the connector is configured to removably attach the light guide to the housing by at least one of a securing tab, a threaded connection, a spring-clip, and a push-pin connection.

5. The illumination device of claim 1, wherein the light guide is configured to bend between the nostril and portions of the nasal cavity during use.

6. The illumination device of claim 1, wherein the material of the light guide is a molded material with a pre-formed shape that includes a bend that resides between the nostril and portions of the nasal cavity during use.

7. The illumination device of claim 6, wherein a length of the light guide between the bend and a distal end of the light guide is provided in a range from 1 centimeter (cm) to 10 cm.

8. The illumination device of claim 7, wherein the length of the light guide between the bend and the distal end of the light guide is provided in a range from 3 cm to 5 cm.

9. The illumination device of claim 1, wherein the material of the light guide is a flexible material for traversing the nostril and internal nasal valve during insertion.

10. The illumination device of claim 1, wherein the light guide comprises silicone.

11. The illumination device of claim 1, wherein an index of refraction of the light guide at 589.3 nm is in a range from greater than 1.33 to 1.8.

12. The illumination device of claim 1, wherein the light guide comprises two extensions that extend from a base of the light guide and the two extensions are configured for simultaneous insertion into both nostrils and corresponding nasal cavities of the user.

13. The illumination device of claim 12, wherein a width of the two extensions decreases in a direction toward a distal end of the light guide.

14. The illumination device of claim 12, wherein a width of each of the two extensions is in a range from 0.25 cm to less than 2 cm.

15. The illumination device of claim 12, wherein the two extensions are spaced from one another by a distance in a range from 0.7 cm to 1 cm.

16. The illumination device of claim 12, wherein the two extensions are angled with respect to one another by an angle that is in a range from 45 degrees to 75 degrees.

17. The illumination device of claim 12, wherein the base of the light guide comprises a rectangular or square-shaped cross-section and the two extensions comprise rectangular or square-shaped cross-sections that are smaller than the cross-section of the base.

18. The illumination device of claim 12, wherein the two extensions form arc-shapes that at least partially conform to the nostrils of the user.

19. The illumination device of claim 12, wherein medial sides of each of the two extensions are formed where the two extensions face one another, and the medial sides are configured to extract less light from the light guide than other sides of the two extensions.

20. The illumination device of claim 1, wherein the material of the light guide is a hydrophobic material that is configured to repel mucus within the nasal cavity.

21. The illumination device of claim 1, wherein the material of the light guide is a hydrophilic material that is configured to allow portions of the light guide to be wetted by mucus within the nasal cavity.

22. The illumination device of claim 1, wherein the light guide comprises a positioner that is configured engage with one or more portions of the nostril during use.

23. The illumination device of claim 1, wherein at least a portion of the light guide forms a spiral shape.

24. The illumination device of claim 1, wherein the at least one light source is configured to provide light with a first peak wavelength that induces at least one biological effect, the at least one biological effect comprising one or more of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect.

25. The illumination device of claim 24, wherein the first peak wavelength is in a range from 400 nm to 450 nm.

26. The illumination device of claim 24, wherein the first peak wavelength is in a range from 385 nm to 450 nm.

27. The illumination device of claim 24, wherein the at least one light source is configured to provide light with a second peak wavelength that is different than the first peak wavelength.

28. The illumination device of claim 27, wherein the first peak wavelength is in a range from 385 nm to 450 nm and the second peak wavelength is in a range from 620 nm to 1,000 nm.

29. The illumination device of claim 1, further comprising a light-selective feature that is arranged on or within a portion of the light guide, the light-selective feature being configured to preferentially allow certain wavelengths of light to pass through the light guide while restricting other wavelengths of light.

30. The illumination device of claim 1, further comprising a first positioner that forms a bulb shape configured to deform to the nostril while positioning the light guide to provide directed emissions toward at least one of a nasopharynx and an oropharynx of the user.

31. The illumination device of claim 30, wherein a distal end of the light guide is configured to reside within a nasal cavity of the user and a primary emission surface of the light guide is oriented in a direction toward at least one of the nasopharynx and the oropharynx.

32. The illumination device of claim 31, wherein the light guide is configured to provide at least a portion of light for irradiating tissue within the nasal cavity.

33. The illumination device of claim 32, wherein the first positioner comprises a different material than the light guide.

34. The illumination device of claim 33, wherein the light guide further comprises a second positioner that is configured to engage with one or more surfaces between the nostril and a mouth of the user.

35. The illumination device of claim 30, wherein the at least one light source is arranged such that highest intensities of light emissions that exit the at least one light source are aligned in a direction that points directly toward at least one of the nasopharynx and the oropharynx.

36. An illumination device comprising:
at least one light source;
driver circuitry configured to drive the at least one light source; and
a light guide that is optically coupled to the at least one light source, the light guide comprising a material that forms a light transmitting portion and a light emitting portion such that at least a portion of light from the at least one light source propagates in the material in a direction defined by the light transmitting portion and exits the light guide through the light emitting portion, the light guide being configured to extend through a nostril and an internal nasal valve of a user to position the light emitting portion of the light guide within a nasal cavity of the user;

wherein the material of the light guide at the light emitting portion forms a light extraction section that comprises: lateral surfaces and at least one of the lateral surfaces is a textured surface with notches, and wherein the textured surface comprises a hydrophilic material configured to optically couple the light with mucus or fluids of the nasal cavity of the user.

37. The illumination device of claim 36, further comprising a housing and a connector, wherein the connector is configured to engage the housing and removably attach the light guide to the housing.

38. The illumination device of claim 37, wherein the at least one light source is positioned within the housing.

39. The illumination device of claim 36, wherein the material of the light guide is a flexible material for traversing the nostril and internal nasal valve during insertion.

40. An illumination device comprising:
at least one light source;
driver circuitry configured to drive the at least one light source;
a light guide that is optically coupled to the at least one light source, the light guide comprising a material that forms a light transmitting portion and a light emitting portion such that at least a portion of light from the at least one light source propagates in the material in a direction defined by the light transmitting portion and exits the light guide through the light emitting portion, the light guide being configured to extend through a nostril and an internal nasal valve of a user to position the light emitting portion within a nasal cavity of the user, wherein the material of the light guide at the light emitting portion forms a light extraction section that comprises an increased concentration of disperser materials relative to the remainder of the light guide; and a plurality of guiding features that are distributed along portions of the light guide that provide extra weight of the light guide to position the light guide along lower portions of at least one of the nasal cavity, an oropharynx, or a nasopharynx of the user, wherein the plurality of guiding features comprise metal such that the plurality of guiding features are configured for steering and bending the light guide in a desired direction within the user by a magnet that is positioned outside the nasal cavity.

41. The illumination device of claim 40, further comprising a housing and a connector, wherein the connector is configured to engage the housing and removably attach the light guide to the housing.

42. The illumination device of claim 41, wherein the at least one light source is positioned within the housing.

43. The illumination device of claim 40, wherein the material of the light guide is a flexible material for traversing the nostril and internal nasal valve during insertion and for bending the light guide in the desired direction.

* * * * *

UNITED STATES PATENT AND TRADEMARK OFFICE
CERTIFICATE OF CORRECTION

PATENT NO. : 11,654,294 B2
APPLICATION NO. : 17/201120
DATED : May 23, 2023
INVENTOR(S) : Antony Paul van de Ven and Michael John Bergmann It is certified that error appears in the above-identified patent and that said Letters Patent is hereby corrected as shown below:

In the Specification
Column 17, Lines 44-45, replace "provided in a range from 120 degrees to 50 degrees" with
--provided in a range from 120 degrees to 150 degrees--.

Signed and Sealed this
Fourth Day of July, 2023

*Katherine Kelly Vidal*
Katherine Kelly Vidal
*Director of the United States Patent and Trademark Office*